(12) United States Patent
Schwager

(10) Patent No.: US 10,112,992 B2
(45) Date of Patent: *Oct. 30, 2018

(54) ANTIGENS ASSOCIATED WITH ENDOMETRIOSIS, PSORIATIC ARTHRITIS AND PSORIASIS

(71) Applicant: Philogen S.P.A., Siena (IT)

(72) Inventor: Kathrin Schwager, Aadorf (CH)

(73) Assignee: Philogen S.P.A., Siena (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/358,173

(22) Filed: Nov. 22, 2016

(65) Prior Publication Data
US 2017/0183398 A1    Jun. 29, 2017

Related U.S. Application Data

(62) Division of application No. 13/140,492, filed as application No. PCT/EP2009/009282 on Dec. 28, 2009, now Pat. No. 9,527,907.

(60) Provisional application No. 61/142,962, filed on Jan. 7, 2009.

(51) Int. Cl.
| | | |
|---|---|---|
| A61K 39/395 | (2006.01) | |
| A61K 39/00 | (2006.01) | |
| C07K 16/18 | (2006.01) | |
| A61K 51/10 | (2006.01) | |
| A61K 47/68 | (2017.01) | |

(52) U.S. Cl.
CPC .......... *C07K 16/18* (2013.01); *A61K 47/6843* (2017.08); *A61K 51/1018* (2013.01); *A61K 2039/505* (2013.01); *C07K 2317/21* (2013.01); *C07K 2317/56* (2013.01); *C07K 2317/565* (2013.01); *C07K 2317/567* (2013.01); *C07K 2317/622* (2013.01); *C07K 2317/626* (2013.01)

(58) Field of Classification Search
None
See application file for complete search history.

(56) References Cited

U.S. PATENT DOCUMENTS

| | | | |
|---|---|---|---|
| 5,420,012 A | 5/1995 | Partanen et al. | |
| 9,527,907 B2 * | 12/2016 | Schwager .......... | A61K 51/1018 |
| 2003/0077589 A1 | 4/2003 | Hess-Strump et al. | |
| 2006/0024757 A1 | 2/2006 | Hussa et al. | |
| 2006/0115428 A1 | 6/2006 | Menrad et al. | |
| 2008/0248038 A1 | 10/2008 | Corvinus et al. | |
| 2010/0260707 A1 | 10/2010 | Kaspar et al. | |

FOREIGN PATENT DOCUMENTS

| | | |
|---|---|---|
| EP | 0 580 859 | 2/1994 |
| EP | 0603735 | 6/1994 |
| WO | 2001/083816 | 11/2001 |
| WO | 2004/000216 | 12/2003 |
| WO | 2004/067038 | 8/2004 |
| WO | 2004/094612 | 11/2004 |
| WO | 2005/009366 | 2/2005 |
| WO | 2005/086612 | 9/2005 |
| WO | 2006/026020 | 3/2006 |
| WO | 2006/050834 | 5/2006 |
| WO | 2007128563 | 11/2007 |
| WO | 2008/120101 | 10/2008 |
| WO | 2009/013619 | 1/2009 |
| WO | 2009/056268 | 5/2009 |

OTHER PUBLICATIONS

Marlind, J., et al. "Antibody-mediated delivery of interleukin-2 to the stroma of breast cancer strongly enhances the potency of chemotherapy." Clin Cancer Res. Oct. 15, 2008;14(20):6515-24.

Schliemann, C., et al. "Complete eradication of human B-cell lymphoma xenografts using rituximab in combination with the immunocytokine L19-IL2." Blood. Mar. 5, 2009;113(10):2275-83. Epub Nov. 12, 2008.

Chilosi, M., et al. "Constitutive expression of tenascin in T-dependent zones of human lymphoid tissues." Am J Pathol. Nov. 1993;143(5):1348-55.

Soini, Y., et al. "Tenascin immunoreactivity in normal and pathological bone marrow." J Clin Pathol. Mar. 1993;46(3):218-21.

Estey, E.H., et al. "Modulation of angiogenesis in patients with myelodysplastic syndrome." Best Pract Res Clin Haematol. Dec. 2004;17(4):623-39.

Smolej, L., et al. "Choice of endothelial marker is crucial for assessment of bone marrow microvessel density in chronic lymphocytic leukemia." APMIS. Dec. 2008;116(12):1058-62.

El-Sorady, M., et al. "Bone marrow angiogenesis in Patients with Hematological Malignancies: Role of VEGF." J Egypt. Nat. Cancer Inst., Jun. 2000;12(2):131-136.

Aguayo, A., et al. "Angiogenesis in acute and chronic leukemias and myelodysplastic syndromes." Blood. Sep. 15, 2000;96(6):2240-5.

Schliemann, C., et al. "Three clinical-stage tumor targeting antibodies reveal differential expression of oncofetal fibronectin and tenascin-C isoforms in human lymphoma." Leuk Res. Dec. 2009;33(12):1718-22. Epub Jul. 22, 2009.

(Continued)

*Primary Examiner* — Maher M Haddad
(74) *Attorney, Agent, or Firm* — Kathleen D. Riguat; Dann, Dofman, Herrell and Skillman, P.C.

(57) ABSTRACT

Specific binding members that bind the ED-A isoform of fibronectin for use in methods of diagnosis, detection, imaging and/or treatment of endometriosis, and/or for use in delivery to the neovasculature of endometriotic tissue of a molecule conjugated to the specific binding member. Specific binding members that bind tenascin-C, especially the A1, A2, A3, A4 and/or D domain tenascin-C large isoform, for use in methods of diagnosis, detection, imaging and/or treatment of endometriosis, psoriatic arthritis or psoriasis, and/or for use in delivery to the neovasculature of endometriotic, psoriatic arthritic or psoriatic tissue of a molecule conjugated to the specific binding member.

11 Claims, 13 Drawing Sheets

Specification includes a Sequence Listing.

(56) References Cited

OTHER PUBLICATIONS

Ballard, V.L., et al. "Vascular tenascin-C regulates cardiac endothelial phenotype and neovascularization." FASEB J. Apr. 2006;20(6):717-9. Epub Feb. 6, 2006.

Wang, H.Y. et al., "Identification of a Mutated Fibronectin as a Tumor Antigen Recognized by CD4+ T Cells: Its Role in Extracellular Matrix Formation and Tumor Metastasis", Journal of Experimental Medicine, Jun. 3, 2002; 195(1): 1397-1406.

Kauma, S. et al., "Production of fibronectin by peritoneal macrophages and concentration of fibronectin in peritoneal fluid from patients with or without endometriosis", Obstet. Gynecol., Jul. 1988;72(1): 13-8.

Rybak, J.N. et al., "Ligand-based vascular targeting of disease", ChemMedChem, Jan. 2007;2(1): 22-40.

Rybak, J.N. et al., "The extra-domain a of fibronectin is a vascular marker of solid tumors and metasases", Cancer Res., Nov. 15, 2007;67(22): 10948-57.

Villa, A. et al., "A high-affinity human monoclonal antibody specific to the alternatively spliced EDA domain of fibronectin efficiently targets tumor neo-vasculature in vivo", Int. J. Cancer Jun. 1, 2008;122(11):2405-13.

Marlind, J. et al., "Antibody-mediated delivery of interleukin-2 to the stroma of breast cancer strongly enhances the potency of chemotherapy", Clin. Cancer Res. Oct. 15, 2008;14(20): 6515-24.

Schliemann, C. et al., "Complete eradication of human B-cell lymphoma xenografts using rituximab in combination with the immunocytokine L19-IL2", Blood, Mar. 5, 2009; 113(10): 2275-83. Epub Nov. 12, 2008.

Chilosi, M. et al., "Constitutive expression of tenascin in T-dependenht zones of human lymphoid tissues", Am. J. Pathol., Nov. 1993;143(5):1348-55.

Soini, Y. et al., "Tenascin immunoreactivity in normal and pathological bone marrow", J. Clin. Pathol., Mar. 1993;46(3):218-21.

Estey, E.H. et al., "Modulation of angiogenesis in patients with myelodysplastic syndrome", Best Pract Res Clin Haematol. Dec. 2004;17(4):623-39.

Smolej, L. et al., "Choice of endothelial marker is crucial for assessment of bone marrow microvessel density in chronic lymphocytic leukemia", APMIS, Dec. 2008;116(12):1058-62.

El-Sorady, M. et al., "Bone marrow angiogenesis in Patients with Hematological Malignancies: Role of VEGF", J. Egypt. Nast. Cancer Inst., Jun. 2000;12(2):131-136.

Aguayo, A. et al., "Angiogenesis in acute and chronic leukemias and myelodysplastic syndromes", Blood, Sep. 15, 2000:96(6);2240-5.

Schliemann, C. et al., {"Three clinical-stage tumor targeting antibodies reveal differential expression of oncofetal fibronectin and tenascin-C isoforms in human lymphoma", Leuk. Res. Dec. 2009;33(12):P1718-22. Epub Jul. 22, 2009.

Ballard, V.L. et al., "Vaswcular tenascin-C regulates cardiac endothelial phenotype and neovascularization", FASEB J. Apr. 2006;20(6):717-9. Epub Feb. 6, 2006.

Schwager et al., "The antibody-mediated targeted delivery of interleukin-10 inhibits endometriosis in a syngeneic mouse model", Human Reproduction, vol. 9, No. 9, pp. 1-9, 2011.

Vajdos et al., Comprehensive functional maps of the antigen-binding site of an anti-ErbB2 antibody obtained with shotgun scanning mutagenesis, J. Mol. Biol., Jul. 5, 2002, 320(2): 415-28.

Brown et al., "Tolerance of single, but not multiple, amino acid replacemnts in antibody VH CDR2: a means of minimizing B cell wastage from somatic hypermutation?", J. Immuno. May 1996, 3285-91.

Paul, Fundamental Immunology, 3rd Edition, 1993, pp. 292-295.

Rudikoff et al., Single amino acid substitution altering antigen-binding specificity, Proc. Natl. Sci. USA, Mar. 1982; 79(6):1979-83.

Varma et al., Endometrio9sis and the neoplastic process, Reproduction (2004), 127: 293-304.

Allie, A Search Service for Abbreviation / Long Form, p. 1, Jun. 27, 2012.

Tagashira et al., "Interleukin-10 attenuated TNF—alpha-induced interleukin-6 production in endometriosis stromal cells", Fertility and Sterility, 91(5), Supplement, May 2009.

Olive and Schwartz, Endometriosis, N. Engl. J. Med.,k Jun. 17, 1993;328(24):1759-69.

Borsi, L., et al. Monoclonal antibodies in the analysis of fibronectin isoforms generated by alternative splicing of mRNA precursors in normal and transformed human cells.: J.Cell Biol., 104, 595-600 (1987).

Carnemolla, B., et al. "Identification of a glioblastoma-associated Tenascin-C isoform by a high affinity recombinant antibody." Am.J.Pathol., 154, 1345-1352 (1999).

Tarli, L., et al. "A high-affinity human antibody that targets tumoural blood vessels". Blood, 94, 192-198 (1999).

Carnemolla, B., et al. "A tumor-associated fibronectin isoform generated by alternative splicing of messenger RNA precursors." J Cell Biol. Mar. 1989;108(3):1139-48.

Carnemolla, B., et al. "Phage antibodies with pan-species recognition of the oncofoetal angiogenesis marker fibronectin ED-B domain." Int J Cancer. Nov. 4, 1996;68(3):397-405.

Castellani, P., et al. "The fibronectin isoform containing the ED-B oncofetal domain: a marker of angiogenesis." Int J Cancer. Dec. 1, 1994;59(5):612-8.

Balza, E., et al. "Transforming growth factor beta regulates the levels of different fibronectin isoforms in normal human cultured fibroblasts." FEBS Lett. Feb. 8, 1988;228(1):42-4.

Birchler, M., et al. "Infrared photodetection for the in vivo localisation of phage-derived antibodies directed against angiogenic markers." J Immunol Methods. Dec. 10, 1999;231(1-2):239-48.

Borsi, L., et al. "Transforming growth factor-beta regulates the splicing pattern of fibronectin messenger RNA precursor" FEBS Lett. Feb. 12, 1990;261(1):175-8.

Borsi, L., et al. "The alternative splicing pattern of the tenascin-C pre-mRNA is controlled by the extracellular pH." J Biol Chem. Mar. 17, 1995;270(11):6243-5.

Borsi, L., et al. "Preparation of phage antibodies to the ED-A domain of human fibronectin." Exp Cell Res. May 1, 1998;240(2):244-51.

Brack, S.S., et al. "Tumor-targeting properties of novel antibodies specific to the large isoform of tenascin-C." Clin Cancer Res. May 15, 2006;12(10):3200-8.

Giovannoni, L., et al. "Isolation of anti-angiogenesis antibodies from a large combinatorial repertoire by colony filter screening." Nucleic Acids Res. Mar. 1, 2001;29(5):E27.

Hanahan, D., et al. "The hallmarks of cancer" Cell. Jan. 7, 2000;100(1):57-70.

Holt, L.J., et al. "Domain antibodies: proteins for therapy." Trends Biotechnol. Nov. 2003;21(11):484-90.

Kaspar, M., et al. "Fibronectin as target for tumor therapy." Int J Cancer. Mar. 15, 2006;118(6):1331-9.

Neri, D., et al. "Tumour vascular targeting." Nat Rev Cancer. Jun. 2005;5(6):436-46.

Oyama, F., et al. "Deregulation of alternative splicing of fibronectin pre-mRNA in malignant human liver tumors." J Biol Chem. Jun. 25, 1989;264(18):10331-4.

Scarpino, S., et al. "Expression of EDA/EDB isoforms of fibronectin in papillary carcinoma of the thyroid." J Pathol. Jun. 1999;188(2):163-7.

Thorpe, P.E. "Vascular targeting agents as cancer therapeutics." Clin Cancer Res. Jan. 15, 2004;10(2):415-27.

Trachsel, E, et al. "Antibodies for angiogenesis inhibition, vascular targeting and endothelial cell transcytosis." Adv Drug Deliv Rev. Aug. 7, 2006;58(5-6):735-54. Epub May 20, 2006.

Borsi, L., et al. "Selective targeting of tumoral vasculature: comparison of different formats of an antibody (L19) to the ED-B domain of fibronectin." Int J Cancer. Nov. 1, 2002;102(1):75-85.

Demartis, S., et al. "Selective targeting of tumour neovasculature by a radiohalogenated human antibody fragment specific for the ED-B domain of fibronectin." Eur J Nucl Med. Apr. 2001;28(4):534-9.

Viti, F., et al. "Increased binding affinity and valence of recombinant antibody fragments lead to improved targeting of tumoral angiogenesis." Cancer Res. Jan. 15, 1999;59(2):347-52.

Linnala, A., et al. "Isoforms of cellular fibronectin and tenascin in amniotic fluid." FEBS Lett. Jan. 10, 1994;337(2):167-70.

(56) References Cited

OTHER PUBLICATIONS

Vartio, T., et al. "Differential expression of the ED sequence-containing form of cellular fibronectin in embryonic and adult human tissues." J Cell Sci. Nov. 1987;88 ( Pt 4):419-30.

Schwager, K., et al. "Preclinical characterization of DEKAVIL (F8-IL10), a novel clinical-stage immunocytokine which inhibits the progression of collagen-induced arthritis." Arthritis Res Ther. 2009;11(5):R142. Epub Sep. 25, 2009.

Oyama, F., et al. "Oncodevelopmental regulation of the alternative splicing of fibronectin pre-messenger RNA in human lung tissues." Cancer Res. Feb. 15, 1990;50(4):1075-8.

Berndt, A., et al. "Evidence of ED-B+ fibronectin synthesis in human tissues by non-radioactive RNA in situ hybridization. Investigations on carcinoma (oral squamous cell and breast carcinoma), chronic inflammation (rheumatoid synovitis) and fibromatosis (Morbus Dupuytren)." Histochem Cell Biol. Mar. 1998;109(3):249-55.

Taylor, P.C. "VEGF and imaging of vessels in rheumatoid arthritis." Arthritis Res. 2002;4 Suppl 3:S99-107. Epub May 9, 2002.

Walsh, D.A., et al. "Focally regulated endothelial proliferation and cell death in human synovium." Am J Pathol. Mar. 1998;152(3):691-702.

Kriegsmann, J., et al. "Expression of fibronectin splice variants and oncofetal glycosylated fibronectin in the synovial membranes of patients with rheumatoid arthritis and osteoarthritis." Rheumatol Int. Jan. 2004;24(1):25-33. Epub Apr. 24, 2003.

Trachsel, E., et al. "Antibody-mediated delivery of IL-10 inhibits the progression of established collagen-induced arthritis." Arthritis Res Ther. 2007;9(1):R9.

Chevalier, X., et al. "Presence of ED-A containing fibronectin in human articular cartilage from patients with osteoarthritis and rheumatoid arthritis." J Rheumatol. Jun. 1996;23(6):1022-30.

Caludepierre, P., et al. "Increased Ed-B fibronectin plasma levels in spondyloarthropathies: comparison with rheumatoid arthritis patients and a healthy population." Rheumatology (Oxford). Nov. 1999;38(11):1099-103.

Davies, J., et al. "Affinity improvement of single antibody VH domains: residues in all three hypervariable regions affect antigen binding." Immunotechnology. Sep. 1996;2(3):169-79.

Liao, Y.F., et al. "The EIIIA segment of fibronectin is a ligand for integrins alpha 9beta 1 and alpha 4beta 1 providing a novel mechanism for regulating cell adhesion by alternative splicing." J Biol Chem. Apr. 26, 2002;277(17):14467-74. Epub Feb. 11, 2002.

Okamura, Y., et al. "The extra domain a of fibronectin activates Toll-like receptor 4." J Biol Chem. Mar. 30, 2001;276(13):10229-33. Epub Jan. 9, 2001.

Peters, J.H., et al. "Preferential recognition of a fragment species of osteoarthritic synovial fluid fibronectin by antibodies to the alternatively spliced EIIIA segment." Arthritis Rheum. Nov. 2001;44(11):2572-85.

Berndt, A., et al. "Differential expression of tenascin-C splicing domains in urothelial carcinomas of the urinary bladder." J Cancer Res Clin Oncol. Aug. 2006;132(8):537-46. Epub May 31, 2006.

Birchler, M., et al. "Selective targeting and photocoagulation of ocular angiogenesis mediated by a phage-derived human antibody fragment." Nat Biotechnol. Oct. 1999;17(10):984-8.

Matter, C.M., et al. "Molecular imaging of atherosclerotic plaques using a human antibody against the extra-domain B of fibronectin." Circ Res. Dec. 10, 2004;95(12):1225-33. Epub Nov. 11, 2004.

Paganelli, G., et al. "Pre-targeted immunodetection in glioma patients: tumour localization and single-photon emission tomography imaging of [99mTc]PnAO-biotin." Eur J Nucl Med. Apr. 1994;21(4):314-21.

Riva, P., et al. "Treatment of intracranial human glioblastoma by direct intratumoral administration of 131I-labelled anti-tenascin monoclonal antibody BC-2." Int J Cancer. Apr. 22, 1992;51(1):7-13.

Riva, P., et al. "Local treatment of malignant gliomas by direct infusion of specific monoclonal antibodies labeled with 131I: comparison of the results obtained in recurrent and newly diagnosed tumors." Cancer Res. Dec. 1, 1995;55(23 Suppl):5952s-5956s.

Schrama, D., et al. "Antibody targeted drugs as cancer therapeutics." Nat Rev Drug Discov. Feb. 2006;5(2):147-59.

Trachsel, E., et al. "A human mAb specific to oncofetal fibronectin selectively targets chronic skin inflammation in vivo." J Invest Dermatol. Apr. 2007;127(4):881-6. Epub Dec. 21, 2006.

Padro, T., et al. "Increased angiogenesis in the bone marrow of patients with acute myeloid leukemia." Blood. Apr. 15, 2000;95(8)2637-44.

Fabbrini, M., et al. "Selective occlusion of tumor blood vessels by targeted delivery of an antibody-photosensitizer conjugate." Int J Cancer. Apr. 1, 2006;118(7)1805-13.

Nilsson, F., et al. "Targeted delivery of tissue factor to the ED-B domain of fibronectin, a marker of angiogenesis, mediates the infarction of solid tumors in mice." Cancer Res. Jan. 15, 2001;61(2):711-6.

* cited by examiner

Figure 6A

F8 VH domain SEQ ID NO: 13

GAGGTGCAGCTGGTGGAGTCTGGGGGAGGCTTGGTACAGCCTGGGGG
GTCCCTGAGACTCTCCTGTGCAGCCTCTGGATTCACCTTTAGCCTGT
TTACGATGAGCTGGGTCCGCCAGGCTCCAGGGAAGGGGCTGGAGTGG
GTCTCAGCTATT*AGTGGTAGTGGTGGTAGC*ACATACTACGCAGACTC
CGTGAAGGGCCGGTTCACCATCTCCAGAGACAATTCCAAGAACACGC
TGTATCTGCAAATGAACAGCCTGAGAGCCGAGGACACGGCCGTATAT
TACTGTGCGAAAAGTACTCATTTGTATCTTTTTGACTACTGGGGCCA
GGGAACCCTGGTCACCGTCTCGAGT

F8 V5L VH domain SEQ ID NO: 15

GAGGTGCAGCTGTTGGAGTCTGGGGGAGGCTTGGTACAGCCTGGGGG
GTCCCTGAGACTCTCCTGTGCAGCCTCTGGATTCACCTTTAGCCTGT
TTACGATGAGCTGGGTCCGCCAGGCTCCAGGGAAGGGGCTGGAGTGG
GTCTCAGCTATT*AGTGGTAGTGGTGGTAGC*ACATACTACGCAGACTC
CGTGAAGGGCCGGTTCACCATCTCCAGAGACAATTCCAAGAACACGC
TGTATCTGCAAATGAACAGCCTGAGAGCCGAGGACACGGCCGTATAT
TACTGTGCGAAAAGTACTCATTTGTATCTTTTTGACTACTGGGGCCA
GGGAACCCTGGTCACCGTCTCGAGT

Figure 6B

F8 linker SEQ ID NO: 121

GGCGGTAGCGGAGGG

Figure 6C

F8 VL domain SEQ ID NO: 75

GAAATTGTGTTGACGCAGTCTCCAGGCACCCTGTCTTTGTCTCCAGG
GGAAAAAGCCACCCTCTCCTGCAGGGCCAGTCAGAGTGTTAGCATGC
CGTTTTTAGCCTGGTACCAGCAGAAACCTGGCCAGGCTCCCAGGCTC
CTCATCTAT*GGTGCATCCAGCAGGGCCACT*GGCATCCCAGACAGGTT
CAGTGGCAGTGGGTCTGGGACAGACTTCACTCTCACCATCAGCAGAC

TGGAGCCTGAAGATTTTGCAGTGTATTACTGTCAGCAG**ATGCGTGGT
CGGCCGCCG**ACGTTCGGCCAAGGGACCAAGGTGGAAATCAAA

Figure 6C cont'd

F8 VL K18R domain SEQ ID NO: 77

GAAATTGTGTTGACGCAGTCTCCAGGCACCCTGTCTTTGTCTCCAGG
GGAAAGAGCCACCCTCTCCTGCAGGGCCAGTCAGAGTGTTAGC<u>ATGC
CGTTTT</u>TAGCCTGGTACCAGCAGAAACCTGGCCAGGCTCCCAGGCTC
CTCATCTAT*GGTGCATCCAGCAGGGCCACT*GGCATCCCAGACAGGTT
CAGTGGCAGTGGGTCTGGGACAGACTTCACTCTCACCATCAGCAGAC
TGGAGCCTGAAGATTTTGCAGTGTATTACTGTCAGCAG**ATGCGTGGT
CGGCCGCCG**ACGTTCGGCCAAGGGACCAAGGTGGAAATCAAA

Figure 7A

F8 VH domain SEQ ID NO: 14

EVQLVESGGGLVQPGGSLRLSCAASGFTFS<u>LF</u>TMSWVRQAPGKGLEW
VSAI*SGSGGS*TYYADSVKGRFTISRDNSKNTLYLQMNSLRAEDTAVY
YCAKSTHLYLFDYWGQGTLVTVSS

F8 V5L VH domain SEQ ID NO: 16

EVQLLESGGGLVQPGGSLRLSCAASGFTFS<u>LF</u>TMSWVRQAPGKGLEW
VSAI*SGSGGS*TYYADSVKGRFTISRDNSKNTLYLQMNSLRAEDTAVY
YCAKSTHLYLFDYWGQGTLVTVSS

Figure 7B

F8 linker SEQ ID NO: 122

GGSGG

Figure 7C

F8 VL domain SEQ ID NO: 76

EIVLTQSPGTLSLSPGEKATLSCRASQSVS<u>MPFLA</u>WYQQKPGQAPRL
LIY*GASSRAT*GIPDRFSGSGSGTDFTLTISRLEPEDFAVYYCQQ**MRG
RPP**TFGQGTKVEIK

F8 K18R VL domain SEQ ID NO: 78

EIVLTQSPGTLSLSPGERATLSCRASQSVS<u>MPFLA</u>WYQQKPGQAPRL
LIY*GASSRAT*GIPDRFSGSGSGTDFTLTISRLEPEDFAVYYCQQ**MRG
RPP**TFGQGTKVEIK

Figure 8A

F16 VH domain SEQ ID NO: 25

GAG GTG CAG CTG TTG GAG TCT GGG GGA GGC TTG GTA
CAG CCT GGG GGG TCC CTG AGA CTC TCC TGT GCA GCC
TCT GGA TTC ACC TTT AGC CGG TAT GGT ATG AGC TGG
GTC CGC CAG GCT CCA GGG AAG GGG CTG GAG TGG GTC
TCA *GCT ATT AGT GGT AGT GGT GGT AGC ACA TAC TAC
GCA GAC TCC GTG AAG GGC* CGG TTC ACC ATC TCC AGA
GAC AAT TCC AAG AAC ACG CTG TAT CTG CAA ATG AAC
AGC CTG AGA GCC GAG GAC ACG GCC GTA TAT TAC TGT
GCG AAA GCG CAT AAT GCT TTT GAC TAC TGG GGC CAG
GGA ACC CTG GTC ACC GTG TCG AGA

4A1-F16 VH domain SEQ ID NO: 27

GAG GTG CAG CTG TTG GAG TCT GGG GGA GGC TTG GTA
CAG CCT GGG GGG TCC CTG AGA CTC TCC TGT GCA GCC
TCT GGA TTC ACC TTT AGC CGG TAT GGT GCG AGC TGG
GTC CGC CAG GCT CCA GGG AAG GGG CTG GAG TGG GTC
TCA *GCT ATT AGT GGT AGT GGT GGT AGC ACA TAC TAC
GCA GAC TCC GTG AAG GGC* CGG TTC ACC ATC TCC AGA
GAC AAT TCC AAG AAC ACG CTG TAT CTG CAA ATG AAC
AGC CTG AGA GCC GAG GAC ACG GCC GTA TAT TAC TGT
GCG AAA GCG CAT AAT GCT TTT GAC TAC TGG GGC CAG
GGA ACC CTG GTC ACC GTG TCG AGA

Figure 8B

F16 linker SEQ ID NO: 121

GGC GGT AGC GGA GGG

Figure 8C

F16 VL domain SEQ ID NO: 87

TCG TCT GAG CTG ACT CAG GAC CCT GCT GTG TCT GTG
GCC TTG GGA CAG ACA GTC AGG ATC ACA TGC <u>CAA GGA</u>
<u>GAC AGC CTC AGA AGC TAT TAT GCA AGC</u> TGG TAC CAG
CAG AAG CCA GGA CAG GCC CCT GTA CTT GTC ATC TAT
*<u>GGT AAA AAC AAC CGG CCC TCA</u>* GGG ATC CCA GAC CGA
TTC TCT GGC TCC AGC TCA GGA AAC ACA GCT TCC TTG
ACC ATC ACT GGG GCT CAG GCG GAA GAT GAG GCT GAC
TAT TAC TGT AAC TCC TCT GTT TAT ACT ATG CCG CCC
GTG GTA TTC GGC GGA GGG ACC AAG CTG ACC GTC CTA

Figure 9A

F16 VH domain SEQ ID NO: 26

EVQLLESGGGLVQPGGSLRLSCAASGFTFSRYGMSWVRQA
PGKGLEWVSAISGSGGSTYYADSVKGRFTISRDNSKNTLY
LQMNSLRAEDTAVYYCAKAHNAFDYWGQGTLVTVSR

4A1-F16 VH domain SEQ ID NO: 28

EVQLLESGGGLVQPGGSLRLSCAASGFTFSRYGASWVRQA
PGKGLEWVSAISGSGGSTYYADSVKGRFTISRDNSKNTLY
LQMNSLRAEDTAVYYCAKAHNAFDYWGQGTLVTVSR

Figure 9B

F16 and 4A1-F16 linker SEQ ID NO: 122

GGSGG

Figure 9C

F16 and 4A1-F16 VL domain SEQ ID NO: 88

SSELTQDPAVSVALGQTVRITCQGDSLRSYYASWYQQKPG
QAPVLVIYGKNNRPSGIPDRFSGSSSGNTASLTITGAQAE
DEADYYCNSSVYTMPPVVFGGGTKLTVL

ANTIGENS ASSOCIATED WITH ENDOMETRIOSIS, PSORIATIC ARTHRITIS AND PSORIASIS

The present application is a divisional application of U.S. patent application Ser. No. 13/140,492 filed Jun. 17, 2011, now U.S. Pat. No. 9,527,907, which is the US National Stage of International Application No. PCT/EP2009/009282, filed Dec. 28, 2009, which claims benefit of U.S. Provisional Application No. 61/142,962, filed Jan. 7, 2009. The entire disclosure of each of the aforesaid applications is incorporated by reference in the present application.

The present invention relates to the detection and treatment of endometriosis, psoriatic arthritis and psoriasis. The invention involves use of a specific binding member that binds the ED-A isoform of fibronectin, especially a specific binding member that binds domain ED-A of fibronectin, or a specific binding member that binds tenascin-C, especially the A1, A2, A3, A4, B and/or D domain of tenascin C (the "long form" of tenascin-C).

Most conventional pharmaceuticals currently in use for the treatment of angiogenesis-related diseases (such as cancer, arthritis, etc.) do not selectively accumulate at the site of disease [Bosslet et al., 58, 1195-1201 Cancer Res. (1998)]. For example, intravenously administered drugs distribute evenly within the different organs and tissues of the body, rather than selectively accumulating at the site of disease.

One approach to circumvent the disadvantages of conventional pharmacological therapies involves the preferential delivery of a bioactive agent to the tumor site by means of a binding molecule specific for a pathology-associated marker [Neri & Bicknell (2005) Nature Rev. Cancer]. The selective targeting of the drug to the diseased tissue will ultimately result in an increased local concentration at its site of action, sparing normal organs from the toxic effects of the bioactive agent used to confer a pharmacological benefit (e.g., a cytotoxic drug, a cytokine, a radionuclide, a photosensitizer). In most cases, this will lead to an improved therapeutic index of the delivered pharmaceutical, i.e. a higher efficacy with minimized side effects. Indeed, the favourable toxicity profile of site-specific therapeutics may open new avenues in the therapy of angiogenesis-related diseases, allowing the systemic administration of highly potent and promising agents, which are currently either given at suboptimal doses or whose clinical application has to date been impeded by unacceptable toxicities when applied in an unmodified form.

Ligand-based pharmacodelivery strategies fundamentally rely on the identification of good-quality markers of pathology, allowing a clear-cut discrimination between diseased tissues and healthy organs. Monoclonal antibodies and their fragments represent the preferred agents for pharmacodelivery applications [Rybak et al. 2, 22-40 Chem. Med. Chem (2007); Shrama et al., 5, 147-159 Nat. Rev. Drug Discovery (2006)], even though globular protein mutants [Binz and Plückthun, 23, 1257-1268 Nature Biotechnology (2005)], peptides [Sergeeva et al., 58, 1622-1654, Adv. Drug. Deliv. Rev. (2006)] and even small organic ligands [Low et al., 41, 120-129, Acc. Chem. Res. (2008)] are increasingly being used. Most efforts in the field of disease targeting have been made using specific markers expressed on the surface of diseased cells (e.g., on the surface of tumour cells in cancer). However, targeting antigens on diseased cells themselves is a complex task for blood-borne agents, facing a number of physical and kinetic barriers, which may prevent efficient pharmacodelivery. These barriers include interstitial pressure at site of disease, relatively long diffusion distances within the interstitium, heterogeneity of antigens at sites of disease, as well as the so-called "antigen barrier" [Dennis et al., 67, 254-261, Cancer Res. (2007)]. All these factors significantly impair deep tissue penetration.

Proteins which are expressed around pathological blood vessels at sites of disease, but which are either absent or present at reduced levels in normal tissue, represent particularly attractive targets for the development of selective and efficient pharmacodelivery strategies [Rybak et al. (2007) ChemMedChem; Trachsel et al., 9, R9, Arthritis Res. Ther. (2007)]. Vascular targets are often more easily accessible from the bloodstream to systemically administered agents, overcoming the problem of access and allowing an efficient delivery of the compound to the site of disease. Furthermore, the same vascular targeting agent could be useful not only for the delivery of therapeutic agents but also for molecular imaging applications.

As used herein, the term "vascular targeting" is not used to indicate the inhibition of the target molecule in a signalling pathway (e.g. the inhibition of VEGF signalling by bevacizumab or the inhibition of the BCR/ABL kinase by imatinib). Instead, the target molecule expressed on the vasculature at sites of angiogenesis-related diseases is used as an easily accessible binding site for specific ligands, exploiting the vasculature as a scaffold to achieve a site-specific localization of effector molecules at the tumour tissue. This fundamental conceptual difference is clear from the fact that, while some vascular marker molecules have been shown to be very suitable for ligand-directed tumour targeting applications, their pathophysiological role is still largely unknown (for example, the extra-domain B of fibronectin; see below).

The present inventors have previously performed extensive work on the antibody-based targeting of markers of tumor angiogenesis, such as the extra-domain B of fibronectin (ED-B) [Schliemann and Neri, 1776, 175-192, Biochim Biophys Acta (2008)]. ED-B is virtually undetectable in normal adult tissues, except for the endometrium in the proliferative phase, but becomes over-expressed in conditions involving tissue remodelling, with a prominent perivascular pattern of staining. Three derivatives of the human anti-EDB antibody L19 [Pini et al. (1998) J. Biol. Chem.] are currently being investigated in Phase I and Phase II clinical trials for cancer therapy (the radiolabelled product L19-$^{131}$I and the immunocytokines L19-IL2 and L19-TNF). The ability of L19 to selectively localize at angiogenic sites in non-tumoral diseases has been studied in animal models of ocular neo-vasculature [Birchler et al. 17, 984-988, Nature Biotechnology (1999)], rheumatoid arthritis [Trachsel et al., 9, R9, Arthritis Res. Ther. (2007)], psoriasis [Trachsel et al., 127, 881-886, J. Inv. Dermatol. (2007)] and atherosclerosis [Matter et al., 95, 1225-1233 Circulation Res. (2004)].

More recently, the present inventors have studied other alternatively spliced domains of extracellular matrix components, whose patterns of expression are less well characterized and which have so far been used mainly as vascular targets for tumour targeting applications: the ED-A domain of fibronectin [Rybak et al., 67, 10948-10957 (2007) Cancer Res.] and the domain A1 of tenascin-C [Brack et al., 12, 3200-3208, (2006) Clin. Cancer Res.]. ED-A is specifically recognized by the human monoclonal antibody F8 [Villa et al., 122, 2405-2413 (2008) Int. J. Cancer], while the human monoclonal antibody F16 binds the A1 domain of tenascin-C [Brack et al. (2006) Clin. Cancer Res.].

The pattern of expression of the extra-domains A1, A2, A3, A4, B and D of tenascin-C are similar, being almost undetectable in normal adult tissues, but strongly up-regulated in a multitude of different tumours [Brack et al. (2006) Clin. Cancer Res.; Pedretti et al. (2008) Lung Cancer, in press; Berndt et al., 132, 537-546, J Cancer Res Clin Oncol (2006); Balza et al., 261, 175-178, FEBS Lett. (1990)]. The term "tenascin-C large isoform" is often used to indicate the form of tenascin-C containing the extra-domains A1, A2, A3, A4, B and D [Borsi et al., 270, 6243-6245 (1995) J. Biol. Chem.; Borsi et al., 66, 632-635 (1996) Int. J. Cancer; Carnemolla et al., 154, 1345-1352 (1999) Am. J. Pathol.]. By contrast, the expression of the extra-domain C of tenascin-C is more restricted, being undetectable in normal adult tissues and being found only in certain tumour types, mainly lung cancer and high-grade astrocytomas [Carnemolla et al. (1999) Am. J. Pathol.].

Thus, antibody-based targeted delivery of bioactive agents to sites of angiogenesis is an attractive therapeutic strategy for cancer treatment, but is largely unexplored for chronic inflammatory diseases. We have previously demonstrated that the ED-B domain of fibronectin, a marker of angiogenesis, is expressed in psoriatic lesions in patients and in a mouse model of psoriasis as well as in arthritic paws in the collagen-induced mouse model of rheumatoid arthritis. Using both radioactive and fluorescent techniques, the human monoclonal antibody L19, specific to EDB, was found to selectively localize at sites of inflammation in vivo, following intravenous administration. These results suggest a therapeutic potential for the L19-based selective delivery of bioactive compounds to sites of inflammation (Trachsel, 2007; PCT/EP2007/004044).

It has also previously been shown by in-situ-hybridisation that the ED-A domain of fibronectin can be present in human arthritic specimens (Berndt et al., 1998; Kriegsmann et al., 2004), and the inventors have previously shown the expression of ED-A in rheumatoid arthritis [PCT/EP2008/009070].

We show herein the patterns of expression of ED-A and of tenascin-C large in other angiogenesis-related non-tumoural diseases, such as multiple sclerosis, psoriatic arthritis, psoriasis, inflammatory bowel diseases and endometriosis, using identical concentrations of biotinylated versions of the F8 and F16 antibodies in SIP format [Borsi et al., 102, 75-85 (2002) Int. J. Cancer; Villa et al., 122, 2405-2413 (2008) Int. J. Cancer; Brack et al., 12, 3200-3208, (2006) Clin. Cancer Res.]. These diseases are all associated with angiogenesis and are socially very relevant. Ligand-based pharmacodelivery may open new diagnostic and therapeutic opportunities for these diseases.

Multiple sclerosis is an autoimmune disease in which the immune system attacks the nervous system, resulting in demyelination of neurones (Compston and Coles, 359, 1221-1231, Lancet, 2002). As well as demyelination, multiple sclerosis is also characterised by inflammation. There is no known cure for multiple sclerosis and many existing medications can have adverse side effects or be poorly tolerated.

Psoriasis is a disease which affects the skin and joints, usually by causing red, scaly psoriatic plaques to occur on the skin. These psoriatic plaques are areas of inflammation. When psoriasis causes inflammation of the joints, it is known as psoriatic arthritis. More effective treatments of psoriasis and psoriatic arthritis are required and one approach would be the targeted delivery of anti-inflammatory cytokines, such as IL-10 or TGF-β, photosensitisers or cytotoxic drugs with cleavable linkers. Such an approach requires effective targeting of drugs to areas of inflammation, and the identification of specific targets expressed in these regions.

The main forms of inflammatory bowel disease are Crohn's disease and ulcerative colitis. Crohn's disease can affect any part of the gastrointestinal tract, whereas ulcerative colitis is restricted to the colon and rectum (Summers et al., 2003). Depending on its severity, treatment of ulcerative colitis may require immunosuppression to control its symptoms and treatment usually involves the administration of anti-inflammatory molecules.

Endometriosis is a common medical condition in women, and is characterized by growth beyond or outside the uterus of tissue resembling endometrium, which normally lines the uterus (Rock and Markham, 340, 1264-1267 (1992) Lancet).

Endometriosis is typically seen during the reproductive years, and it has been estimated that it occurs in approximately 5% to 10% of women. Its main, but not universal, symptom is pelvic pain in various manifestations. Further, endometriosis is common in women with infertility (Buyalos and Agarwal, 12, 377-381, (2000) Curr Opin Obstet Gynecol).

A major symptom of endometriosis is severe recurring pelvic pain. The amount of pain a woman feels is not necessarily related to the extent or stage (1 through to 4) of endometriosis. Some women will have little or no pain despite having extensive endometriosis affecting large areas or having endometriosis with scarring. On the other hand, women may have severe pain even though they have only a few small areas of endometriosis (Muse K, 31, 813-822 (1988) Clin Obstet Gynecol).

Typical endometriotic lesions show histological features similar to endometrium, namely stroma and endometrial epithelium and glands that respond to hormonal stimuli. Older lesions may display no glands, but residual hemosiderin deposits. To the eye, lesions appear dark blue or powder-burn black and vary in size; some other lesions are red, white, or non-pigmented.

Additionally other lesions may be present, notably endometriomas of the ovary, scar formation, and peritoneal defects or pockets. As normal appearing peritoneum of infertile women reveals endometriosis on biopsy in 6-13% of cases, some lesions may not be visible to the eye.

A health history and a physical examination can in many patients lead the physician to suspect endometriosis.

Use of imaging tests may identify larger endometriotic areas, such as nodules or endometriotic cysts. The two most common imaging tests are ultrasound and magnetic resonance imaging (MRI). However, normal results on these tests do not eliminate the possibility of endometriosis, as areas of endometriosis are often too small to be seen by these tests.

The only way to confirm and diagnose endometriosis is by laparoscopy, or other types of surgery. The diagnosis is based on the characteristic appearance of the disease, and is corroborated by a biopsy, if necessary. Laparoscopy also allows for surgical treatment of endometriosis (Brosens I., 15, 229-233 (1997) Semin Reprod Endocrinol).

For this reason, the discovery of good-quality vascular markers of endometriosis provides new opportunities for imaging endometriosis (e.g. through the ligand-mediated delivery of radionuclides and radioisotopes), and for the pharmacodelivery to endometriotic tissue of bioactive molecules (such as cytokines, hormones, therapeutic radionuclides, or drugs with cleavable linkers).

We show herein that an anti-tenascin-C antibody, such as the F16 antibody disclosed herein, is able to give a stronger staining pattern on human endometriotic tissue than the anti-ED-B antibody L19. Similarly, an anti-ED-A antibody, such as the F8 antibody disclosed herein, is also able to give a stronger staining pattern on human endometriotic tissue than the anti-ED-B antibody L19, although the staining seen with the F8 antibody is not as intense as that seen with the F16 antibody.

We also shown herein that an anti-tenascin-C antibody, such as the F16 antibody disclosed herein, is able to give a stronger staining pattern on human psoriatic arthritic tissue than the anti-ED-B antibody L19, or the anti-ED-A antibody F8.

However, we show herein that staining of samples from patients with ulcerative colitis is virtually negative for the anti-tenascin-C antibody F16, the anti-ED-A antibody F8 and the anti-ED-B antibody L19, with only a weak positivity being observed with F8 in some specimens.

Analysis of tissue sections from pathological specimens of patients with multiple sclerosis also revealed only very weak positivity with the anti-tenascin-C antibody F16, the anti-ED-A antibody F8 and the anti-ED-B antibody L19.

In the case of components of the modified subendothelial matrix, in vivo targeting performance of antibody derivatives correlates with abundant antigen expression [Borsi et al., 102, 75-85 (2002) Int. J. Cancer; Demartis et al., 28, 534-539 (2001) Eur. J. Nucl. Med.; Tarli et al., 94, 192-198 (1999) Blood; Viti et al., 59, 347-352, (1999) Cancer Res.]. Based on the findings described above, we found that the expression of ED-A and of the tenascin-C "large" isoform is not found in all angiogenesis-related diseases, and that endometriosis appears to be particularly suited for pharmacodelivery using anti-ED-A antibody molecules, while endometriosis, psoriatic arthritis and psoriasis appear to be particularly suited for pharmacodelivery using anti-tenascin-C antibody molecules.

Accordingly, ED-A of fibronectin is indicated as a vascular marker of endometriosis, while tenascin-C (in particular, the "large" isoform of tenascin-C) is indicated as a vascular marker of endometriosis, psoriatic arthritis and psoriasis.

Specific binding members, such as antibody molecules that bind the ED-A of fibronectin, represent novel agents which may be used for the treatment of endometriosis, while specific binding members, such as antibody molecules that bind the "large" isoform of tenascin-C, represent novel agents which may be used for the treatment of endometriosis, psoriatic arthritis, or psoriasis.

In a first aspect, the invention provides a specific binding member, e.g. an antibody molecule, that binds the Extra Domain-A (ED-A) isoform of fibronectin (A-FN) for use in a method of treatment of endometriosis. The invention also provides the use of a specific binding member, e.g. an antibody molecule, that binds the Extra Domain-A (ED-A) isoform of fibronectin for the manufacture of a medicament for treating endometriosis. The invention also provides a method of treating endometriosis in a patient, the method comprising administering to a patient a therapeutically effective amount of a medicament comprising a specific binding member which binds the ED-A isoform of fibronectin. Preferably, the specific binding member binds the ED-A isoform of human fibronectin.

The specific binding member, e.g. an antibody molecule, for use in this first aspect of the invention, may bind the ED-A of fibronectin.

The specific binding member e.g. an antibody molecule, for use in this first aspect of the invention, may be conjugated to a detectable label, a radioisotope, or a bioactive molecule, such as a cytokine, a hormone, a therapeutic radioisotope or a cytotoxic drug. The specific binding member may be conjugated to the bioactive molecule by a cleavable linker.

In a second aspect, the invention provides a specific binding member, e.g. an antibody molecule, that binds the ED-A isoform of fibronectin for use in the delivery to the neovasculature of endometriotic tissue of a molecule conjugated to the specific binding member. The invention also provides the use of a specific binding member, e.g. an antibody molecule, that binds the ED-A isoform of fibronectin for the manufacture of a medicament for delivery to the neovasculature of endometriotic tissue of a molecule conjugated to the specific binding member. The invention also provides a method of delivering a molecule to the neovasculature of endometriotic tissue in a human or animal, wherein the molecule is conjugated to a specific binding member which binds the ED-A isoform of fibronectin to form a conjugate and the method comprises administering the conjugate to the human or animal. Preferably, the specific binding member binds the ED-A isoform of human fibronectin.

The specific binding member, e.g. an antibody molecule, for use in this second aspect of the invention, may bind the ED-A of fibronectin.

The specific binding member e.g. an antibody molecule, for use in this second aspect of the invention, may be conjugated to a detectable label, a radioisotope, or a bioactive molecule, such as a cytokine, a hormone, a therapeutic radioisotope or a cytotoxic drug. The specific binding member may be conjugated to the bioactive molecule by a cleavable linker.

In a third aspect, the invention provides a specific binding member, e.g. an antibody molecule, that binds the ED-A isoform of fibronectin for use in a method of diagnosis of endometriosis. The invention also provides use of a specific binding member that binds the ED-A isoform of fibronectin for the manufacture of a diagnostic product for diagnosing endometriosis. The invention also provides a method of detecting or diagnosing endometriosis in a human or animal, wherein the method comprises the steps of:
  (a) administering to the human or animal a specific binding member which binds the ED-A domain of fibronectin, and
  (b) determining the presence or absence of the specific binding member in sites of endometriosis of the human or animal body,
    wherein localisation of the specific binding member to site of endometriosis indicates the presence of endometriosis.

Preferably, the specific binding member binds the ED-A isoform of human fibronectin.

The specific binding member, e.g. an antibody molecule, for use in this third aspect of the invention, may bind the ED-A of fibronectin.

The specific binding member e.g. an antibody molecule, for use in this third aspect of the invention, may be conjugated to a detectable label, or a radioisotope.

In a fourth aspect, the invention provides a specific binding member that binds the ED-A isoform of fibronectin for use in a method of imaging endometriotic tissue. The invention also provides use of a specific binding member that binds the ED-A isoform of fibronectin for the manufacture of an imaging agent for imaging endometriotic tissue. The invention also provides a method of detecting or imaging endometriotic tissue in a human or animal, wherein the method comprises the steps of:

(a) administering to the human or animal a specific binding member which binds the ED-A domain of fibronectin, and
(b) detecting the binding of the specific binding member to endometriotic tissue in the human or animal body.

Preferably, the specific binding member binds the ED-A isoform of human fibronectin.

The specific binding member, e.g. an antibody molecule, for use in this fourth aspect of the invention, may bind the ED-A of fibronectin.

The specific binding member e.g. an antibody molecule, for use in this fourth aspect of the invention, may be conjugated to a detectable label, or a radioisotope.

A specific binding member for use in the invention may be an antibody which binds the ED-A isoform of fibronectin and/or the ED-A of fibronectin, wherein the antibody comprises one or more complementarity determining regions (CDRs) of antibody H1, B2, C5, D5, E5, C8, F8, F1, B7, E8 or G9, or variants thereof. F8, D5 and B7 are disclosed in Villa et al., 122, 2405-2413 (2008) Int. J. Cancer, while H1, B2, C5, E5, C8, F1, E8 and G9 (and also F8, D5 and B7) are disclosed in WO 2008/120101. Preferably, a specific binding member for use in the invention is an antibody which binds the ED-A isoform of fibronectin and/or the ED-A of fibronectin, comprising one or more complementarity determining regions (CDRs) of antibody B2, C5, D5, C8, F8, B7 or G9, or variants thereof. Preferably, the specific binding member binds the ED-A isoform of human fibronectin. Most preferably, a specific binding member for use in the invention is an antibody which binds the ED-A isoform of fibronectin and/or the ED-A of fibronectin, comprising one or more complementarity determining regions (CDRs) of antibody F8, or variants thereof.

Preferably, a suitable variant for use as described herein comprises an antibody antigen binding site comprising a VH domain and a VL domain of any one of antibodies F8, H1, B2, C5, D5, E5, C8, F1, B7, E8 and G9, wherein the valine (V) residue at position 5 of the VH domain is substituted with leucine (L), and/or the lysine (K) residue at position 18 of the VL domain is substituted with arginine (R). Most preferably, a suitable variant for use as described herein comprises an antibody antigen binding site comprising the F8 VH V5L domain of SEQ ID NO: 16 and the F8 VL K18R domain of SEQ ID NO: 78, wherein the valine (V) residue at position 5 of the VH domain is substituted by leucine (L), and/or the lysine (K) residue at position 18 of the VL domain is substituted by arginine (R).

A specific binding member for use in the invention may comprise a set of H and/or L CDRs of antibody H1, B2, C5, D5, E5, C8, F8, F1, B7, E8 or G9, or a set of H and/or L CDRs of antibody H1, B2, C5, D5, E5, C8, F8, F1, B7, E8 or G9 with ten or fewer, e.g. one, two, three, four, or five, amino acid substitutions within the disclosed set of H and/or L CDRs. Preferably, a specific binding member for use in the invention comprises a set of H and/or L CDRs of antibody B2, C5, D5, C8, F8, B7 or G9 with ten or fewer, e.g. one, two, three, four, or five, amino acid substitutions within the disclosed set of H and/or L CDRs. Preferably, a specific binding member for use in the invention comprises a set of H and/or L CDRs of antibody F8 with ten or fewer, e.g. one, two, three, four, or five, amino acid substitutions within the disclosed set of H and/or L CDRs.

Substitutions may potentially be made at any residue within the set of CDRs, and may be within CDR1, CDR2 and/or CDR3.

For example, a specific binding member for use in the invention may comprise one or more CDRs as described herein, e.g. a CDR3, and optionally also a CDR1 and CDR2 to form a set of CDRs.

A specific binding member for use in the invention may also comprise an antibody molecule, e.g. a human antibody molecule. The specific binding member normally comprises an antibody VH and/or VL domain. VH domains of specific binding members are also provided for use in the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. The VH and VL domains and CDRs of antibodies H1, B2, C5, D5, E5, C8, F8 (and its variant comprising V5L VH and K18R VL), F1, B7, E8 and G9 are described herein. All VH and VL sequences, CDR sequences, sets of CDRs and sets of HCDRs and sets of LCDRs disclosed herein represent embodiments of a specific binding member for use in the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

A specific binding member for use in the invention may comprise an antibody VH domain comprising complementarity determining regions HCDR1, HCDR2 and HCDR3 and a framework, wherein HCDR1 is SEQ ID NO: 30, 32, 34, 36, 38, 40, 42, 44, 46, 48, or 50, and wherein optionally HCDR2 is SEQ ID NO: 56, and/or HCDR3 is SEQ ID NO: 60. Preferably, the HCDR1 is SEQ ID NO: 42.

Typically, a VH domain is paired with a VL domain to provide an antibody antigen-binding site, although as discussed further below, a VH or VL domain alone may be used to bind antigen. Thus, a specific binding member for use in the invention may further comprise an antibody VL domain comprising complementarity determining regions LCDR1, LCDR2 and LCDR3 and a framework, wherein LCDR1 is SEQ ID NO: 90, 92, 94, 96, 98, 100, 102, 104, 106, 108, or 110, and wherein optionally LCDR2 is SEQ ID NO: 114 and/or LCDR3 is SEQ ID NO: 118. Preferably, the LCDR1 is SEQ ID NO: 102.

A specific binding member for use in the invention may be an isolated antibody molecule for the ED-A of fibronectin, comprising a VH domain and a VL domain, wherein the VH domain comprises a framework and a set of complementarity determining regions HCDR1, HCDR2 and HCDR3 and wherein the VL domain comprises complementarity determining regions LCDR1, LCDR2 and LCDR3 and a framework, and wherein HCDR1 has amino acid sequence SEQ ID NO: 30, 32, 34, 36, 38, 40, 42, 44, 46, 48, or 50;
HCDR2 has amino acid sequence SEQ ID NO: 56;
HCDR3 has amino acid sequence SEQ ID NO: 60;
LCDR1 has amino acid sequence SEQ ID NO: 90, 92, 94, 96, 98, 100, 102, 104, 106, 108, or 110;
LCDR2 has amino acid sequence SEQ ID NO: 114; and
LCDR3 has amino acid sequence SEQ ID NO: 118.

Preferably, the HCDR1 is SEQ ID NO: 42, and the LCDR1 is SEQ ID NO: 102.

One or more CDRs or a set of CDRs of an antibody may be grafted into a framework (e.g. human framework) to provide an antibody molecule for use in the invention.

Framework regions may comprise human germline gene segment sequences. Thus, the framework may be germlined, whereby one or more residues within the framework are changed to match the residues at the equivalent position in the most similar human germline framework. A specific binding member for use in the invention may be an isolated antibody molecule having a VH domain comprising a set of HCDRs in a human germline framework, e.g. DP47. Normally the specific binding member also has a VL domain comprising a set of LCDRs, e.g. in a human germline framework. The human germline framework of the VL domain may be DPK22.

A VH domain for use in the invention may have amino acid sequence SEQ ID NO: 2, 4, 6, 8, 10, 12, 14, 16, 18, 20, 22, or 24.

Preferably, a VH domain for use in the invention has amino acid sequence SEQ ID NO: 14 or 16. A VL domain for use in the invention may have the amino acid SEQ ID NO: 64, 66, 68, 70, 72, 74, 76, 78, 80, 82, 84, or 86. Preferably, a VL domain for use in the invention has amino acid SEQ ID NO: 76 or 78.

A specific binding member for use in the invention may be or comprise a single chain Fv (scFv), comprising a VH domain and a VL domain joined via a peptide linker. The skilled person may select an appropriate length and sequence of linker, e.g. at least 5 or at least 10 amino acids in length, up to about 15, up to about 20 or up to about 25 amino acids in length. The linker may have the amino acid sequence GSSGG (SEQ ID NO: 122).

The specific binding member may be a diabody, which is a multivalent or multispecific fragment constructed by gene fusion (WO94/13804; Holliger 1993a).

A single chain Fv (scFv) may be comprised within a mini-immunoglobulin or small immunoprotein (SIP), e.g. as described in (Li et al., 1997). An SIP may comprise an scFv molecule fused to the CH4 domain of the human IgE secretory isoform IgE-S2 ($\varepsilon_{s2}$-CH4; Batista et al., 1996) forming an homo-dimeric mini-immunoglobulin antibody molecule.

Alternatively, a specific binding member for use in the invention may comprise an antigen-binding site within a non-antibody molecule, normally provided by one or more CDRs e.g. a set of CDRs in a non-antibody protein scaffold. Specific binding members, including non-antibody and antibody molecules, are described in more detail elsewhere herein.

According to a fifth aspect, the invention provides a specific binding member that binds tenascin-C for use in a method of treatment of endometriosis, psoriatic arthritis or psoriasis. The invention also provides use of a specific binding member that binds tenascin-C for the manufacture of a medicament for treating endometriosis, psoriatic arthritis or psoriasis. The invention also provides a method of treating endometriosis, psoriatic arthritis or psoriasis in a patient, the method comprising administering to a patient a therapeutically effective amount of a medicament comprising a specific binding member which binds tenascin-C. Preferably, the specific binding member binds human tenascin-C.

The specific binding member, e.g. an antibody molecule, for use in this fifth aspect of the invention may bind specifically to tenascin-C large isoform. For example, the specific binding member may bind preferentially to tenascin-C large isoform relative to tenascin-C small isoform. Preferably, the specific binding member binds to the A1, A2, A3, A4, B and/or D domain of tenascin-C large isoform. Most preferably, the specific binding member binds to the A1 domain of tenascin-C.

The specific binding member, e.g. an antibody molecule, for use in this fifth aspect of the invention, may be conjugated to a detectable label, a radioisotope, or a bioactive molecule, such as a cytokine, hormone, a therapeutic isotope, or a cytotoxic drug. For example, the specific binding member may be conjugated to a cytokine, such as IL-10, TGF-β, IL-2, IL-12, IL-15, IL-21, IL-24, IL-33, tumour necrosis factor (TNF), or interferon-α, -β or -γ. The specific binding member may be conjugated to the bioactive molecule by a cleavable linker.

According to a sixth aspect, the invention provides a specific binding member that binds tenascin-C, for use in the delivery to the neovasculature of endometriotic, psoriatic arthritic or psoriatic tissue of a molecule conjugated to the specific binding member. The invention also provides use of a specific binding member that binds tenascin-C for the manufacture of a medicament for delivery of a molecule conjugated to the specific binding member to the neovasculature of endometriotic, psoriatic arthritic or psoriatic tissue. The invention also provides a method of delivering a molecule to the neovasculature of endometriotic, psoriatic arthritic or psoriatic tissue in a human or animal, wherein the molecule is conjugated to a specific binding member which binds tenascin-C to form a conjugate and the method comprises administering the conjugate to the human or animal. Preferably, the specific binding member binds human tenascin-C.

The specific binding member, e.g. an antibody molecule, for use in this sixth aspect of the invention may bind specifically to tenascin-C large isoform. For example, the specific binding member may bind preferentially to tenascin-C large isoform relative to tenascin-C small isoform. Preferably, the specific binding member binds to the A1, A2, A3, A4, B and/or D domain of tenascin-C large isoform. Most preferably, the specific binding member binds to the A1 domain of tenascin-C.

The specific binding member, e.g. an antibody molecule, for use in this sixth aspect of the invention, may be conjugated to a detectable label, a radioisotope, or a bioactive molecule, such as a cytokine, hormone, a therapeutic isotope, or a cytotoxic drug. For example, the specific binding member may be conjugated to a cytokine, such as IL-10, TGF-β, IL-2, IL-12, IL-15, IL-21, IL-24, IL-33, tumour necrosis factor (TNF), or interferon-α, -β or -γ. The specific binding member may be conjugated to the bioactive molecule by a cleavable linker.

According to a seventh aspect, the invention provides a specific binding member that binds tenascin-C for use in a method of diagnosis of endometriosis, psoriatic arthritis or psoriasis. The invention also provides use of a specific binding member that binds tenascin-C for the manufacture of a diagnostic product for diagnosing endometriosis, psoriatic arthritis or psoriasis. The invention also provides a method of detecting or diagnosing endometriosis, psoriatic arthritis or psoriasis in a human or animal, wherein the method comprises the steps of:
  (a) administering to the human or animal a specific binding member which binds tenascin-C, and
  (b) determining the presence or absence of the specific binding member in sites of endometriosis, psoriatic arthritis or psoriasis of the human or animal body;

wherein localisation of the specific binding member to sites of endometriosis, psoriatic arthritis or psoriasis indicates the presence of endometriosis, psoriatic arthritis or psoriasis.

Preferably, the specific binding member binds human tenascin-C.

The specific binding member, e.g. an antibody molecule, for use in this seventh aspect of the invention may bind specifically to tenascin-C large isoform. For example, the specific binding member may bind preferentially to tenascin-C large isoform relative to tenascin-C small isoform. Preferably, the specific binding member binds to the A1, A2, A3, A4, B and/or D domain of tenascin-C large isoform. Most preferably, the specific binding member binds to the A1 domain of tenascin-C.

The specific binding member, e.g. an antibody molecule, for use in this seventh aspect of the invention, may be conjugated to a detectable label, or a radioisotope.

In an eighth aspect, the invention provides a specific binding member that binds tenascin-C for use in a method of imaging endometriotic, psoriatic arthritic or psoriatic tissue. The invention also provides use of a specific binding member that binds tenascin-C for the manufacture of an imaging agent for imaging endometriotic, psoriatic arthritic or psoriatic tissue. The invention also provides a method of detecting or imaging endometriotic, psoriatic arthritic or psoriatic tissue in a human or animal, wherein the method comprises the steps of:

(a) administering to the human or animal a specific binding member which binds tenascin-C, and (b) detecting the binding of the specific binding member to endometriotic, psoriatic arthritic or psoriatic tissue in the human or animal body.

Preferably, the specific binding member binds human tenascin-C. The specific binding member, e.g. an antibody molecule, for use in this eighth aspect of the invention may bind specifically to tenascin-C large isoform. For example, the specific binding member may bind preferentially to tenascin-C large isoform relative to tenascin-C small isoform. Preferably, the specific binding member binds to the A1, A2, A3, A4, B and/or D domain of tenascin-C large isoform. Most preferably, the specific binding member binds to the A1 domain of tenascin-C.

The specific binding member, e.g. an antibody molecule, for use in this eighth aspect of the invention, may be conjugated to a detectable label, or a radioisotope.

A specific binding member for use in the invention may be an antibody which binds tenascin-C, and/or the A1, A2, A3, A4, B and/or D domain of the tenascin-C large isoform, wherein the antibody comprises one or more complementarity determining regions (CDRs) of antibody F16 or 4A1-F16 (Brack et al., 12, 3200-3208, (2006) Clin. Cancer Res.), or variants thereof.

A specific binding member for use in the invention may comprise a set of H and/or L CDRs of antibody F16 or 4A1-F16, or a set of H and/or L CDRs of antibody F16 or 4A1-F16 with ten or fewer, e.g. one, two, three, four, or five, amino acid substitutions within the disclosed set of H and/or L CDRs. Preferably, a specific binding member for use in the invention comprises a set of H and/or L CDRs of antibody F16 or 4A1-F16 with ten or fewer, e.g. one, two, three, four, or five, amino acid substitutions within the disclosed set of H and/or L CDRs. Preferably, a specific binding member for use in the invention comprises a set of H and/or L CDRs of antibody F16 or 4A1-F16 with ten or fewer, e.g. one, two, three, four, or five, amino acid substitutions within the disclosed set of H and/or L CDRs.

Substitutions may potentially be made at any residue within the set of CDRs, and may be within CDR1, CDR2 and/or CDR3.

For example, a specific binding member for use in the invention may comprise one or more CDRs as described herein, e.g. a CDR3, and optionally also a CDR1 and CDR2 to form a set of CDRs.

A specific binding member for use in the invention may also comprise an antibody molecule, e.g. a human antibody molecule. The specific binding member normally comprises an antibody VH and/or VL domain. VH domains of specific binding members are also provided for use in the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. The VH and VL domains and CDRs of antibody F16 and 4A1-F16 are described herein. All VH and VL sequences, CDR sequences, sets of CDRs and sets of HCDRs and sets of LCDRs disclosed herein represent embodiments of a specific binding member for use in the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

A specific binding member for use in the invention may comprise an antibody VH domain comprising complementarity determining regions HCDR1, HCDR2 and HCDR3 and a framework, wherein HCDR1 is SEQ ID NO: 52 or 54, and wherein optionally HCDR2 is SEQ ID NO: 58, and/or HCDR3 is SEQ ID NO: 62. Preferably, the HCDR1 is SEQ ID NO: 52.

Typically, a VH domain is paired with a VL domain to provide an antibody antigen-binding site, although as discussed further below, a VH or VL domain alone may be used to bind antigen. Thus, a specific binding member for use in the invention may further comprise an antibody VL domain comprising complementarity determining regions LCDR1, LCDR2 and LCDR3 and a framework, wherein LCDR1 is SEQ ID NO: 112, and wherein optionally LCDR2 is SEQ ID NO: 116, and/or LCDR3 is SEQ ID NO: 120.

A specific binding member for use in the invention may be an isolated antibody molecule for the A1 domain of tenascin-C, comprising a VH domain and a VL domain, wherein the VH domain comprises a framework and a set of complementarity determining regions HCDR1, HCDR2 and HCDR3 and wherein the VL domain comprises complementarity determining regions LCDR1, LCDR2 and LCDR3 and a framework, and wherein HCDR1 has amino acid sequence SEQ ID NO: 52 or 54;
HCDR2 has amino acid sequence SEQ ID NO: 58;
HCDR3 has amino acid sequence SEQ ID NO: 62;
LCDR1 has amino acid sequence SEQ ID NO: 112;
LCDR2 has amino acid sequence SEQ ID NO: 116; and
LCDR3 has amino acid sequence SEQ ID NO: 120.

One or more CDRs or a set of CDRs of an antibody may be grafted into a framework (e.g. human framework) to provide an antibody molecule for use in the invention. Framework regions may comprise human germline gene segment sequences. Thus, the framework may be germlined, whereby one or more residues within the framework are changed to match the residues at the equivalent position in the most similar human germline framework. A specific binding member for use in the invention may be an isolated antibody molecule having a VH domain comprising a set of HCDRs in a human germline framework, e.g. DP47. Normally the specific binding member also has a VL domain comprising a set of LCDRs, e.g. in a human germline framework. The human germline framework of the VL domain may be DPK22.

A VH domain for use in the invention may have amino acid sequence SEQ ID NO: 26 or 28. Preferably, the VH domain has the amino acid sequence SEQ ID NO: 26. A VL domain for use in the invention may have the amino acid SEQ ID NO: 88.

The VL domain of F16 and 4A1-F16 (SEQ ID NO: 88) may optionally include an extra glycine residue at its C-terminal end.

A specific binding member for use in the invention may be or comprise a single chain Fv (scFv), comprising a VH domain and a VL domain joined via a peptide linker. The skilled person may select an appropriate length and sequence of linker, e.g. at least 5 or at least 10 amino acids in length, up to about 15, up to about 20 or up to about 25 amino acids in length. The linker may have the amino acid sequence GSSGG (SEQ ID NO: 122).

The specific binding member may be a diabody, which is a multivalent or multispecific fragment constructed by gene fusion (WO94/13804; Holliger 1993a).

A single chain Fv (scFv) may be comprised within a mini-immunoglobulin or small immunoprotein (SIP), e.g. as described in (Li et al., 1997). An SIP may comprise an scFv molecule fused to the CH4 domain of the human IgE secretory isoform IgE-S2 ($\varepsilon_{s2}$-CH4; Batista et al., 1996) forming an homo-dimeric mini-immunoglobulin antibody molecule.

Alternatively, a specific binding member for use in the invention may comprise an antigen-binding site within a non-antibody molecule, normally provided by one or more CDRs e.g. a set of CDRs in a non-antibody protein scaffold. Specific binding members, including non-antibody and antibody molecules, are described in more detail elsewhere herein.

These and other aspects of the invention are described in further detail below.

BRIEF DESCRIPTION OF THE FIGURES

FIG. 2A shows staining with F8-SIP, which is an antibody molecule that binds ED-A, disclosed herein. FIG. 2B shows staining with L19-SIP, which is an antibody molecule that binds ED-B (e.g. Pini et al. 1998). FIG. 2C shows staining with F16-SIP, which is an antibody molecule that binds the A1 domain of Tenascin-C (WO2006/050834). FIG. 2D is a negative control in which no primary antibody was added.

FIG. 3A shows staining with F8-SIP, which is an antibody molecule that binds ED-A, disclosed herein. FIG. 3B shows staining with L19-SIP, which is an antibody molecule that binds ED-B (e.g. Pini et al. 1998). FIG. 3C shows staining with F16-SIP, which is an antibody molecule that binds the A1 domain of Tenascin-C (WO2006/050834). FIG. 3D is a negative control in which no primary antibody was added.

FIG. 4A shows staining with F8-SIP, which is an antibody molecule that binds ED-A, disclosed herein. FIG. 4B shows staining with L19-SIP, which is an antibody molecule that binds ED-B (e.g. Pini et al. 1998). FIG. 4C shows staining with F16-SIP, which is an antibody molecule that binds the A1 domain of Tenascin-C (WO2006/050834). FIG. 4D is a negative control in which no primary antibody was added.

FIG. 5A shows staining with F8-SIP, which is an antibody molecule that binds ED-A, disclosed herein.

FIG. 58 shows staining with L19-SIP, which is an antibody molecule that binds ED-B (e.g. Pini et al. 1998). FIG. 5C shows staining with F16-SIP, which is an antibody molecule that binds the A1 domain of Tenascin-C (WO2006/050834). FIG. 5D is a negative control in which no primary antibody was added.

FIG. 6A shows the nucleotide sequences of the anti-ED-A antibody F8 heavy chain (VH) (SEQ ID NO: 13) and its variant, F8 V5L VH (SEQ ID NO: 15). The nucleotide sequence of the heavy chain CDR1 (SEQ ID NO: 41) of anti-ED-A antibody F8 is underlined. The nucleotide sequence of the heavy chain CDR2 (SEQ ID NO: 55) of the anti-ED-A antibody F8 is shown in italics and underlined. The nucleotide sequence of the heavy chain CDR3 (SEQ ID NO: 59) of anti-ED-A antibody F8 is shown in bold and underlined.

FIG. 6B shows the nucleotide sequence of the anti-ED-A antibody F8 linker sequence (SEQ ID NO: 121).

FIG. 6C shows the nucleotide sequences of the anti-ED-A antibody F8 light chain (VL) (SEQ ID NO: 75) and its variant, F8 K18R VL (SEQ ID NO: 77). The nucleotide sequence of the light chain CDR1 (SEQ ID NO: 101) of anti-ED-A antibody F8 is underlined. The nucleotide sequence of the light chain CDR2 (SEQ ID NO: 113) of the anti-ED-A antibody F8 is shown in italics and underlined.

Figure 1:
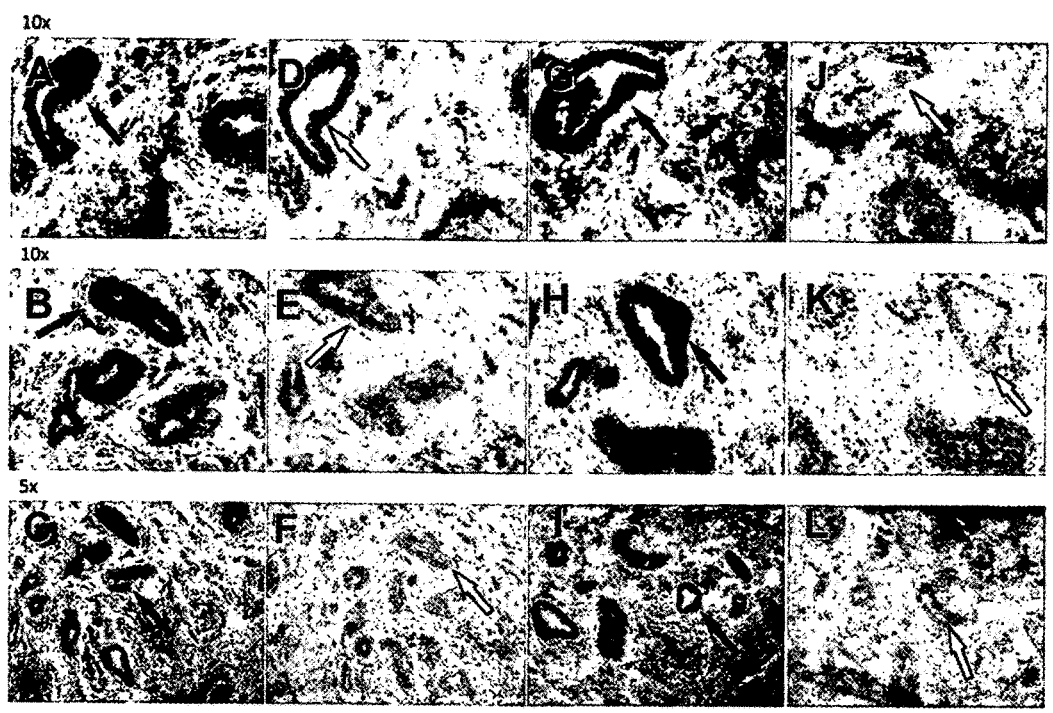
FIG. 1 shows the results of immunohistochemistry on samples from patients with endometriosis using antibodies directed to markers of angiogenesis. Darker staining indicates strong expression of the antigen, visualized by black arrows. Areas of negative staining around perivascular structures are indicated using white arrows. A, B and C show staining with F8-SIP, which is an antibody molecule that binds ED-A, disclosed herein. D, E and F show staining with L19-SIP, which is an antibody molecule that binds ED-B (e.g. Pini et al. 1998). G, H and I show staining with F16-SIP, which is an antibody molecule that binds the A1 domain of Tenascin-C (WO2006/050834). J, K and L are negative controls in which no primary antibody was added. A, D, G, J, B, E, H and K show samples viewed under 10× magnification and C, F, I and L show samples viewed under 5× magnification.

The nucleotide sequence of the light chain CDR3 (SEQ ID NO: 117) of anti-ED-A antibody F8 is shown in bold and underlined.

FIG. 7A shows the amino acid sequences of the anti-ED-A antibody F8 heavy chain (VH) (SEQ ID NO: 14), and its variant, F8 V5L VH (SEQ ID NO: 16). The amino acid sequence of the heavy chain CDR1 (SEQ ID NO: 42) of anti-ED-A antibody F8 is underlined. The amino acid sequence of the heavy chain CDR2 (SEQ ID NO: 56) of the anti-ED-A antibody F8 is shown in italics and underlined. The amino acid sequence of the heavy chain CDR3 (SEQ ID NO: 60) of anti-ED-A antibody F8 is shown in bold and underlined.

FIG. 7B shows the amino acid sequence of the anti-ED-A antibody F8 linker sequence (SEQ ID NO: 122).

FIG. 7C shows the amino acid sequences of the anti-ED-A antibody F8 light chain (VL) (SEQ ID NO: 76) and its variant, F8 K18R VL (SEQ ID NO: 78). The amino acid sequence of the light chain CDR1 (SEQ ID NO: 102) of anti-ED-A antibody F8 is underlined. The amino acid sequence of the light chain CDR2 (SEQ ID NO: 114) of the anti-ED-A antibody F8 is shown in italics and underlined. The amino acid sequence of the light chain CDR3 (SEQ ID NO: 118) of anti-ED-A antibody F8 is shown in bold and underlined.

FIG. 8A shows the nucleotide sequences of the heavy chain (VH) of the anti-tenascin-C antibody F16 (SEQ ID NO: 25) and its variant, 4A1-F16 (SEQ ID NO: 27). The nucleotide sequences of the heavy chain CDR1 of anti-tenascin-C antibodies F16 and F16-4A1 are underlined (SEQ ID NOs: 51 and 53 respectively). The nucleotide sequence of the heavy chain CDR2 (SEQ ID NO: 57) of the anti-tenascin-C antibodies F16 and F16-4A1 is shown in italics and underlined. The nucleotide sequence of the heavy chain CDR3 (SEQ ID NO: 61) of the anti-tenascin-C antibodies F16 and F16-4A1 is shown in bold and underlined.

FIG. 8B shows the nucleotide sequence of the linker sequence (SEQ ID NO: 121) of the anti-tenascin-C antibodies F16 and F16-4A1.

FIG. 8C shows the nucleotide sequence of the light chain (VL) (SEQ ID NO: 87) of the anti-tenascin-C antibodies F16 and F16-4A1. The nucleotide sequence of the light chain CDR1 (SEQ ID NO: 111) of the anti-tenascin-C antibodies F16 and F16-4A1 is underlined. The nucleotide sequence of the light chain CDR2 (SEQ ID NO: 115) of the anti-tenascin-C antibodies F16 and F16-4A1 is shown in italics and underlined. The nucleotide sequence of the light chain CDR3 (SEQ ID NO: 119) of anti-tenascin-C antibodies F16 and F16-4A1 is shown in bold and underlined.

FIG. 9A shows the amino acid sequence of the heavy chain (VH) of the anti-tenascin-C antibody F16 (SEQ ID NO: 26) and its variant, 4A1-F16 (SEQ ID NO: 28). The amino acid sequence of the heavy chain CDR1 of the anti-tenascin-C antibody F16 (SEQ ID NO: 52) and 4A1-F16 (SEQ ID NO: 54) is underlined. The amino acid sequence of the heavy chain CDR2 (SEQ ID NO: 58) of the anti-tenascin-C antibodies F16 and 4A1-F16 is shown in italics and underlined. The amino acid sequence of the heavy chain CDR3 (SEQ ID NO: 62) of anti-tenascin-C antibodies F16 and 4A1-F16 is shown in bold and underlined.

FIG. 9B shows the amino acid sequence of the anti-tenascin-C antibody F16 linker sequence (SEQ ID NO: 122).

FIG. 9C shows the amino acid sequence of the light chain (VL) (SEQ ID NO: 88) of the anti-tenascin-C antibodies F16 and 4A1-F16. The amino acid sequence of the light chain CDR1 (SEQ ID NO: 112) of anti-tenascin-C antibodies F16 and 4A1-F16 is underlined. The amino acid sequence of the light chain CDR2 (SEQ ID NO: 116) of the anti-tenascin-C antibodies F16 and 4A1-F16 is shown in italics and underlined. The amino acid sequence of the light chain CDR3 (SEQ ID NO: 120) of anti-tenascin-C antibodies F16 and 4A1-F16 is shown in bold and underlined.

Figure 10:
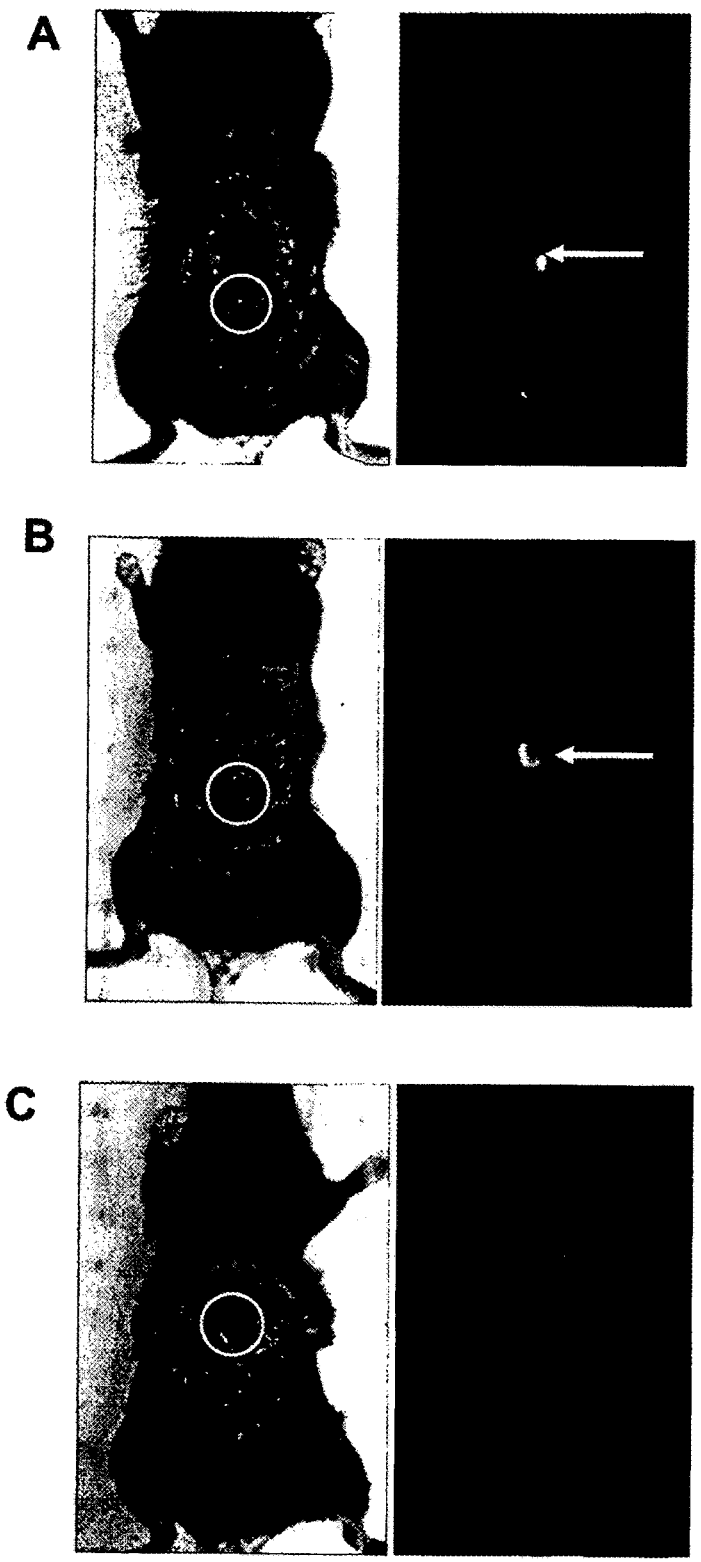

FIG. 10 shows the results of near infrared imaging of endometriosis lesions in mice. Areas of endometriosis in the mice are indicated by circles. FIGS. 10 A and B show the results of near infrared imaging using a SIP(F8)-ALEXA750 antibody molecule, which binds ED-A. SIP(F8)-ALEXA750 was injected into mice with endometriosis and imaged 24 h after injection. Arrows indicate areas of positive imaging. FIG. 10C shows the results of near-infrared imaging using a SIP(F16)-ALEXA750 antibody molecule which recognises the human A1 domain of tenascin-C. SIP(F16)-ALEXA750 was injected into mice with endometriosis and imaged 24 h after injection.

Figure 11:
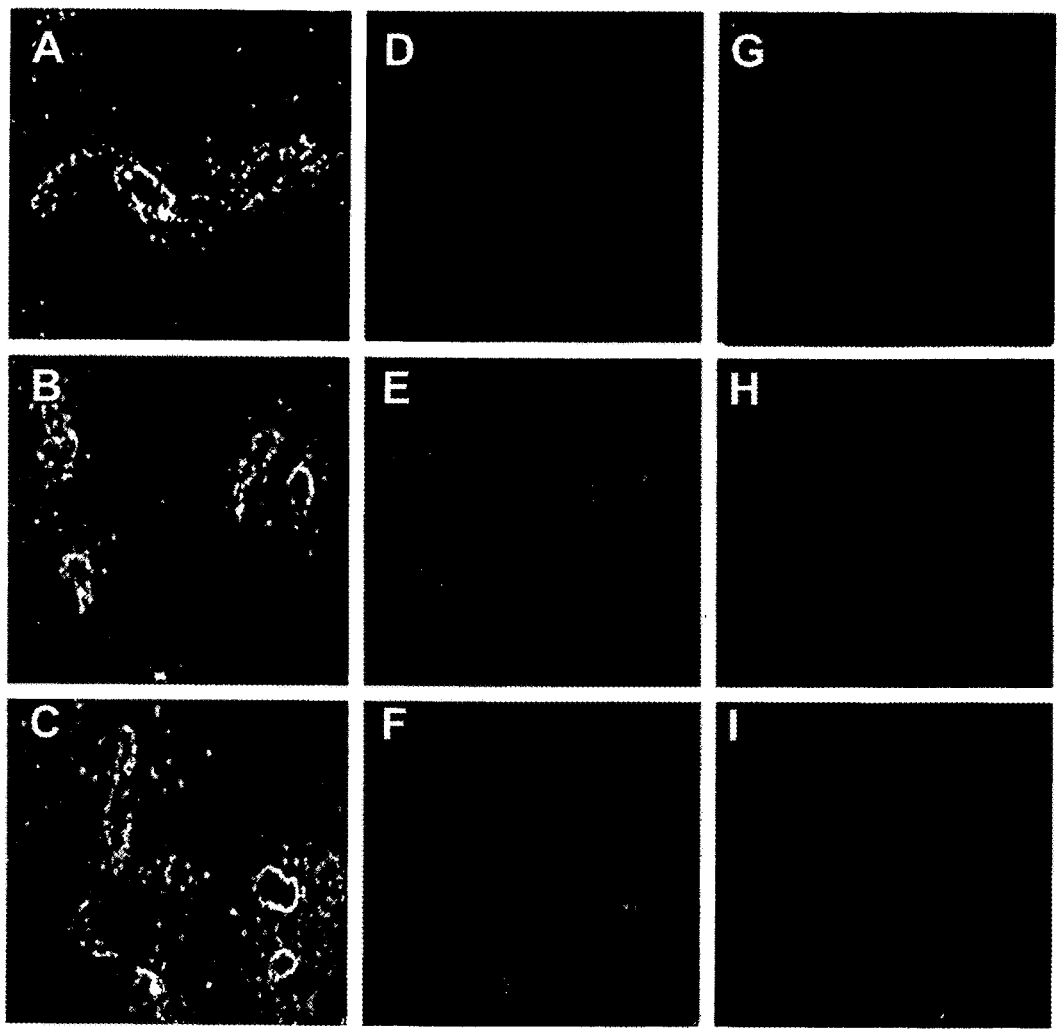

FIG. 11 shows the results of ex vivo staining of murine endometriosis lesions. FIGS. 11 A, B and C show immunofluorescent detection of SIP(F8)-ALEXA750 using a rabbit anti-human IgE antibody followed by goat anti-rabbit IgG. FIGS. 11 D, E and F show detection of blood vessels using a rat anti-CD31 antibody followed by donkey anti-rat IgG. FIGS. 11 G, H and I represent negative controls and show the results of probing the lesions with goat anti-rabbit IgG alone.

TERMINOLOGY

Fibronectin

Fibronectin is an antigen subject to alternative splicing, and a number of alternative isoforms of fibronectin are known, as described elsewhere herein. Extra Domain-A (EDA or ED-A) is also known as ED, extra type III repeat A (EIIIA) or EDI. The sequence of human ED-A has been published by Kornblihtt et al. (1984), Nucleic Acids Res. 12, 5853-5868 and Paolella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The sequence of mouse ED-A is available on the SwissProt database as amino acids 1721-1810 (Fibronectin type-III 13; extra domain 2) of the amino acid sequence deposited under accession number P11276.

The ED-A isoform of fibronectin (A-FN) contains the Extra Domain-A (ED-A). The sequence of the human A-FN can be deduced from the corresponding human fibronectin precursor sequence which is available on the SwissProt database under accession number P02751. The sequence of the mouse A-FN can be deduced from the corresponding mouse fibronectin precursor sequence which is available on the SwissProt database under accession number P11276. The A-FN may be the human ED-A isoform of fibronectin. The ED-A may be the Extra Domain-A of human fibronectin.

ED-A is a 90 amino acid sequence which is inserted into fibronectin (FN) by alternative splicing and is located between domain 11 and 12 of FN (Borsi et al., 1987, J. Cell Biol., 104, 595-600). ED-A is mainly absent in the plasma form of FN but is abundant during embryogenesis, tissue remodelling, fibrosis, cardiac transplantation and solid tumour growth.

Alternative Splicing

Alternative splicing refers to the occurrence of different patterns of splicing of a primary RNA transcript of DNA to produce different mRNAs. After excision of introns, selection may determine which exons are spliced together to form the mRNA. Alternative splicing leads to production of different isoforms containing different exons and/or different numbers of exons. For example one isoform may comprise an additional amino acid sequence corresponding to one or more exons, which may comprise one or more domains.

Tenascin-C

Tenascin-C is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumorigenesis or angiogenesis.

A strong over-expression of the large isoform of tenascin-C has been reported for a number of tumors [Borsi 1992 supra], and monoclonal antibodies specific for domains A1 and D, respectively, have been extensively characterised in the clinic [Riva et al., *Int J Cancer* (1992) 51:7-13; Riva et al., *Cancer Res* (1995), 55, 5952s-5956s; Paganelli et al., *Eur J Nucl Med* (1994) 21, 314-321. Reardon et al., *J Clin Oncol* (2002), 20, 1389-1397; Signer et al., *J Clin Oncol* (1998) 16, 2202-2212].

Human monoclonal antibody fragments specific to tenascin-C are described in WO2006/050834 and shown to bind preferentially to tumor tissue relative to normal tissue. These antibodies are useful, for example, in delivering toxins, such as cytokines, specifically to tumour cells.

Specific Binding Member

This describes one member of a pair of molecules that bind specifically to one another. The members of a specific binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A specific binding member normally comprises a molecule having an antigen-binding site. For example, a specific binding member may be an antibody molecule or a non-antibody protein that comprises an antigen-binding site.

An antigen binding site may be provided by means of arrangement of complementarity determining regions (CDRs) on non-antibody protein scaffolds such as fibronectin or cytochrome B etc. (Haan & Maggos, 2004; Koide 1998; Nygren 1997), or by randomising or mutating amino acid residues of a loop within a protein scaffold to confer binding specificity for a desired target. Scaffolds for engineering novel binding sites in proteins have been reviewed in detail by Nygren et al. (1997). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties such as an ability to enter cells, penetrate deep into tissues or reach targets within other structures, or to bind within protein cavities of the target antigen. Use of antigen binding sites in non-antibody scaffolds is reviewed in Wess, 2004. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain) and lipocalins. Other approaches include synthetic "Microbodies" (Selecore GmbH), which are based on cyclotides—small proteins having intra-molecular disulphide bonds.

In addition to antibody sequences and/or an antigen-binding site, a specific binding member for use in the present invention may comprise other amino acids, e.g. forming a peptide or polypeptide, such as a folded domain, or to impart to the molecule another functional characteristic in addition to ability to bind antigen. Binding members for use in the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat 1987, and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al. (1987), (Kabat 1991a, and later editions). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal 1974; Amit 1986; Chothia 1987; Chothia 1989; Caton 1990; Sharon 1990a; Sharon 1990b; Kabat et al., 1991b).

Antibody Molecule

This describes an immunoglobulin whether natural or partly or wholly synthetically produced. The term also relates to any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to, antibody molecules such as Fab, Fab', Fab'-SH, scFv, Fv, dAb, Fd; and diabodies.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel (2001). Phage display, another established technique for generating binding members has been described in detail in many publications such as WO92/01047 (discussed further below) and U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160, U.S. Pat. No. 6,521,404 and Kontermann & Dubel (2001). Transgenic mice in which the mouse antibody genes are inactivated and functionally replaced with human antibody genes while leaving intact other components of the mouse immune system, can be used for isolating human antibodies (Mendez 1997).

Synthetic antibody molecules may be created by expression from genes generated by means of oligonucleotides synthesized and assembled within suitable expression vectors, for example as described by Knappik et al. (2000) or Krebs et al. (2001).

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward 1989; McCafferty 1990; Holt 2003), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird 1988; Huston 1988); (viii) bispecific single chain Fv dimers (PCT/US92/09965) and (ix) "diabodies", multivalent or multispecific fragments constructed by gene fusion (WO94/13804; Holliger 1993a). Fv, scFv or diabody molecules may be stabilized by the incorporation of disulphide bridges linking the VH and VL domains (Reiter 1996). Minibodies comprising a scFv joined to a CH3 domain may also be made (Hu 1996). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Antibody fragments for use in the invention can be obtained starting from any of the antibody molecules described herein, e.g. antibody molecules comprising VH and/or VL domains or CDRs of any of antibodies described herein, by methods such as digestion by enzymes, such as pepsin or papain and/or by cleavage of the disulfide bridges by chemical reduction. In another manner, antibody fragments of the present invention may be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain (Holt 2003). VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A binding member of the present invention may be a dAb comprising a VH or VL domain substantially as set out herein, or a VH or VL domain comprising a set of CDRs substantially as set out herein.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions may be made in the CDR and/or VH or VL domain.

Bispecific or bifunctional antibodies form a second generation of monoclonal antibodies in which two different variable regions are combined in the same molecule (Holliger 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger 1993b), e.g. prepared chemically or from hybrid hybridomas, or may be any of the bispecific antibody fragments mentioned above. These antibodies can be obtained by chemical methods (Glennie 1987; Repp 1995) or somatic methods (Staerz 1986; Suresh 1986) but likewise by genetic engineering techniques which allow the heterodimerization to be forced and thus facilitate the process of purification of the antibody sought (Merchand 1998). Examples of bispecific antibodies include those of the BiTe™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against a target antigen, then a library can be made where the other arm is varied and an antibody of appropriate specificity selected. Bispecific whole antibodies may be made by alternative engineering methods as described in Ridgeway 1996.

Various methods are available in the art for obtaining antibodies against a target antigen. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane 1988) or to the technique of preparation from hybridomas described by Kohler and Milstein, 1975.

Monoclonal antibodies can be obtained, for example, from an animal cell immunized against A-FN or tenascin-C, or one of its fragments containing the epitope recognized by said monoclonal antibodies, e.g. a fragment comprising or consisting of ED-A or the A1, A2, A3, A4, B or D domain of the tenascin-C large isoform, or a peptide fragment of ED-A or the A1, A2, A3, A4, B or D domain of the tenascin-C large isoform. The A-FN or tenascin-C, or one of their fragments, can especially be produced according to the usual working methods, by genetic recombination starting with a nucleic acid sequence contained in the cDNA sequence coding for A-FN or tenascin-C, or fragment thereof, by peptide synthesis starting from a sequence of amino acids comprised in the peptide sequence of the A-FN or tenascin-C and/or fragment thereof.

Monoclonal antibodies can, for example, be purified on an affinity column on which A-FN or tenascin-C, or one of their fragments containing the epitope recognized by said monoclonal antibodies, e.g. a fragment comprising or consisting of ED-A or tenascin-C, or a peptide fragment of ED-A or tenascin-C, has previously been immobilized. Monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. The whole of these techniques may be used simultaneously or successively.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

Isolated

This refers to the state in which specific binding members for use in the invention or nucleic acid encoding such specific binding members, will generally be in accordance with the present invention. Thus, specific binding members, VH and/or VL domains of the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Specific binding members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising antibody molecules may also be used in the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

One or more specific binding members for an antigen, e.g. the A-FN, the tenascin-C, the ED-A of fibronectin, or the A1, A2, A3, A4, B or D domain of the tenascin-C large isoform may be obtained by bringing into contact a library of specific binding members according to the invention and the antigen or a fragment thereof, e.g. a fragment comprising or consisting of ED-A or tenascin-C, or a peptide fragment of ED-A or tenascin-C and selecting one or more specific binding members of the library able to bind the antigen.

An antibody library may be screened using Iterative Colony Filter Screening (ICFS). In ICFS, bacteria containing the DNA encoding several binding specificities are grown in a liquid medium and, once the stage of exponential growth has been reached, some billions of them are distributed onto a growth support consisting of a suitably pretreated membrane filter which is incubated until completely confluent bacterial colonies appear. A second trap substrate consists of another membrane filter, pre-humidified and covered with the desired antigen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments scFv having a spreading action, so that those fragments binding specifically with the antigen which is present on the trap membrane are trapped. The trap membrane is then treated to point out bound antibody fragments scFv with colorimetric techniques commonly used to this purpose.

The position of the coloured spots on the trap filter allows to go back to the corresponding bacterial colonies which are present on the growth membrane and produced the antibody fragments trapped. Such colonies are gathered and grown and the bacteria-a few millions of them are distributed onto a new culture membrane repeating the procedures described above. Analogous cycles are then carried out until the positive signals on the trap membrane correspond to single positive colonies, each of which represents a potential source of monoclonal antibody fragments directed against the antigen used in the selection. ICFS is described in e.g. WO0246455, which is incorporated herein by reference. A library may also be displayed on particles or molecular complexes, e.g. replicable genetic packages such bacteriophage (e.g. T7) particles, or other in vitro display systems, each particle or molecular complex containing nucleic acid encoding the antibody VH variable domain displayed on it, and optionally also a displayed VL domain if present. Phage display is described in WO92/01047 and e.g. U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160 and U.S. Pat. No. 6,521,404, each of which is herein incorporated by reference in its entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind the A-FN or the tenascin-C, or the ED-A of fibronectin or the A1, A2, A3, A4, B or D domain of the tenascin-C large isoform, or other target antigen or isoform may be further tested, e.g. ability to compete with e.g. any one of anti-ED-A antibodies H1, B2, C5, D5, E5, C8, F8, F1, B7, E8 or G9 for binding to the A-FN or a fragment of the A-FN, e.g. the ED-A of fibronectin, or an anti-tenascin-C antibody, such as F16 or 4A1-F16, for binding to the tenascin-C or a fragment of tenascin-C, e.g. the A1, A2, A3, A4, B or D domain of the tenascin-C large isoform.

A specific binding member for use in the invention may bind the A-FN and/or the ED-A of fibronectin, or tenascin-C and/or the A1, A2, A3, A4, B or D domain of the tenascin-C isoform specifically. A specific binding member of the present invention may bind the A-FN and/or the ED-A of fibronectin, or the tenascin-C, and/or the A1 domain of the tenascin-C large isoform, with the same affinity as an anti-ED-A antibody H1, B2, C5, D5, E5, C8, F8, F1, B7, E8 or G9, e.g. in scFv format, or as the anti-tenascin-C antibodies F16 or 4A1-F16, respectively, or with an affinity that is better. A specific binding member for use in the invention may bind the A-FN and/or the ED-A of fibronectin, or the tenascin-C and/or the A1, A2, A3, A4, B or D domain of the tenascin-C large isoform, with a $K_D$ of $3 \times 10^{-8}$ M or an affinity that is better. Preferably, a specific binding member for use in the invention binds the A-FN and/or the ED-A of fibronectin, or the tenascin-C and/or the A1, A2, A3, A4, B or D domain of the tenascin-C large isoform, with a $K_D$ of $2 \times 10^{-8}$ M or an affinity that is better. More preferably, a specific binding member for use in the invention binds the A-FN and/or the ED-A of fibronectin, or the tenascin-C and/or the A1, A2, A3, A4, B or D domain of the tenascin-C large isoform, with a $K_D$ of $1.7 \times 10^{-8}$ M or an affinity that is better. Yet more preferably, a specific binding member for use in the invention binds the A-FN and/or the ED-A of fibronectin, or the tenascin-C and/or the A1, A2, A3, A4, B or D domain of the tenascin-C large isoform, with a $K_D$ of $1.4 \times 10^{-8}$ M or an affinity that is better. Most preferably, a specific binding member for use in the invention binds the A-FN and/or the ED-A of fibronectin, or the tenascin-C and/or the A1, A2, A3, A4, B or D domain of the tenascin-C large isoform, with a $K_D$ of $3 \times 10^{-9}$ M or an affinity that is better.

A specific binding member of the present invention may bind to the same epitope on A-FN and/or the ED-A of fibronectin as one of the anti-ED-A antibodies H1, B2, C5, D5, E5, C8, F8, F1, B7, E8 or G9, or to the same epitope on tenascin-C, and/or the A1 domain of the tenascin-C large isoform, as the anti-tenascin-C antibody F16 or 4A1-F16.

A specific binding member for use in the invention may not show any significant binding to molecules other than to the A-FN and/or the ED-A of fibronectin, or to the tenascin-C and/or the A1, A2, A3, A4, B or D domain of the tenascin-C large isoform. In particular, the specific binding member may not bind other isoforms of fibronectin, for example the ED-B isoform and/or the IIICS isoform of fibronectin, or other isoforms of tenascin-C, for example the tenascin-C small isoform.

Variants of antibody molecules disclosed herein may be produced and used in the present invention. The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind A-FN and/or the ED-A of fibronectin, or tenascin-C and/or the A1, A2, A3, A4, B or D domain of the tenascin-C large isoform, and/or for any other desired property.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, may be 5, 4, 3, 2 or 1. Alterations may be made in one or more framework regions and/or one or more CDRs. The alterations normally do not result in loss of function, so a specific binding member comprising a thus-altered amino acid sequence may retain an ability to bind A-FN and/or the ED-A of fibronectin, or tenascin-C and/or the A1, A2, A3, A4, B or D domain of the tenascin-C large isoform. For example, it may retain the same quantitative binding as a specific binding member in which the alteration is not made, e.g. as measured in an assay described herein. The specific binding member comprising a thus-altered amino acid sequence may have an improved ability to bind A-FN and/or the ED-A of fibronectin, or tenascin-C and/or the A1, A2, A3, A4, B or D domain of the tenascin-C large isoform.

Novel VH or VL regions carrying CDR-derived sequences for use in the invention may be generated using random mutagenesis of one or more selected VH and/or VL genes to generate mutations within the entire variable domain. In some embodiments one or two amino acid substitutions are made within an entire variable domain or set of CDRs. Another method that may be used is to direct mutagenesis to CDR regions of VH or VL genes.

As noted above, a CDR amino acid sequence substantially as set out herein may be carried as a CDR in a human antibody variable domain or a substantial portion thereof. The HCDR3 sequences substantially as set out herein represent embodiments of the present invention and for example each of these may be carried as a HCDR3 in a human heavy chain variable domain or a substantial portion thereof.

Variable domains employed in the invention may be obtained or derived from any germ-line or rearranged human variable domain, or may be a synthetic variable domain based on consensus or actual sequences of known human variable domains. A variable domain can be derived from a non-human antibody. A CDR sequence for use in the invention (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members for use in the invention. The repertoire may then be displayed in a suitable host system such as the phage display system of WO92/01047, which is herein incorporated by reference in its entirety, or any of a subsequent large body of literature, including Kay, Winter & McCafferty (1996), so that suitable binding members may be selected. A repertoire may consist of from anything from $10^4$ individual members upwards, for example at least $10^9$, at least $10^6$, at least $10^7$, at least $10^8$, at least $10^9$ or at least $10^{10}$ members.

Similarly, one or more, or all three CDRs may be grafted into a repertoire of VH or VL domains that are then screened for a binding member or binding members for the A-FN and/or the ED-A of fibronectin, or the tenascin-C and/or the A1, A2, A3, A4, B or D domain of the tenascin-C large isoform.

One or more of the HCDR1, HCDR2 and HCDR3 of antibody H1, B2, C5, D5, E5, C8, F8, F1, B7, E8, G9, F16, or 4A1-F16, or the set of HCDRs of antibody H1, B2, C5, D5, E5, C8, F8, F1, B7, E8, G9, F16 or 4A1-F16 may be employed, and/or one or more of the LCDR1, LCDR2 and LCDR3 of antibody H1, B2, C5, D5, E5, C8, F8, F1, B7, E8, G9, F16, or 4A1-F16, or the set of LCDRs of antibody H1, B2, C5, D5, E5, C8, F8, F1, B7, E8, G9, F16 or 4A1-F16 may be employed.

Similarly, other VH and VL domains, sets of CDRs and sets of HCDRs and/or sets of LCDRs disclosed herein may be employed.

The A-FN and/or the ED-A of fibronectin, or the tenascin-C and/or the A1, A2, A3, A4, B or D domain of the tenascin-C large isoform, may be used in a screen for specific binding members, e.g. antibody molecules, for use in the preparation of a medicament for the treatment of endometriosis, psoriasis, or psoriatic arthritis. The screen may a screen of a repertoire as disclosed elsewhere herein.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains disclosed elsewhere herein to further protein sequences including antibody constant regions, other variable domains (for example in the production of diabodies) or detectable/functional labels as discussed in more detail elsewhere herein.

Although specific binding members may comprise a pair of VH and VL domains, single binding domains based on either VH or VL domain sequences may also be used in the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind A-FN and/or the ED-A of fibronectin, or tenascin-C, and/or the A1, A2, A3, A4, B or D domain of the tenascin-C large isoform. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques such as those described in that reference. This technique is also disclosed in Marks 1992.

Specific binding members for use in the present invention may further comprise antibody constant regions or parts thereof, e.g. human antibody constant regions or parts thereof. For example, a VL domain may be attached at its C-terminal end to antibody light chain constant domains including human Cκ or Cλ chains, e.g. Cλ. Similarly, a specific binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. Any synthetic or other constant region variant that has these properties and stabilizes variable regions is also useful in embodiments of the present invention.

Specific binding members for use in the invention may be labelled with a detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance. Detectable labels may be attached to antibodies for use in the invention using conventional chemistry known in the art.

There are numerous methods by which the label can produce a signal detectable by external means, for example, by visual examination, electromagnetic radiation, heat, and chemical reagents. The label can also be bound to another specific binding member that binds the antibody for use in the invention, or to a support.

Labelled specific binding members, e.g. scFv labelled with a detectable label, may be used diagnostically in vivo, ex vivo or in vitro, and/or therapeutically.

For example, radiolabelled binding members (e.g. binding members conjugated to a radioisotope) may be used in radiodiagnosis and radiotherapy. Radioisotopes which may be conjugated to a binding member for use in the invention include isotopes such as $^{94m}$Tc, $^{99m}$Tc, $^{186}$Re, $^{188}$Re, $^{203}$Pb, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Lu, $^{123}$I, $^{124}$I, $^{125}$I, $^{131}$I, $^{18}$F, $^{211}$At and $^{225}$Ac. Preferably, positron emitters, such as $^{18}$F and $^{124}$I, or gamma emitters, such as $^{99m}$Tc, $^{111}$In and $^{123}$I, are used for diagnostic applications (e.g. for PET), while beta-emitters, such as $^{131}$I, $^{90}$Y and $^{177}$Lu, are preferably used for therapeutic applications. Alpha-emitters, such as $^{211}$At and $^{225}$Ac may also be used for therapy.

For example, a specific binding member for use in the invention labelled with a detectable label may be used to detect, diagnose or monitor endometriosis, psoriasis, or psoriatic arthritis in a human or animal.

A specific binding member of the present invention may be used for the manufacture of a diagnostic product for use in diagnosing endometriosis, psoriasis, or psoriatic arthritis.

The present invention provides a method of detecting or diagnosing endometriosis, psoriasis, or psoriatic arthritis in a human or animal comprising:
  (a) administering to the human or animal a specific binding member of the present invention, for example labelled with a detectable label, which binds the ED-A isoform of fibronectin and/or the ED-A of fibronectin, or tenascin-C and/or the A1, A2, A3, A4, B and/or D domain of the tenascin-C large isoform, and
  (b) determining the presence or absence of the specific binding member in sites of endometriosis, psoriasis, or psoriatic arthritis of the human or animal body;

wherein localisation of the specific binding member to sites of endometriosis, psoriasis, or psoriatic arthritis indicates the presence of endometriosis, psoriasis, or psoriatic arthritis.

Where the binding member is labelled with a detectable label, the presence or absence of the detectable label may be determined by detecting the label.

A conjugate or fusion between a binding member for use in the invention and a molecule that exerts a biocidal, cytotoxic immunosuppressive or anti-inflammatory effect on target cells in the lesions and an antibody directed against an extracellular matrix component which is present in such lesions may be employed in the present invention. For example, the conjugated molecule may be inter alia interleukin-10, TGF-β, IL-2, IL-12, IL-15, IL-21, IL-24, IL-33, tumour necrosis factor (TNF), or interferon-α, -β or -γ, an anti-inflammatory or other drug, a photosensitizer or a radionuclide. Such conjugates may be used therapeutically, e.g. for treatment of endometriosis, psoriasis, or psoriatic arthritis as referred to herein.

Production and use of fusions or conjugates of specific binding members with biocidal or cytotoxic molecules is described for example in WO01/62298, which is incorporated by reference herein.

The invention provides a method of treating endometriosis, psoriasis, or psoriatic arthritis, the method comprising administering to an individual a therapeutically effective amount of a medicament comprising a specific binding member for use in the invention.

The specific binding member for use in the invention may be a conjugate of (i) a molecule which exerts an anti-inflammatory effect on target cells by cellular interaction, an anti-inflammatory molecule, a cytokine e.g. IL-10, TGF-β, IL-2, IL-12, IL-15, IL-21, IL-24, IL-33, tumour necrosis factor (TNF), interferon-α, -β or -γ, or other drug, and (ii) a specific binding member for the ED-A isoform of fibronectin and/or the ED-A of fibronectin, or tenascin-C, and/or the A1, A2, A3, A4, B and/or D domain of the tenascin-C large isoform.

The specific binding member for use in the invention may be a conjugate of (i) a molecule which exerts an immunosuppressive or anti-inflammatory effect and (ii) a specific binding member for the ED-A isoform of fibronectin and/or the ED-A of fibronectin, or tenascin-C, and/or the A1, A2, A3, A4, B and/or D domain of the tenascin-C large isoform.

The specific binding member for use in the invention may be a conjugate of (i) interleukin-10 (IL10) or TGF beta and (ii) a specific binding member for the ED-A isoform of fibronectin and/or the ED-A of fibronectin, or tenascin-C, and/or the A1, A2, A3, A4, B and/or D domain of the tenascin-C large isoform. Such a specific binding member is useful in aspects of the invention disclosed herein relating to treatment of endometriosis, psoriasis and psoriatic arthritis.

The invention provides the use of a specific binding member as described herein for the preparation of a medicament for the treatment of endometriosis, psoriasis and psoriatic arthritis.

The specific binding member for use in the invention may be a conjugated or fused to a molecule that exerts a biocidal, cytotoxic, immunosuppressive or anti-inflammatory effect as described herein. The specific binding member for use in the invention may be a conjugate of (i) a molecule which exerts a biocidal or cytotoxic effect on target cells by cellular interaction or has an immunosuppressive or anti-inflammatory effect and (ii) a specific binding member for the ED-A isoform of fibronectin and/or the ED-A of fibronectin, or tenascin-C, and/or the A1, A2, A3, A4, B and/or D domain of the tenascin-C large isoform.

Also described herein is a conjugate of (i) a molecule which exerts a biocidal or cytotoxic effect on target cells by cellular interaction, or an immunosuppressive or anti-inflammatory effect and (ii) a binding member for the ED-A isoform of fibronectin and/or the ED-A of fibronectin, or tenascin-C, and/or the A1, A2, A3, A4, B and/or D domain of the tenascin-C large isoform. Such a conjugate preferably comprises a fusion protein comprising the biocidal, cytotoxic, immunosuppressive or anti-inflammatory molecule and a said binding member, or, where the binding member is two-chain or multi-chain, a fusion protein comprising the biocidal, cytotoxic, immunosuppressive or anti-inflammatory molecule and a polypeptide chain component of said binding member. Preferably the binding member is a single-chain polypeptide, e.g. a single-chain antibody molecule, such as scFv.

A fusion protein comprising the immunosuppressive or anti-inflammatory molecule and a single-chain Fv antibody molecule may be used in the invention.

The immunosuppressive or anti-inflammatory molecule that exerts its effect on target cells by cellular interaction, may interact directly with the target cells, may interact with a membrane-bound receptor on the target cell or perturb the electrochemical potential of the cell membrane. Preferably, the molecule is IL-10 or TGF-β.

Examples of other molecules which can be conjugated to the specific binding member include IL-2, IL-12, IL-15, IL-21, IL-24, IL-33, tumour necrosis factor (TNF), or interferon-α, -β or -γ.

As discussed further below, the specific binding member for use in the invention is preferably an antibody molecule or comprises an antibody antigen-binding site. Conveniently, the specific binding member may be a single-chain polypeptide, such as a single-chain antibody. This allows for convenient production of a fusion protein comprising single-chain antibody and, for example, immunosuppressive or anti-inflammatory molecule (e.g. interleukin-10 or TGF beta). An antibody antigen-binding site may be provided by means of association of an antibody VH domain and an antibody VL domain in separate polypeptides, e.g. in a complete antibody or in an antibody fragment such as Fab or diabody. Where the specific binding member is a two-chain or multi-chain molecule (e.g. Fab or whole antibody, respectively), an immunosuppressive or anti-inflammatory molecule, for example, may be conjugated as a fusion polypeptide with one or more polypeptide chains in the specific binding member.

The specific binding member may be conjugated with the immunosuppressive or anti-inflammatory molecule by means of a peptide bond, i.e. within a fusion polypeptide comprising said molecule and the specific binding member or a polypeptide chain component thereof (see e.g. Trachsel et al.). Other means for conjugation include chemical conjugation, especially cross-linking using a bifunctional reagent (e.g. employing DOUBLE-REAGENTS™ Cross-linking Reagents Selection Guide, Pierce).

Also described herein is isolated nucleic acid encoding a specific binding member for use in the present invention. Nucleic acid may include DNA and/or RNA. A nucleic acid may code for a CDR or set of CDRs or VH domain or VL domain or antibody antigen-binding site or antibody molecule, e.g. scFv or IgG, e.g. IgG1, as defined above. The nucleotide sequences may encode the VH and/or VL domains disclosed herein.

Further described herein are constructs in the form of plasmids, vectors, transcription or expression cassettes which comprise at least one polynucleotide as described above.

A recombinant host cell that comprises one or more constructs as above are also described. A nucleic acid encoding any CDR or set of CDRs or VH domain or VL domain or antibody antigen-binding site or antibody molecule, e.g. scFv or IgG1 or IgG4 as provided, is described, as is a method of production of the encoded product, which method comprises expression from encoding nucleic acid. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

A nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A method of production of an antibody VH variable domain, the method including causing expression from encoding nucleic acid is also described. Such a method may comprise culturing host cells under conditions for production of said antibody VH variable domain.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun 1991. A common bacterial host is E. coli.

Expression in eukaryotic cells in culture is also available to those skilled in the art as an option for production of a specific binding member for example Chadd & Chamow (2001), Andersen & Krummen (2002), Larrick & Thomas (2001). Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001). Many known techniques and protocols for manipulation of nucleic acid, for example in preparation of nucleic acid constructs, mutagenesis, sequencing, introduction of DNA into cells and gene expression, and analysis of proteins, are described in detail in Ausubel 1999.

A host cell may contain a nucleic acid as described herein. Such a host cell may be in vitro and may be in culture. Such a host cell may be in vivo. In vivo presence of the host cell may allow intracellular expression of a binding member for use in the present invention as "intrabodies" or intracellular antibodies. Intrabodies may be used for gene therapy.

A method comprising introducing a nucleic acid disclosed herein into a host cell is also described. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

The nucleic acid may be integrated into the genome (e.g. chromosome) of the host cell. Integration may be promoted by inclusion of sequences that promote recombination with the genome, in accordance with standard techniques.

A method that comprises using a construct as stated above in an expression system in order to express a specific binding member or polypeptide as above is also described.

Specific binding members for use in the present invention are designed to be used in methods of diagnosis or treatment in human or animal subjects, e.g. human. Specific binding members for use in the invention may be used in diagnosis or treatment of endometriosis, psoriasis and psoriatic arthritis.

Accordingly, the invention provides methods of treatment comprising administration of a specific binding member as described, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient. Pharmaceutically acceptable vehicles are well known and will be adapted by the person skilled in the art as a function of the nature and of the mode of administration of the active compound(s) chosen.

Specific binding members for use in the present invention will usually be administered in the form of a pharmaceutical composition, which may comprise at least one component in addition to the specific binding member. Thus, pharmaceutical compositions described herein, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled or by injection, e.g. intravenous.

Pharmaceutical compositions for oral administration such as for example nanobodies etc are also envisaged in the present invention. Such oral formulations may be in tablet, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson, 1978.

A composition may be administered alone or in combination with other treatments, concurrently or sequentially or as a combined preparation with another therapeutic agent or agents, dependent upon the condition to be treated.

A specific binding member for use in the present invention may be used as part of a combination therapy in conjunction with an additional medicinal component. Combination treatments may be used to provide significant synergistic effects, particularly the combination of a specific binding member for use in the present invention with one or more other drugs. A specific binding member for use in the present invention may be administered concurrently or sequentially or as a combined preparation with another therapeutic agent or agents, for the treatment of one or more of the conditions listed herein.

For example, a specific binding member for use in the invention may be used in combination with an existing therapeutic agent for the treatment of endometriosis, psoriasis or psoriatic arthritis.

A specific binding member for use in the invention and one or more of the above additional medicinal components may be used in the manufacture of a medicament. The medicament may be for separate or combined administration to an individual, and accordingly may comprise the specific binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration may be in a "therapeutically effective amount", this being sufficient to show benefit to a patient. Such benefit may be at least amelioration of at least one symptom. Thus "treatment of endometriosis, psoriasis or psoriatic arthritis" refers to amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of specific binding member, the method of administration, the scheduling of administration and other factors known to medical practitioners. Prescription of treatment, e.g. decisions on dosage etc, is within the responsibility of general practitioners and other medical doctors, and may depend on the severity of the symptoms and/or progression of a disease being treated. Appropriate doses of antibody are well known in the art (Ledermann 1991 and Bagshawe 1991. Specific dosages indicated herein, or in the Physician's Desk Reference (2003) as appropriate for the type of medicament being administered, may be used. A therapeutically effective amount or suitable dose of a specific binding member for use in the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody), and the nature of any detectable label or other molecule attached to the antibody. A typical antibody dose will be in the range 100 µg to 1 g for systemic applications, and 1 µg to 1 mg for topical applications. An initial higher loading dose, followed by one or more lower doses, may be administered. An antibody may be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of, the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

Further aspects and embodiments of the invention will be apparent to those skilled in the art given the present disclosure including the following experimental exemplification.

EXPERIMENTAL

Results
Histochemical Analysis of Human Endometriotic Specimens

Expression of fibronectin domains ED-A and ED-B and the A1 domain of the tenascin-C large isoform was investigated by immunohistochemistry on human endometriotic specimens using biotinylated F8-, L19- and F16-SIP antibodies respectively. The results of the immunohistochemical analysis are shown in FIG. 1.

In FIG. 1 darker staining indicates expression of the respective antigens (indicated with black arrows).

Both the ED-A of fibronectin (recognised by the biotinylated F8-SIP antibody) and the A1 domain of tenascin-C (recognised by the biotinylated F16-SIP antibody) were strongly expressed around the perivascular structures of biopsies of human endometriotic specimens (see FIGS. 1 A,B&C for staining with F8-SIP and FIGS. 1 G,H&I for staining with F16-SIP). The intense staining of vascular structures with F16-SIP was stronger than observed with F8-SIP. No staining is visible for the negative control, i.e. the same type of endometriotic specimen incubated with the streptavidin reagent, but without any primary antibody (see FIGS. 1 J,K&L).

The ED-B domain of fibronectin (recognised by the biotinylated L19-SIP antibody) was only weakly positive (see FIGS. 1 D,E&F).

Histochemical Analysis of Human Ulcerative Colitic Specimens

Expression of fibronectin domains ED-A and ED-B, and the A1 domain of the tenascin-C large isoform were investigated by immunohistochemistry on human ulcerative colitic specimens using biotinylated F8-, L19- and F16-SIP antibodies respectively. The results of the immunohistochemical analysis are shown in FIG. 2.

Figure 2:
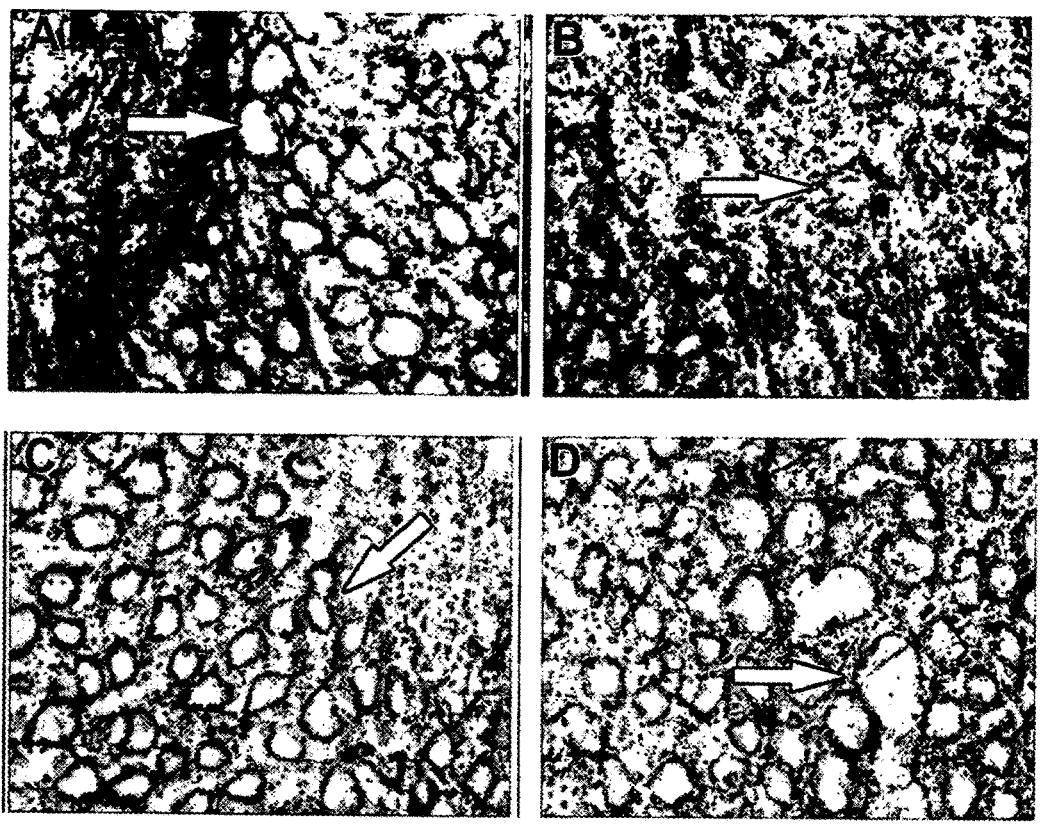
FIG. 2 shows the results of immunohistochemistry on samples from patients with ulcerative colitis using antibodies directed to markers of angiogenesis. The white arrows indicate areas of negative staining around perivascular structures.

In FIG. 2, areas of negative staining around perivascular structures are indicated using white arrows.

Immunohistochemical analysis of human ulcerative colitic samples revealed virtually negative staining for all three antibodies, F8, L19 and F16 (see FIGS. 2A,B&C respectively). Only a weak positivity was observed with F8-SIP in some specimens.

Histochemical Analysis of Human Psoriatic Arthritic Specimens

Expression of fibronectin domains ED-A and ED-B, and the A1 domain of the tenascin-C large isoform were investigated by immunohistochemistry on human psoriatic arthritic specimens using biotinylated F8-, L19- and F16-SIP antibodies respectively. The results of the immunohistochemical analysis are shown in FIG. 3.

Figure 3:
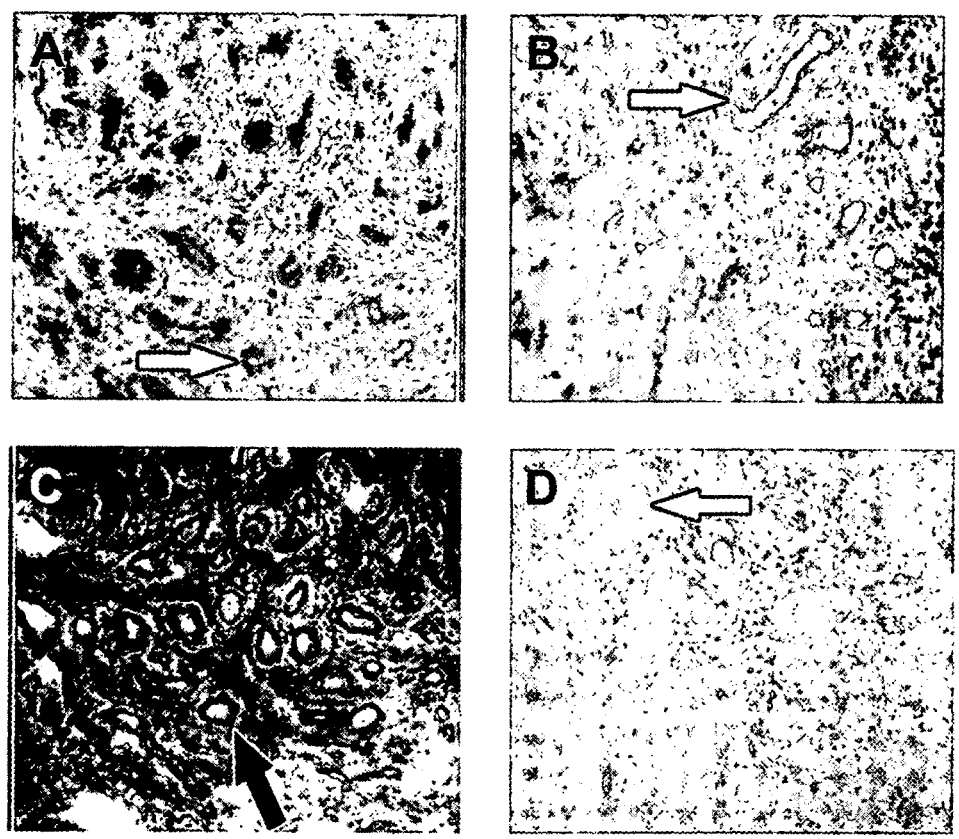
FIG. 3 shows the results of immunohistochemistry on samples from patients with psoriatic arthritis using antibodies directed to markers of angiogenesis. Darker staining indicates strong expression of the antigen, visualized by black arrows. Areas of negative staining around perivascular structures are indicated using white arrows.

In FIG. 3, darker staining indicates expression of the respective antigens (indicated with black arrows).

The A1 domain of tenascin-C (recognised by the biotinylated F16-SIP antibody) was strongly expressed around the perivascular structures of biopsies of human psoriatic arthritic specimens, i.e. very intense staining was observed (see FIG. 3C). No staining was visible for the negative control nor for the ED-B domain of fibronectin (recognised by the biotinylated L19-SIP antibody) or the ED-A domain of fibronectin (recognised by the biotinylated F8-SIP antibody) (see FIGS. 3 A, B and D respectively).

Histochemical Analysis of Samples from Patients with Multiple Sclerosis

Expression of fibronectin domains ED-A and ED-B, and the A1 domain of the tenascin-C large isoform were investigated by immunohistochemistry on samples from patients with multiple sclerosis using biotinylated F8-, L19- and F16-SIP antibodies respectively. The results of the immunohistochemical analysis are shown in FIG. 4.

Figure 4:
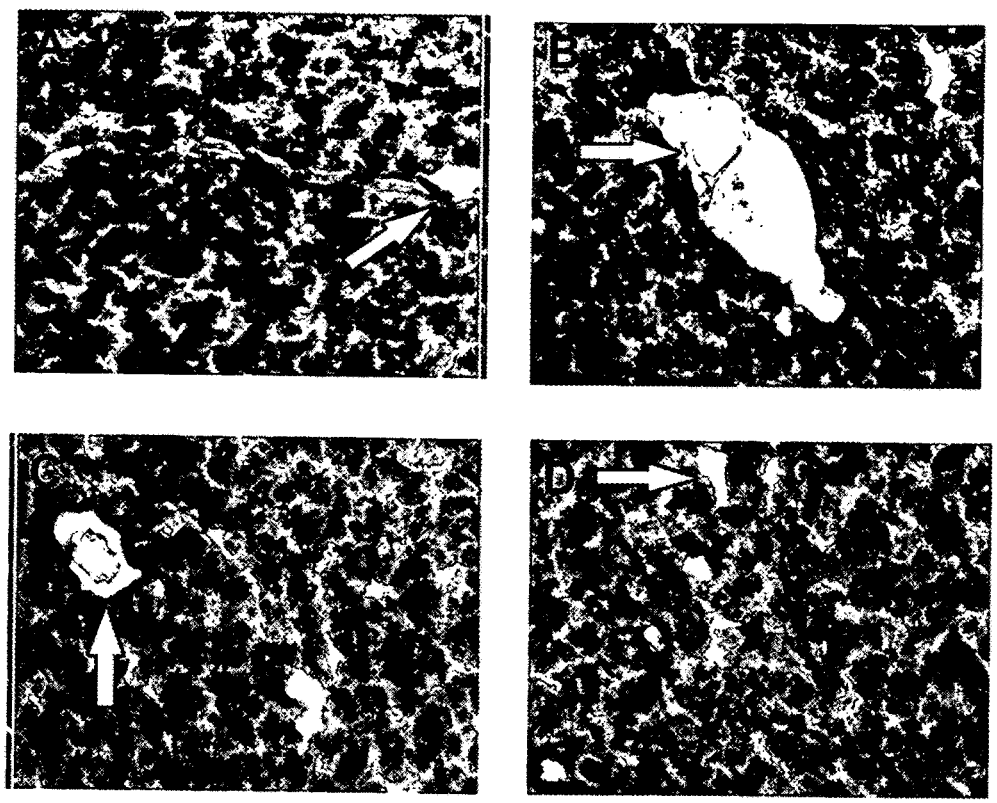
FIG. 4 shows the results of immunohistochemistry on samples from patients with multiple sclerosis using antibodies directed to markers of angiogenesis. The white arrows indicate areas of negative staining around perivascular structures.

In FIG. 4, areas of negative staining around perivascular structures are indicated using white arrows.

Immunohistochemical analysis of tissue sections from pathological specimens from patients with multiple sclerosis revealed only extremely weak positivity at vascular structures for L19, F8 and F16 (see FIGS. 4 A,B&C).

Histochemical Analysis of Samples from Patients with Psoriasis

Expression of fibronectin domains ED-A and ED-B, and the A1 domain of the tenascin-C large isoform were investigated by immunohistochemistry on samples from patients with psoriasis using biotinylated F8-, L19- and F16-SIP antibodies respectively. The results of the immunohistochemical analysis are shown in FIG. 5.

Figure 5:
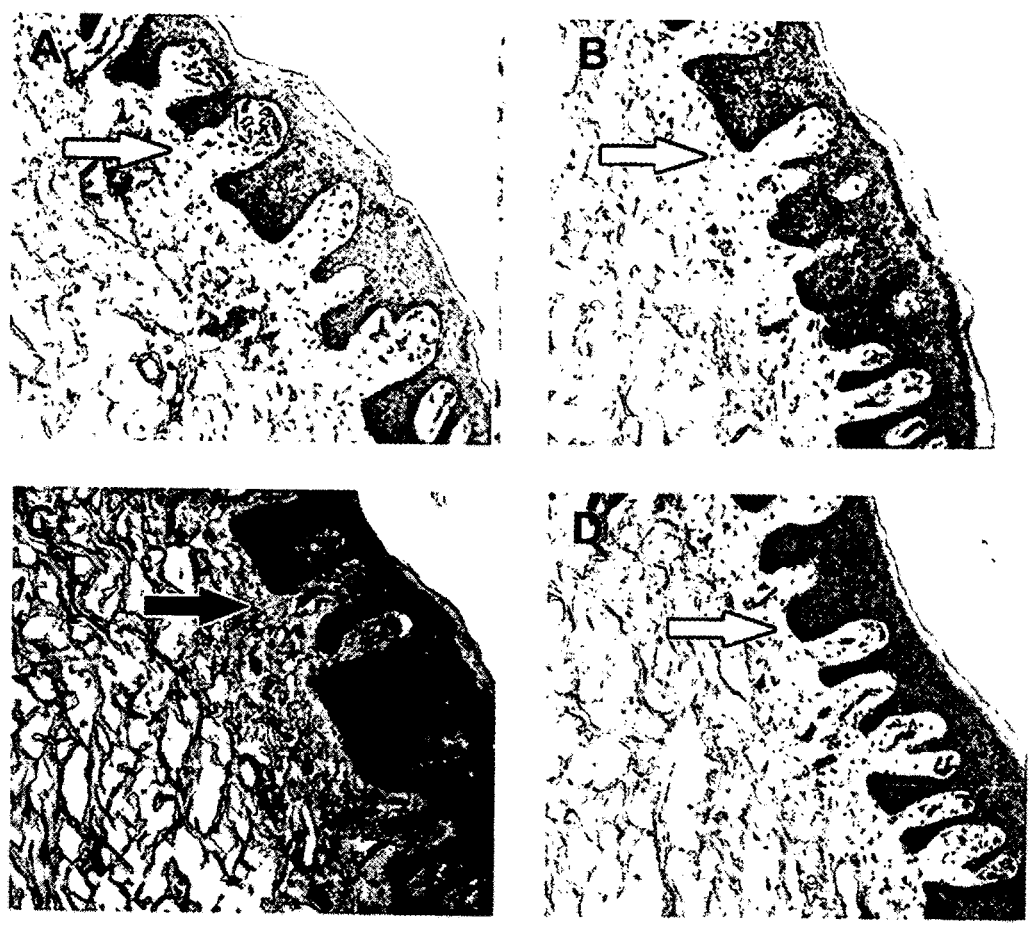
FIG. 5 shows the results of immunohistochemistry on samples from patients with psoriasis using antibodies directed to markers of angiogenesis. Darker staining indicates strong expression of the antigen, visualized by black arrows. Areas of negative staining around perivascular structures are indicated using white arrows.

In FIG. 5, darker staining indicates expression of the respective antigens (indicated with black arrows).

The A1 domain of tenascin-C (recognised by the biotinylated F16-SIP antibody) was strongly expressed around the perivascular structures of biopsies of human psoriatic specimens, i.e. very intense staining was observed (see FIG. 5C). No staining was visible for the negative control nor for the ED-B domain of fibronectin (recognised by the biotinylated L19-SIP antibody) or the ED-A domain of fibronectin (recognised by the biotinylated F8-SIP antibody) (see FIGS. 5 D, B and A respectively).

Based on the findings described above, expression of ED-A and the tenascin-C large isoform is not found in all angiogenesis-related diseases. Endometriosis is particularly suited for pharmacodelivery using anti-ED-A antibody molecules, while endometriosis, psoriasis and psoriatic arthritis are particularly suited for pharmacodelivery using anti-tenascin-C antibody molecules.

Near Infrared Imaging of Endometriotic Lesions in Mice

A mouse model of endometriosis was generated as described below. The selective accumulation of F8-SIP in mice with endometriosis was tested by near infrared imaging analysis, as described by Birchler et al. [Birchler et al., J Immunological Methods 1999, 231, 239-248]. F8-SIP and F16-SIP were labeled using Alexa750 (Molecular Probes), according to the manufacturer's recommendations, and injected into the tail vein of endometriosis mice. Mice were sacrificed and imaged in a near infrared mouse imager 24 hours after injection. F16-SIP was used as a negative control as it recognises the human A1 domain of tenascin-C but not the murine antigen.

As shown in FIGS. 10 A and B, SIP(F8)-ALEXA750 accumulates on the endometriotic lesions (indicated by arrows), whereas SIP(F16)-ALEXA750 does not (FIG. 10C), thus confirming the in vivo specificity of F8-SIP.

Ex Vivo Detection of SIP(F8)-ALEXA750

As soon as the near infrared imaging was completed, endometriotic lesions were removed from sacrificed animals, embedded in cryoembedding compound (Microm, Walldorf, Germany) and stored at −80° C. Sections (10 μm) were then cut and fixed in acetone. SIP(F8)-ALEXA750 was detected using a rabbit anti-human IgE antibody (Dako, Glostrup, Denmark), followed by Alexa Fluor 488 goat anti-rabbit IgG (Molecular Probes, Leiden, The Netherlands). For the detection of blood vessels, double staining with a rat anti-CD31 antibody followed by Alexa Fluor 594 donkey anti-rat IgG was performed. As a negative control, the specimen was probed with Alexa Fluor 488 goat anti-rabbit IgG minus the human IgE antibody.

The results clearly show correspondence between the blood vessels (see brighter areas in FIGS. 11 D, E and F) and staining with SIP(F8)-ALEXA750 (see brighter areas in FIGS. 11 A, B and C). These results confirm that SIP(F8)-ALEXA750 had accumulated around vascular structures during the imaging studies.

These data show the first successful attempt at in vivo imaging of endometriosis without the need for laparoscopy, or other form of surgery.

Materials and Methods

Immunohistochemistry with Biotinylated SIP Antibodies

The tissue sections were fixed in cold acetone (−20° C.) for 10 minutes and the slides were dried at room temperature for 30 minutes. Silicon was applied using a pen and the slides were then immersed in TBS (50 mM Tris, 100 mM NaCl, pH 7.4, 0.01% aprotinin) for 5 minutes. The slides were dried with paper without touching the sections. The sections were blocked with 20% fetal calf serum (FCS) in TBS for 30 minutes. The blocking solution was then removed and the slides were submerged in TBS for 5 minutes. The primary biotinylated antibody in SIP format was diluted in TBS/3% BSA to a final concentration of 1.6 µg/ml and applied to the sections for 60 minutes at room temperature. The slides were washed twice with TBS+2 mM $MgCl_2$ (406 mg/l) (2×5 minutes). The back of the slides were dried with paper and SAP-complex 1:150 (Biopsa F014-62) in TBS+2 mM $MgCl_2$/3% BSA for 60 minutes at room temperature. The sections were washed three times with TBS+2 mM $MgCl_2$ (3×5 minutes). The substrate (made up by dissolving 1 Tris and 1 FastRed tablet per 1 ml MilliQ water) was added and incubated on the sections for 10 minutes. The sections were washed twice with deionised water (2×2 minutes) and transferred to Gill's hematoxylin solution no. 2 for 2 minutes. The slides were quickly transferred to de-ionised water and rinsed with water for 5 minutes. The slides were allowed to dry and mounted with glycerol and visualised with an optical microscope (Zeiss Axiovert 5100 TV).

Mouse Model of Endometriosis 6-8 week old C57BL/6 mice were subjected to ovariectomy 7 days prior to induction of endometriosis. Mice were anesthesized by isoflurane in combination with carprofen (Rimadyl). After ovariectomy, mice were oestrogen-treated (3×/week 4 ug estradiol/mouse in a volume of 100 ul arachis oil subcutaneously injected, starting at the day of transplantation). Ovariectomy plus oestrogen supplementation was done in order to abrogate differences related to the stage of the oestrous cycle. At day 0, mice were split into 2 groups: donor mice (33%) and recipient mice (66%). Donor mice were killed and both uterine horns were removed and subsequently placed in a sterile Petri dish containing sterile saline. Endometrium was detached from the uterine muscle and finley chopped using a scalpel. Endometrial fragments were suspended in saline and injected into the peritoneal cavity of the receipient mice. 4 weeks after transplantation, mice were used for near infrared imaging.

TABLE 1

Nucleotide sequences of the heavy chains (VH) of anti-ED-A and anti-tenascin C antibodies. VH CDR1 sequences are underlined; VH CDR2 sequences are in italics and underlined; VH CDR 3 sequences are in bold and underlined.

| Antibody | VH domain |
|---|---|
| H1 | GAGGTGCAGCTGGTGGAGTCTGGGGGAGGCTTGGTACAGCCTGGGGGGTC<br>CCTGAGACTCTCCTGTGCAGCCTCTGGATTCACCTTTAGCCCGCGGAGGATG<br>AGCTGGGTCCGCCAGGCTCCAGGGAAGGGGCTGGAGTGGGTCTCAGCTATT<br>AGTGGTAGTGGTGGTAGCACATACTACGCAGACTCCGTGAAGGGCCGGTTC<br>ACCATCTCCAGAGACAATTCCAAGAACACGCTGTATCTGCAAATGAACAGCCT<br>GAGAGCCGAGGACACGGCCGTATATTACTGTGCGAAAGTACTCATTTGTAT<br>CTTTTTGACTACTGGGGCCAGGGAACCCTGGTCACCGTCTCGAGT<br>(SEQ ID NO: 1) |
| B2 | GAGGTGCAGCTGGTGGAGTCTGGGGGAGGCTTGGTACAGCCTGGGGGGTC<br>CCTGAGACTCTCCTGTGCAGCCTCTGGATTCACCTTTAGCGCGGCTAAGATG<br>AGCTGGGTCCGCCAGGCTCCAGGGAAGGGGCTGGAGTGGGTCTCAGCTATT<br>AGTGGTAGTGGTGGTAGCACATACTACGCAGACTCCGTGAAGGGCCGGTTC |

TABLE 1-continued

Nucleotide sequences of the heavy chains (VH) of anti-ED-A and anti-tenascin C antibodies. VH CDR1 sequences are underlined; VH CDR2 sequences are in italics and underlined; VH CDR 3 sequences are in bold and underlined.

| Antibody | VH domain |
|---|---|
|  | ACCATCTCCAGAGACAATTCCAAGAACACGCTGTATCTGCAAATGAACAGCCT<br>GAGAGCCGAGGACACGGCCGTATATTACTGTGCGAAAAGTACTCATTTGTAT<br>CTTTTTGACTACTGGGGCCAGGGAACCCTGGTCACCGTCTCGAGT<br>(SEQ ID NO: 3) |
| C5 | GAGGTGCAGCTGGTGGAGTCTGGGGGAGGCTTGGTACAGCCTGGGGGGTC<br>CCTGAGACTCTCCTGTGCAGCCTCTGGATTCACCTTTAGC<u>CCGATTAC</u>TATGA<br>GCTGGGTCCGCCAGGCTCCAGGGAAGGGGCTGGAGTGGGTCTCAGCTATT<u>A</u><br><u>*GTGGTAGTGGTGGTAGC*</u>ACATACTACGCAGACTCCGTGAAGGGCCGGTTCA<br>CCATCTCCAGAGACAATTCCAAGAACACGCTGTATCTGCAAATGAACAGCCT<br>GAGAGCCGAGGACACGGCCGTATATTACTGTGCGAAAAGTACTCATTTGTAT<br>CTTTTTGACTACTGGGGCCAGGGAACCCTGGTCACCGTCTCGAGT<br>(SEQ ID NO: 5) |
| D5 | GAGGTGCAGCTGGTGGAGTCTGGGGGAGGCTTGGTACAGCCTGGGGGGTC<br>CCTGAGACTCTCCTGTGCAGCCTCTGGATTCACCTTTAGC<u>GTGATGAAG</u>ATG<br>AGCTGGGTCCGCCAGGCTCCAGGGAAGGGGCTGGAGTGGGTCTCAGCTATT<br><u>*AGTGGTAGTGGTGGTAGC*</u>ACATACTACGCAGACTCCGTGAAGGGCCGGTTC<br>ACCATCTCCAGAGACAATTCCAAGAACACGCTGTATCTGCAAATGAACAGCCT<br>GAGAGCCGAGGACACGGCCGTATATTACTGTGCGAAAAGTACTCATTTGTAT<br>CTTTTTGACTACTGGGGCCAGGGAACCCTGGTCACCGTCTCGAGT<br>(SEQ ID NO: 7) |
| E5 | GAGGTGCAGCTGGTGGAGTCTGGGGGAGGCTTGGTACAGCCTGGGGGGTC<br>CCTGAGACTCTCCTGTGCAGCCTCTGGATTCACCTTTAGC<u>ACTGGTTCT</u>ATGA<br>GCTGGGTCCGCCAGGCTCCAGGGAAGGGGCTGGAGTGGGTCTCAGCTATT<u>A</u><br><u>*GTGGTAGTGGTGGTAGC*</u>ACATACTACGCAGACTCCGTGAAGGGCCGGTTCA<br>CCATCTCCAGAGACAATTCCAAGAACACGCTGTATCTGCAAATGAACAGCCT<br>GAGAGCCGAGGACACGGCCGTATATTACTGTGCGAAAAGTACTCATTTGTAT<br>CTTTTTGACTACTGGGGCCAGGGAACCCTGGTCACCGTCTCGAGT<br>(SEQ ID NO: 9) |
| C8 | GAGGTGCAGCTGGTGGAGTCTGGGGGAGGCTTGGTACAGCCTGGGGGGTC<br>CCTGAGACTCTCCTGTGCAGCCTCTGGATTCACCTTTAGC<u>CTTCAGAC</u>TATGA<br>GCTGGGTCCGCCAGGCTCCAGGGAAGGGGCTGGAGTGGGTCTCAGCTATT<u>A</u><br><u>*GTGGTAGTGGTGGTAGC*</u>ACATACTACCAGACTCCGTGAAGGGCCGGTTCA<br>CCATCTCCAGAGACAATTCCAAGAACACGCTGTATCTGCAAATGAACAGCCT<br>GAGAGCCGAGGACACGGCCGTATATTACTGTGCGAAAAGTACTCATTTGTAT<br>CTTTTTGACTACTGGGGCCAGGGAACCCTGGTCACCGTCTCGAGT<br>(SEQ ID NO: 11) |
| F8 VH | GAGGTGCAGCTGGTGGAGTCTGGGGGAGGCTTGGTACAGCCTGGGGGGTC<br>CCTGAGACTCTCCTGTGCAGCCTCTGGATTCACCTTTAGC<u>CTGTTTACG</u>ATGA<br>GCTGGGTCCGCCAGGCTCCAGGGAAGGGGCTGGAGTGGGTCTCAGCTATT<u>A</u><br><u>*GTGGTAGTGGTGGTAGC*</u>ACATACTACGCAGACTCCGTGAAGGGCCGGTTCA<br>CCATCTCCAGAGACAATTCCAAGAACACGCTGTATCTGCAAATGAACAGCCT<br>GAGAGCCGAGGACACGGCCGTATATTACTGTGCGAAAAGTACTCATTTGTAT<br>CTTTTTGACTACTGGGGCCAGGGAACCCTGGTCACCGTCTCGAGT<br>(SEQ ID NO: 13) |
| F8 VH V5L | GAGGTGCAGCTGTTGGAGTCTGGGGGAGGCTTGGTACAGCCTGGGGGGTC<br>CCTGAGACTCTCCTGTGCAGCCTCTGGATTCACCTTTAGC<u>CTGTTTACG</u>ATGA<br>GCTGGGTCCGCCAGGCTCCAGGGAAGGGGCTGGAGTGGGTCTCAGCTATT<u>A</u><br><u>*GTGGTAGTGGTGGTAGC*</u>ACATACTACGCAGACTCCGTGAAGGGCCGGTTCA<br>CCATCTCCAGAGACAATTCCAAGAACACGCTGTATCTGCAAATGAACAGCCT<br>GAGAGCCGAGGACACGGCCGTATATTACTGTGCGAAAAGTACTCATTTGTAT<br>CTTTTTGACTACTGGGGCCAGGGAACCCTGGTCACCGTCTCGAGT<br>(SEQ ID NO: 15) |
| F1 | GAGGTGCAGCTGGTGGAGTCTGGGGGAGGCTTGGTACAGCCTGGGGGGTC<br>CCTGAGACTCTCCTGTGCAGCCTCTGGATTCACCTTTAGC<u>TAGGCGCGT</u>ATG<br>AGCTGGGTCCGCCAGGCTCCAGGGAAGGGGCTGGAGTGGGTCTCAGCTATT<br><u>*AGTGGTAGTGGTGGTAGC*</u>ACATACTACGCAGACTCCGTGAAGGGCCGGTTC<br>ACCATCTCCAGAGACAATTCCAAGAACACGCTGTATCTGCAAATGAACAGCCT<br>GAGAGCCGAGGACACGGCCGTATATTACTGTGCGAAAAGTACTCATTTGTAT<br>CTTTTTGACTACTGGGGCCAGGGAACCCTGGTCACCGTCTCGAGT<br>(SEQ ID NO: 17) |
| B7 | GAGGTGCAGCTGGTGGAGTCTGGGGGAGGCTTGGTACAGCCTGGGGGGTC<br>CCTGAGACTCTCCTGTGCAGCCTCTGGATTCACCTTTAGC<u>CATTTTGATA</u>TGA<br>GCTGGGTCCGCCAGGCTCCAGGGAAGGGGCTGGAGTGGGTCTCAGCTATT<u>A</u><br><u>*GTGGTAGTGGTGGTAGC*</u>ACATACTACGCAGACTCCGTGAAGGGCCGGTTCA<br>CCATCTCCAGAGACAATTCCAAGAACACGCTGTATCTGCAAATGAACAGCCT |

TABLE 1-continued

Nucleotide sequences of the heavy chains (VH) of anti-ED-A and anti-tenascin C antibodies. VH CDR1 sequences are underlined; VH CDR2 sequences are in italics and underlined; VH CDR 3 sequences are in bold and underlined.

| Antibody | VH domain |
|---|---|
| | GAGAGCCGAGGACACGGCCGTATATTACTGTGCGAAAAGTACTCATTTGTATCTTTTTGACTACTGGGGCCAGGGAACCCTGGTCACCGTCTCGAGT<br>(SEQ ID NO: 19) |
| E8 | GAGGTGCAGCTGGTGGAGTCTGGGGGAGGCTTGGTACAGCCTGGGGGGTCCCTGAGACTCTCCTGTGCAGCCTCTGGATTCACCTTTAGC<u>GATATGCAT</u>ATGAGCTGGGTCCGCCAGGCTCCAGGGAAGGGGCTGGAGTGGGTCTCAGCTATT<u>*A*</u><u>*GTGGTAGTGGTGGTAGC*</u>ACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAAAGTACTCATTTGTATCTTTTTGACTACTGGGGCCAGGGAACCCTGGTCACCGTCTCGAGT<br>(SEQ ID NO: 21) |
| G9 | GAGGTGCAGCTGGTGGAGTCTGGGGGAGGCTTGGTACAGCCTGGGGGGTCCCTGAGACTCTCCTGTGCAGCCTCTGGATTCACCTTTAGC<u>CATATGCAG</u>ATGAGCTGGGTCCGCCAGGCTCCAGGGAAGGGGCTGGAGTGGGTCTCAGCTATT<u>*A*</u><u>*GTGGTAGTGGTGGTAGC*</u>ACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAAAGTACTCATTTGTATCTTTTTGACTACTGGGGCCAGGGAACCCTGGTCACCGTCTCGAGT<br>(SEQ ID NO: 23) |
| F16 | GAGGTGCAGCTGTTGGAGTCTGGGGGAGGCTTGGTACAGCCTGGGGGGTCCCTGAGACTCTCCTGTGCAGCCTCTGGATTCACCTTTAGC<u>CGGTATGGTATG</u><u>AGC</u>TGGGTCCGCCAGGCTCCAGGGAAGGGGCTGGAGTGGGTCTC<u>*AGCTATT*</u><u>*AGTGGTAGTGGTGGTAGCACATACTACGCAGACTCCGTGAAGGGC*</u>CGGTTCACCATCTCCAGAGACAATTCCAAGAACACGCTGTATCTGCAAATGAACAGCCTGAGAGCCGAGGACACGGCCGTATATTACTGTGCGAAAGCGCATAATGCTTTTGACTACTGGGGCCAGGGAACCCTGGTCACCGTGTCGAGA<br>(SEQ ID NO: 25) |
| 4A1-F16 | GAGGTGCAGCTGTTGGAGTCTGGGGGAGGCTTGGTACAGCCTGGGGGGTCCCTGAGACTCTCCTGTGCAGCCTCTGGATTCACCTTTAGC<u>CGGTATGGTGCG</u><u>AGC</u>TGGGTCCGCCAGGCTCCAGGGAAGGGGCTGGAGTGGGTCTCA<u>*GCTATT*</u><u>*AGTGGTAGTGGTGGTAGCACATACTACGCAGACTCCGTGAAGGGC*</u>CGGTTCACCATCTCCAGAGACAATTCCAAGAACACGCTGTATCTGCAAATGAACAGCCTGAGAGCCGAGGACACGGCCGTATATTACTGTGCGAAAGCGCATAATGCTTTTGACTACTGGGGCCAGGGAACCCTGGTCACCGTGTCGAGA<br>(SEQ ID NO: 27) |

TABLE 2

Amino acid sequences of the heavy chains (VH) of anti-ED-A and anti-tenascin C antibodies. VH CDR1 sequences are underlined; VH CDR2 sequences are in italics and underlined; VH CDR 3 sequences are in bold and underlined.

| Antibody | VH domain |
|---|---|
| H1 | EVQLVESGGGLVQPGGSLRLSCAASGFTFS<u>PRRM</u>SWVRQAPGKGLEWVSAI<u>*SG*</u><u>*SGGS*</u>TYYADSVKGRFTISRDNSKNTLYLQMNSLRAEDTAVYYCAKSTHLYLFDYWGQGTLVTVSS<br>(SEQ ID NO: 2) |
| B2 | EVQLVESGGGLVQPGGSLRLSCAASGFTFS<u>AAKM</u>SWVRQAPGKGLEWVSAI<u>*SG*</u><u>*SGGS*</u>TYYADSVKGRFTISRDNSKNTLYLQMNSLRAEDTAVYYCAKSTHLYLFDYWGQGTLVTVSS<br>(SEQ ID NO: 4) |
| C5 | EVQLVESGGGLVQPGGSLRLSCAASGFTFS<u>PITM</u>SWVRQAPGKGLEWVSAI<u>*SG*</u><u>*SGGS*</u>TYYADSVKGRFTISRDNSKNTLYLQMNSLRAEDTAVYYCAKSTHLYLFDYWGQGTLVTVSS<br>(SEQ ID NO: 6) |
| D5 | EVQLVESGGGLVQPGGSLRLSCAASGFTFS<u>VMKM</u>SWVRQAPGKGLEWVSAI<u>*SG*</u><u>*SGGS*</u>TYYADSVKGRFTISRDNSKNTLYLQMNSLRAEDTAVYYCAKSTHLYLFDWGQGTLVTVSS<br>(SEQ ID NO: 8) |

TABLE 2-continued

Amino acid sequences of the heavy chains (VH) of anti-ED-A and anti-tenascin C antibodies. VH CDR1 sequences are underlined; VH CDR2 sequences are in italics and underlined; VH CDR 3 sequences are in bold and underlined.

| Antibody | VH domain |
|---|---|
| E5 | EVQLVESGGGLVQPGGSLRLSCAASGFTFS<u>TGS</u>MSWVRQAPGKGLEWVSAI<u>*SG SGGS*</u>TYYADSVKGRFTISRDNSKNTLYLQMNSLRAEDTAVYYCAK<u>STHLY</u>LFDW GQGTLVTVSS (SEQ ID NO: 10) |
| C8 | EVQLVESGGGLVQPGGSLRLSCAASGFTFS<u>LQT</u>MSWVRQAPGKGLEWVSAI<u>*SG SGGS*</u>TYYADSVKGRFTISRDNSKNTLYLQMNSLRAEDTAVYYCAK<u>STHLYL</u>FDY WGQGTLVTVSS (SEQ ID NO: 12) |
| F8 VH | EVQLVESGGGLVQPGGSLRLSCAASGFTFS<u>LFT</u>MSWVRQAPGKGLEWVSAI<u>*SG SGGS*</u>TYYADSVKGRFTISRDNSKNTLYLQMNSLRAEDTAVYYCAK<u>STHLYL</u>FDY WGQGTLVTVSS (SEQ ID NO: 14) |
| F8 VH V5L | EVQLLESGGGLVQPGGSLRLSCAASGFTFS<u>LFT</u>MSWVRQAPGKGLEWVSAI<u>*SG SGGS*</u>TYYADSVKGRFTISRDNSKNTLYLQMNSLRAEDTAVYYCAK<u>STHLYL</u>FDY WGQGTLVTVSS (SEQ ID NO: 16) |
| F1 | EVQLVESGGGLVQPGGSLRLSCAASGFTFS<u>QAR</u>MSWVRQAPGKGLEWVSAI<u>*SG SGGS*</u>TYYADSVKGRFTISRDNSKNTLYLQMNSLRAEDTAVYYCAK<u>STHLYL</u>FDY WGQGTLVTVSS (SEQ ID NO: 18) |
| B7 | EVQLVESGGGLVQPGGSLRLSCAASGFTFS<u>HFD</u>MSWVRQAPGKGLEWVSAI<u>*SG SGGS*</u>TYYADSVKGRFTISRDNSKNTLYLQMNSLRAEDTAVYYCAK<u>STHLYL</u>FDY WGQGTLVTVSS (SEQ ID NO: 20) |
| E8 | EVQLVESGGGLVQPGGSLRLSCAASGFTFS<u>DMH</u>MSWVRQAPGKGLEWVSAI<u>*S GSGGS*</u>TYYADSVKGRFTISRDNSKNTLYLQMNSLRAEDTAVYYCAK<u>STHLYL</u>FD YWGQGTLVTVSS (SEQ ID NO: 22) |
| G9 | EVQLVESGGGLVQPGGSLRLSCAASGFTFS<u>HMQ</u>MSWVRQAPGKGLEWVSAI<u>*S GSGGS*</u>TYYADSVKGRFTISRDNSKNTLYLQMNSLRAEDTAVYYCAK<u>STHLYL</u>FD YWGQGTLVTVSS (SEQ ID NO: 24) |
| F16 | EVQLLESGGGLVQPGGSLRLSCAASGFTFS<u>RYG</u>MSWVRQAPGKGLEWVSAI<u>*SG SGGSTYYADSVKG*</u>RFTISRDNSKNTLYLQMNSLRAEDTAVYYCAK<u>AHNAFDY</u>W GQGTLVTVSR (SEQ ID NO: 26) |
| 4A1-F16 | EVQLLESGGGLVQPGGSLRLSCAASGFTFS<u>RYGAS</u>WVRQAPGKGLEWVSAI<u>*SG SGGSTYYADSVKG*</u>RFTISRIDNISKNTLYLQMNSLRAEDTAVYYCAK<u>AHNAFDY</u>W GQGTLVTVSR (SEQ ID NO: 28) |

TABLE 3

Nucleotide sequences of the light chains (VL) of anti-ED-A and anti-tenascin C antibodies. VL CDR1 sequences are underlined; VL CDR2 sequences are in italics and underlined; VL CDR 3 sequences are in bold and underlined.

| Antibody | VL domain |
|---|---|
| H1 | GAAATTGTGTTGACGCAGTCTCCAGGCACCCTGTCTTTGTCTCCAGGGGAAA AAGCCACCCTCTCCTGCAGGGCCAGTCAGAGTGTTAGC<u>TCTGCGTGGTTAGC</u> CTGGTACCAGCAGAAACCTGGCCAGGCTCCCAGGCTCCTCATCTAT<u>*GGTGCA TCCAGCAGGGCCACT*</u>GGCATCCAGACAGGTTCAGTGGCAGTGGGTCTGGG ACAGACTTCACTCTCACCATCAGCAGACTGGAGCCTGAAGATTTTGCAGTGTA TTACTGTCAGCAG<u>ATGCGTGGTCGGCCGCCG</u>ACGTTCGGCCAAGGGACCAA GGTGGAAATCAAA (SEQ ID NO: 63) |
| B2 | GAAATTGTGTTGACGCAGTCTCCAGGCACCCTGTCTTTGTCTCCAGGGGAAA AAGCCACCCTCTCCTGCAGGGCCAGTCAGAGTGTTAGC<u>GTGGCTTTTT</u>TAGC |

TABLE 3-continued

Nucleotide sequences of the light chains (VL) of anti-ED-A and anti-tenascin C antibodies. VL CDR1 sequences are underlined; VL CDR2 sequences are in italics and underlined; VL CDR 3 sequences are in bold and underlined.

| Antibody | VL domain |
|---|---|
|  | CTGGTACCAGCAGAAACCTGGCCAGGCTCCCAGGCTCCTCATCTAT*GGTGCA* *TCCAGCAGGGCCACT*GGCATCCCAGACAGGTTCAGTGGCAGTGGGTCTGGG ACAGACTTCACTCTCACCATCAGCAGACTGGAGCCTGAAGATTTTGCAGTGTA TTACTGTCAGCAGATGCGTGGTCGGCCGCCGACGTTCGGCCAAGGGACCAA GGTGGAAATCAAA (SEQ ID NO: 65) |
| C5 | GAAATTGTGTTGACGCAGTCTCCAGGCACCCTGTCTTTGTCTCCAGGGGAAA AAGCCACCCTCTCCTGCAGGGCCAGTCAGAGTGTTAGC<u>TTGCATTTTT</u>TAGC CTGGTACCAGCAGAAACCTGGCCAGGCTCCCAGGCTCCTCATCTAT*GGTGCA* *TCCAGCAGGGCCACT*GGCATCCCAGACAGGTTCAGTGGCAGTGGGTCTGGG ACAGACTTCACTCTCACCATCAGCAGACTGGAGCCTGAAGATTTTGCAGTGTA TTACTGTCAGCAGATGCGTGGTCGGCCGCCGACGTTCGGCCAAGGGACCAA GGTGGAAATCAAA (SEQ ID NO: 67) |
| D5 | GAAATTGTGTTGACGCAGTCTCCAGGCACCCTGTCTTTGTCTCCAGGGGAAA AAGCCACCCTCTCCTGCAGGGCCAGTCAGAGTGTTAGC<u>AATGCTTTTT</u>TAGC CTGGTACCAGCAGAAACCTGGCCAGGCTCCCAGGCTCCTCATCTAT*GGTGCA* *TCCAGCAGGGCCACT*GGCATCCCAGACAGGTTCAGTGGCAGTGGGTCTGGG ACAGACTTCACTCTCACCATCAGCAGACTGGAGCCTGAAGATTTTGCAGTGTA TTACTGTCAGCAGATGCGTGGTCGGCCGCCGACGTTCGGCCAAGGGACCAA GGTGGAAATCAAA (SEQ ID NO: 69) |
| E5 | GAAATTGTGTTGACGCAGTCTCCAGGCACCCTGTCTTTGTCTCCAGGGGAAA AAGCCACCCTCTCCTGCAGGGCCAGTCAGAGTGTTAGC<u>CTTGCGCATT</u>TAGC CTGGTACCAGCAGAAACCTGGCCAGGCTCCCAGGCTCCTCATCTAT*GGTGCA* *TCCAGCAGGGCCACT*GGCATCCCAGACAGGTTCAGTGGCAGTGGGTCTGGG ACAGACTTCACTCTCACCATCAGCAGACTGGAGCCTGAAGATTTTGCAGTGTA TTACTGTCAGCAGATGCGTGGTCGGCCGCCGACGTTCGGCCAAGGGACCAA GGTGGAAATCAAA (SEQ ID NO: 71) |
| C8 | GAAATTGTGTTGACGCAGTCTCCAGGCACCCTGTCTTTGTCTCCAGGGGAAA AAGCCACCCTCTCCTGCAGGGCCAGTCAGAGTGTTAGC<u>CTTCCTTTTT</u>TAGC CTGGTACCAGCAGAAACCTGGCCAGGCTCCCAGGCTCCTCATCTAT*GGTGCA* *TCCAGCAGGGCCACT*GGCATCCCAGACAGGTTCAGTGGCAGTGGGTCTGGG ACAGACTTCACTCTCACCATCAGCAGACTGGAGCCTGAAGATTTTGCAGTGTA TTACTGTCAGCAGATGCGTGGTCGGCCGCCGACGTTCGGCCAAGGGACCAA GGTGGAAATCAAA (SEQ ID NO: 73) |
| F8 VL | GAAATTGTGTTGACGCAGTCTCCAGGCACCCTGTCTTTGTCTCCAGGGGAAA AAGCCACCCTCTCCTGCAGGGCCAGTCAGAGTGTTAGC<u>ATGCCGTTTT</u>TAGC CTGGTACCAGCAGAAACCTGGCCAGGCTCCCAGGCTCCTCATCTAT*GGTGCA* *TCCAGCAGGGCCACT*GGCATCCCAGACAGGTTCAGTGGCAGTGGGTCTGGG ACAGACTTCACTCTCACCATCAGCAGACTGGAGCCTGAAGATTTTGCAGTGTA TTACTGTCAGCAGATGCGTGGTCGGCCGCCGACGTTCGGCCAAGGGACCAA GGTGGAAATCAAA (SEQ ID NO: 75) |
| F8 VL K18R | GAAATTGTGTTGACGCAGTCTCCAGGCACCCTGTCTTTGTCTCCAGGGGAAA GAGCCACCCTCTCCTGCAGGGCCAGTCAGAGTGTTAGC<u>ATGCCGTTTT</u>TAGC CTGGTACCAGCAGAAACCTGGCCAGGCTCCCAGGCTCCTCATCTAT*GGTGCA* *TCCAGCAGGGCCACT*GGCATCCCAGACAGGTTCAGTGGCAGTGGGTCTGGG ACAGACTTCACTCTCACCATCAGCAGACTGGAGCCTGAAGATTTTGCAGTGTA TTACTGTCAGCAGATGCGTGGTCGGCCGCCGACGTTCGGCCAAGGGACCAA GGTGGAAATCAAA (SEQ ID NO: 77) |
| F1 | GAAATTGTGTTGACGCAGTCTCCAGGCACCCTGTCTTTGTCTCCAGGGGAAA AAGCCACCCTCTCCTGCAGGGCCAGTCAGAGTGTTAGC<u>GCGCCTTTTT</u>TAGC CTGGTACCAGCAGAAACCTGGCCAGGCTCCCAGGCTCCTCATCTAT*GGTGCA* *TCCAGCAGGGCCACT*GGCATCCCAGACAGGTTCAGTGGCAGTGGGTCTGGG ACAGACTTCACTCTCACCATCAGCAGACTGGAGCCTGAAGATTTTGCAGTGTA TTACTGTCAGCAGATGCGTGGTCGGCCGCCGACGTTCGGCCAAGGGACCAA GGTGGAAATCAAA (SEQ ID NO: 79) |
| B7 | GAAATTGTGTTGACGCAGTCTCCAGGCACCCTGTCTTTGTCTCCAGGGGAAA AAGCCACCCTCTCCTGCAGGGCCAGTCAGAGTGTTAGC<u>CTGGCTTTTT</u>TAGC CTGGTACCAGCAGAAACCTGGCCAGGCTCCCAGGCTCCTCATCTAT*GGTGCA* |

TABLE 3-continued

Nucleotide sequences of the light chains (VL) of anti-ED-A and anti-tenascin C antibodies. VL CDR1 sequences are underlined; VL CDR2 sequences are in italics and underlined; VL CDR 3 sequences are in bold and underlined.

| Antibody | VL domain |
|---|---|
|  | *TCCAGCAGGGCCACT*GGCATCCCAGACAGGTTCAGTGGCAGTGGGTCTGGG<br>ACAGACTTCACTCTCACCATCAGCAGACTGGAGCCTGAAGATTTTGCAGTGTA<br>TTACTGTCAGCAGATGCGTGGTCGGCCGCCGACGTTCGGCCAAGGGACCAA<br>GGTGGAAATCAAA<br>(SEQ ID NO: 81) |
| E8 | GAAATTGTGTTGACGCAGTCTCCAGGCACCCTGTCTTTGTCTCCAGGGGAAA<br>AAGCCACCCTCTCCTGCAGGGCCAGTCAGAGTGTTAGC<u>TCGTCTTTTTTAGC</u><br>CTGGTACCAGCAGAAACCTGGCCAGGCTCCCAGGCTCCTCATCTAT*GGTGCA*<br>*TCCAGCAGGGCCACT*GGCATCCCAGACAGGTTCAGTGGCAGTGGGTCTGGG<br>ACAGACTTCACTCTCACCATCAGCAGACTGGAGCCTGAAGATTTTGCAGTGTA<br>TTACTGTCAGCAGATGCGTGGTCGGCCGCCGACGTTCGGCCAAGGGACCAA<br>GGTGGAAATCAAA<br>(SEQ ID NO: 83) |
| G9 | GAAATTGTGTTGACGCAGTCTCCAGGCACCCTGTCTTTGTCTCCAGGGGAAA<br>AAGCCACCCTCTCCTGCAGGGCCAGTCAGAGTGTTAGC<u>ACTGCTTTTTTAGC</u><br>CTGGTACCAGCAGAAACCTGGCCAGGCTCCCAGGCTCCTCATCTAT*GGTGCA*<br>*TCCAGCAGGGCCACT*GGCATCCCAGACAGGTTCAGTGGCAGTGGGTCTGGG<br>ACAGACTTCACTCTCACCATCAGCAGACTGGAGCCTGAAGATTTTGCAGTGTA<br>TTACTGTCAGCAGATGCGTGGTCGGCCGCCGACGTTCGGCCAAGGGACCAA<br>GGTGGAAATCAAA<br>(SEQ ID NO: 85) |
| F16 and<br>4A1-F16 | TCGTCTGAGCTGACTCAGGACCCTGCTGTGTCTGTGGCCTTGGGACAGACAG<br>TCAGGATCACATGC<u>CAAGGAGACAGCCTCAGAAGCTATTATGCAAGCTGGTA</u><br>CCAGCAGAAGCCAGGACAGGCCCCTGTACTTGTCATCTAT*GGTAAAAACAAC*<br>*CGGCCCTCA*GGGATCCCAGACCGATTCTCTGGCTCCAGCTCAGGAAACACA<br>GCTTCCTTGACCATCACTGGGGCTCAGGCGGAAGATGAGGCTGACTATTACT<br>GTAACTCCTCTGTTTATACTATGCCGCCCGTGGTATTCGGCGGAGGGACCAA<br>GCTGACCGTCCTA<br>(SEQ ID NO: 87) |

TABLE 4

Amino acid sequences of the light chains (VL) of anti-ED-A and anti-tenascin C antibodies. VL CDR1 sequences are underlined; VH CDR2 sequences are in italics and underlined; VH CDR 3 sequences are in bold and underlined.

| Antibody | VL domain |
|---|---|
| H1 | EIVLTQSPGTLSLSPGEKATLSCRASQSVS<u>SAW</u>LAVVYQQKPGQAPRLLIY*GASS*<br>*RAT*GIPDRFSGSGSGTDFTLTISRLEPEDFAVYYCQQMRGRPPTFGQGTKVEIK<br>(SEQ ID NO: 64) |
| B2 | EIVLTQSPGTLSLSPGEKATLSCRASQSVS<u>VAF</u>LAINYQQKPGQAPRLLIY*GASSR*<br>*AT*GIPDRFSGSGSGTDFTLTISRLEPEDFAVYYCQQMRGRPPTFGQGTKVEIK<br>(SEQ ID NO: 66) |
| C5 | EIVLTQSPGILSLSPGEKATLSCRASQSVS<u>LHF</u>LAWYQQKPGQAPRLLIY*GASSR*<br>*AT*GIPDRFSGSGSGTDFTLTISRLEPEDFAVYYCQQMRGRPPTFGQGTKVEIK<br>(SEQ ID NO: 68) |
| D5 | EIVLTQSPGILSLSPGEKATLSCRASQSVS<u>NAF</u>LAWYQQKPGQAPRLLIY*GASSR*<br>*AT*GIPDRFSGSGSGTDFTLTISRLEPEDFAVYYCQQMRGRPPTFGQGTKVEIK<br>(SEQ ID NO: 70) |
| E5 | EIVLTQSPGTLSLSPGEKATLSCRASQSVS<u>LAH</u>LAWYQQKPGQAPRLLIY*GASSR*<br>*AT*GIPDRFSGSGSGTDFTLTISRLEPEDFAVYYCQQMRGRPPTFGQGTKVEIK<br>(SEQ ID NO: 72) |
| C8 | EIVLTQSPGTLSLSPGEKATLSCRASQSVS<u>LPF</u>LAWYQQKPGQAPRLLIY*GASSR*<br>*AT*GIPDRFSGSGSGTDFTLTISRLEPEDFAVYYCQQMRGRPPTFGQGTKVEIK<br>(SEQ ID NO: 74) |
| F8 VL | EIVLTQSPGILSLSPGEKATLSCRASQSVS<u>MPF</u>LAWYQQKPGQAPRLLIY*GASSR*<br>*AT*GIPDRFSGSGSGTDFTLTISRLEPEDFAVYYCQQMRGRPPTFGQGTKVEIK<br>(SEQ ID NO: 76) |

TABLE 4-continued

Amino acid sequences of the light chains (VL) of anti-ED-A and anti-tenascin C antibodies. VL CDR1 sequences are underlined; VH CDR2 sequences are in italics and underlined; VH CDR 3 sequences are in bold and underlined.

| Antibody | VL domain |
| --- | --- |
| F8 VL K18R | EIVLIQSPGILSLSPGERATLSCRASQSVS<u>MPF</u>LAWYQQKPGQAPRLLIY<u>*GASSR</u><br><u>AT*</u>GIPDRFSGSGSGTDFTLTISRLEPEDFAVYYCQQ<u>MRGRPP</u>TFGQGTKVEIK<br>(SEQ ID NO: 78) |
| F1 | EIVLTQSPGTLSLSPGEKATLSCRASQSVS<u>APF</u>LAWYQQKPGQAPRLLIY<u>*GASSR</u><br><u>AT*</u>GIPDRFSGSGSGTDFTLTISRLEPEDFAVYYCQQ<u>MRGRPP</u>TFGQGTKVEIK<br>(SEQ ID NO: 80) |
| B7 | EIVLTQSPGTLSLSPGEKATLSCRASQSVS<u>LAF</u>LAWYQQKPGQAPRLLIY<u>*GASSR</u><br><u>AT*</u>GIPDRFSGSGSGTDFTLTISRLEPEDFAVYYCQQ<u>MRGRPP</u>TFGQGTKVEIK<br>(SEQ ID NO: 82) |
| E8 | EIVLTQSPGTLSLSPGEKATLSCRASQSVS<u>SSF</u>LAWYQQKPGQAPRLLIY<u>*GASSR</u><br><u>AT*</u>GIPDRFSGSGSGTDFTLTISRLEPEDFAVYYCQQ<u>MRGRPP</u>TFGQGTKVEIK<br>(SEQ ID NO: 84) |
| G9 | EIVLTQSPGTLSLSPGEKATLSCRASQSVS<u>TAF</u>LAWYQQKPGQAPRLLIY<u>*GASSR</u><br><u>AT*</u>GIPDRFSGSGSGTDFTLTISRLEPEDFAVYYCQQ<u>MRGRPP</u>TFGQGTKVEIK<br>(SEQ ID NO: 86) |
| F16 and 4A1 F16 | SSELTQDPAVSVALGQTVRITC<u>QGDSLRSYYAS</u>WYQQKPGQAPVLVIY<u>*GKNNRP</u><br><u>S*</u>GIPDRFSGSSSGNTASLTITGAQAEDEADYYC<u>NSSVYTMPPVV</u>FGGGTKLTVL<br>(SEQ ID NO: 88) |

Sequences Disclosed in Application (H1 VH domain)
SEQ ID NO: 1
GAGGTGCAGCTGGTGGAGTCTGGGGGAGGCTTGGTACAGCCTGGGGGGTCCCTGAGACTCTCCTGT

GCAGCCTCTGGATTCACCTTTAGCCCGCGGAGGATGAGCTGGGTCCGCCAGGCTCCAGGGAAGGGG

CTGGAGTGGGTCTCAGCTATTAGTGGTAGTGGTGGTAGCACATACTACGCAGACTCCGTGAAGGGCC

GGTTCACCATCTCCAGAGACAATTCCAAGAACACGCTGTATCTGCAAATGAACAGCCTGAGAGCCGAG

GACACGGCCGTATATTACTGTGCGAAAAGTACTCATTTGTATCTTTTTGACTACTGGGGCCAGGGAACC

CTGGTCACCGTCTCGAGT (H1 VH domain)
SEQ ID NO: 2
EVQLVESGGGLVQPGGSLRLSCAASGFTFSPRRMSWVRQAPGKGLEWVSAISGSGGSTYYADSVKGRFTI
SRDNSKNTLYLQMNSLRAEDTAVYYCAKSTHLYLFDYWGQGTLVTVSS (B2 VH domain)
SEQ ID NO: 3
GAGGTGCAGCTGGTGGAGTCTGGGGGAGGCTTGGTACAGCCTGGGGGGTCCCTGAGACTCTCCTGT

GCAGCCTCTGGATTCACCTTTAGCGCGGCTAAGATGAGCTGGGTCCGCCAGGCTCCAGGGAAGGGGC

TGGAGTGGGTCTCAGCTATTAGTGGTAGTGGTGGTAGCACATACTACGCAGACTCCGTGAAGGGCCG

GTTCACCATCTCCAGAGACAATTCCAAGAACACGCTGTATCTGCAAATGAACAGCCTGAGAGCCGAGG

ACACGGCCGTATATTACTGTGCGAAAAGTACTCATTTGTATCTTTTTGACTACTGGGGCCAGGGAACCC

TGGTCACCGTCTCGAGT (B2 VH domain)
SEQ ID NO: 4
EVQLVESGGGLVQPGGSLRLSCAASGFTFSAAKMSWVRQAPGKGLEWVSAISGSGGSTYYADSVKGRFTI
SRDNSKNTLYLQMNSLRAEDTAVYYCAKSTHLYLFDYWGQGTLVTVSS (C5 VH domain)
SEQ ID NO: 5
GAGGTGCAGCTGGTGGAGTCTGGGGGAGGCTTGGTACAGCCTGGGGGGTCCCTGAGACTCTCCTGT

GCAGCCTCTGGATTCACCTTTAGCCCGATTACTATGAGCTGGGTCCGCCAGGCTCCAGGGAAGGGGC

-continued

TGGAGTGGGTCTCAGCTATTAGTGGTAGTGGTGGTAGCACATACTACGCAGACTCCGTGAAGGGCCG

GTTCACCATCTCCAGAGACAATTCCAAGAACACGCTGTATCTGCAAATGAACAGCCTGAGAGCCGAGG

ACACGGCCGTATATTACTGTGCGAAAAGTACTCATTTGTATCTTTTTGACTACTGGGGCCAGGGAACCC

TGGTCACCGTCTCGAGT (C5 VH domain)
SEQ ID NO: 6
EVQLVESGGGLVQPGGSLRLSCAASGFTFSPITMSWVRQAPGKGLEWVSAISGSGGSTYYADSVKGRFTI
SRDNSKNTLYLQMNSLRAEDTAVYYCAKSTHLYLFDYWGQGTLVTVSS (D5 VH domain)
SEQ ID NO: 7
GAGGTGCAGCTGGTGGAGTCTGGGGGAGGCTTGGTACAGCCTGGGGGGTCCCTGAGACTCTCCTGT

GCAGCCTCTGGATTCACCTTTAGCGTGATGAAGATGAGCTGGGTCCGCCAGGCTCCAGGGAAGGGGC

TGGAGTGGGTCTCAGCTATTAGTGGTAGTGGTGGTAGCACATACTACGCAGACTCCGTGAAGGGCCG

GTTCACCATCTCCAGAGACAATTCCAAGAACACGCTGTATCTGCAAATGAACAGCCTGAGAGCCGAGG

ACACGGCCGTATATTACTGTGCGAAAAGTACTCATTTGTATCTTTTTGACTACTGGGGCCAGGGAACCC

TGGTCACCGTCTCGAGT (D5 VH domain)
SEQ ID NO: 8
EVQLVESGGGLVQPGGSLRLSCAASGFTFSVMKMSWVRQAPGKGLEWVSAISGSGGSTYYADSVKGRFTI
SRDNSKNTLYLQMNSLRAEDTAVYYCAKSTHLYLFDYWGQGTLVTVSS (E5 VH domain)
SEQ ID NO: 9
GAGGTGCAGCTGGTGGAGTCTGGGGGAGGCTTGGTACAGCCTGGGGGGTCCCTGAGACTCTCCTGT

GCAGCCTCTGGATTCACCTTTAGCACTGGTTCTATGAGCTGGGTCCGCCAGGCTCCAGGGAAGGGGC

TGGAGTGGGTCTCAGCTATTAGTGGTAGTGGTGGTAGCACATACTACGCAGACTCCGTGAAGGGCCG

GTTCACCATCTCCAGAGACAATTCCAAGAACACGCTGTATCTGCAAATGAACAGCCTGAGAGCCGAGG

ACACGGCCGTATATTACTGTGCGAAAAGTACTCATTTGTATCTTTTTGACTACTGGGGCCAGGGAACCC

TGGTCACCGTCTCGAGT (E5 VH domain)
SEQ ID NO: 10
EVQLVESGGGLVQPGGSLRLSCAASGFTFSTGSMSWVRQAPGKGLEWVSAISGSGGSTYYADSVKGRFTI
SRDNSKNTLYLQMNSLRAEDTAVYYCAKSTHLYLFDYWGQGTLVTVSS (C8 VH domain)
SEQ ID NO: 11
GAGGTGCAGCTGGTGGAGTCTGGGGGAGGCTTGGTACAGCCTGGGGGGTCCCTGAGACTCTCCTGT

GCAGCCTCTGGATTCACCTTTAGCCTTCAGACTATGAGCTGGGTCCGCCAGGCTCCAGGGAAGGGGC

TGGAGTGGGTCTCAGCTATTAGTGGTAGTGGTGGTAGCACATACTACGCAGACTCCGTGAAGGGCCG

GTTCACCATCTCCAGAGACAATTCCAAGAACACGCTGTATCTGCAAATGAACAGCCTGAGAGCCGAGG

ACACGGCCGTATATTACTGTGCGAAAAGTACTCATTTGTATCTTTTTGACTACTGGGGCCAGGGAACCC

TGGTCACCGTCTCGAGT (C8 VH domain)
SEQ ID NO: 12
EVQLVESGGGLVQPGGSLRLSCAASGFTFSLQTMSWVRQAPGKGLEWVSAISGSGGSTYYADSVKGRFTI
SRDNSKNTLYLQMNSLRAEDTAVYYCAKSTHLYLFDYWGQGTLVTVSS (F8 VH domain)
SEQ ID NO: 13
GAGGTGCAGCTGGTGGAGTCTGGGGGAGGCTTGGTACAGCCTGGGGGGTCCCTGAGACTCTCCTGT

GCAGCCTCTGGATTCACCTTTAGCCTGTTTACGATGAGCTGGGTCCGCCAGGCTCCAGGGAAGGGGC

TGGAGTGGGTCTCAGCTATTAGTGGTAGTGGTGGTAGCACATACTACGCAGACTCCGTGAAGGGCCG

-continued
```
GTTCACCATCTCCAGAGACAATTCCAAGAACACGCTGTATCTGCAAATGAACAGCCTGAGAGCCGAGG

ACACGGCCGTATATTACTGTGCGAAAAGTACTCATTTGTATCTTTTTGACTACTGGGGCCAGGGAACCC

TGGTCACCGTCTCGAGT
```

(F8 VH domain)
SEQ ID NO: 14
```
EVQLVESGGGLVQPGGSLRLSCAASGFTFSLFTMSWVRQAPGKGLEWVSAISGSGGSTYYADSVKGRFTI
SRDNSKNTLYLQMNSLRAEDTAVYYCAKSTHLYLFDYWGQGTLVTVSS
```

(F8 VH V5L domain)
SEQ ID NO: 15
```
GAGGTGCAGCTGTTGGAGTCTGGGGGAGGCTTGGTACAGCCTGGGGGGTCCCTGAGACTCTCCTGTG

CAGCCTCTGGATTCACCTTTAGCCTGTTTACGATGAGCTGGGTCCGCCAGGCTCCAGGGAAGGGGCT

GGAGTGGGTCTCAGCTATTAGTGGTAGTGGTGGTAGCACATACTACGCAGACTCCGTGAAGGGCCGG

TTCACCATCTCCAGAGACAATTCCAAGAACACGCTGTATCTGCAAATGAACAGCCTGAGAGCCGAGGA

CACGGCCGTATATTACTGTGCGAAAAGTACTCATTTGTATCTTTTTGACTACTGGGGCCAGGGAACCCT

GGTCACCGTCTCGAGT
```

(F8 VH V5L domain)
SEQ ID NO: 16
```
EVQLLESGGGLVQPGGSLRLSCAASGFTFSLFTMSWVRQAPGKGLEWVSAISGSGGSTYYADSVKGRFTI
SRDNSKNTLYLQMNSLRAEDTAVYYCAKSTHLYLFDYWGQGTLVTVSS
```

(F1 VH domain)
SEQ ID NO: 17
```
GAGGTGCAGCTGGTGGAGTCTGGGGGAGGCTTGGTACAGCCTGGGGGGTCCCTGAGACTCTCCTGT

GCAGCCTCTGGATTCACCTTTAGCTAGGCGCGTATGAGCTGGGTCCGCCAGGCTCCAGGGAAGGGGC

TGGAGTGGGTCTCAGCTATTAGTGGTAGTGGTGGTAGCACATACTACGCAGACTCCGTGAAGGGCCG

GTTCACCATCTCCAGAGACAATTCCAAGAACACGCTGTATCTGCAAATGAACAGCCTGAGAGCCGAGG

ACACGGCCGTATATTACTGTGCGAAAAGTACTCATTTGTATCTTTTTGACTACTGGGGCCAGGGAACCC

TGGTCACCGTCTCGAGT
```

(F1 VH domain)
SEQ ID NO: 18
```
EVQLVESGGGLVQPGGSLRLSCAASGFTFSQARMSWVRQAPGKGLEWVSAISGSGGSTYYADSVKGRFTI
SRDNSKNTLYLQMNSLRAEDTAVYYCAKSTHLYLFDYWGQGTLVTVSS
```

(B7 VH domain)
SEQ ID NO: 19
```
GAGGTGCAGCTGGTGGAGTCTGGGGGAGGCTTGGTACAGCCTGGGGGGTCCCTGAGACTCTCCTGT

GCAGCCTCTGGATTCACCTTTAGCCATTTTGATATGAGCTGGGTCCGCCAGGCTCCAGGGAAGGGGCT

GGAGTGGGTCTCAGCTATTAGTGGTAGTGGTGGTAGCACATACTACGCAGACTCCGTGAAGGGCCGG

TTCACCATCTCCAGAGACAATTCCAAGAACACGCTGTATCTGCAAATGAACAGCCTGAGAGCCGAGGA

CACGGCCGTATATTACTGTGCGAAAAGTACTCATTTGTATCTTTTTGACTACTGGGGCCAGGGAACCCT

GGTCACCGTCTCGAGT
```

(B7 VH domain)
SEQ ID NO: 20
```
EVQLVESGGGLVQPGGSLRLSCAASGFTFSHFDMSWVRQAPGKGLEWVSAISGSGGSTYYADSVKGRFTI
SRDNSKNTLYLQMNSLRAEDTAVYYCAKSTHLYLFDYWGQGTLVTVSS
```

(E8 VH domain)
SEQ ID NO: 21
```
GAGGTGCAGCTGGTGGAGTCTGGGGGAGGCTTGGTACAGCCTGGGGGGTCCCTGAGACTCTCCTGT

GCAGCCTCTGGATTCACCTTTAGCGATATGCATATGAGCTGGGTCCGCCAGGCTCCAGGGAAGGGGC

TGGAGTGGGTCTCAGCTATTAGTGGTAGTGGTGGTAGCACATACTACGCAGACTCCGTGAAGGGCCG

GTTCACCATCTCCAGAGACAATTCCAAGAACACGCTGTATCTGCAAATGAACAGCCTGAGAGCCGAGG

ACACGGCCGTATATTACTGTGCGAAAAGTACTCATTTGTATCTTTTTGACTACTGGGGCCAGGGAACCC

TGGTCACCGTCTCGAGT
```

-continued (E8 VH domain)

SEQ ID NO: 22

EVQLVESGGGLVQPGGSLRLSCAASGFTFSDMHMSWVRQAPGKGLEWVSAISGSGGSTYYADSVKGRFT
ISRDNSKNTLYLQMNSLRAEDTAVYYCAKSTHLYLFDYWGQGTLVTVSS (G9 VH domain)

SEQ ID NO: 23

GAGGTGCAGCTGGTGGAGTCTGGGGGAGGCTTGGTACAGCCTGGGGGGTCCCTGAGACTCTCCTGT

GCAGCCTCTGGATTCACCTTTAGCCATATGCAGATGAGCTGGGTCCGCCAGGCTCCAGGGAAGGGGC

TGGAGTGGGTCTCAGCTATTAGTGGTAGTGGTGGTAGCACATACTACGCAGACTCCGTGAAGGGCCG

GTTCACCATCTCCAGAGACAATTCCAAGAACACGCTGTATCTGCAAATGAACAGCCTGAGAGCCGAGG

ACACGGCCGTATATTACTGTGCGAAAAGTACTCATTTGTATCTTTTTGACTACTGGGGCCAGGGAACCC

TGGTCACCGTCTCGAGT (G9 VH domain)

SEQ ID NO: 24

EVQLVESGGGLVQPGGSLRLSCAASGFTFSHMQMSWVRQAPGKGLEWVSAISGSGGSTYYADSVKGRFT
ISRDNSKNTLYLQMNSLRAEDTAVYYCAKSTHLYLFDYWGQGTLVTVSS (F16 VH domain)

SEQ ID NO: 25

GAGGTGCAGCTGTTGGAGTCTGGGGGAGGCTTGGTACAGCCTGGGGGGTCCCTGAGACTCTCCTGTG

CAGCCTCTGGATTCACCTTTAGCCGGTATGGTATGAGCTGGGTCCGCCAGGCTCCAGGGAAGGGGCT

GGAGTGGGTCTCAGCTATTAGTGGTAGTGGTGGTAGCACATACTACGCAGACTCCGTGAAGGGCCGG

TTCACCATCTCCAGAGACAATTCCAAGAACACGCTGTATCTGCAAATGAACAGCCTGAGAGCCGAGGA

CACGGCCGTATATTACTGTGCGAAAGCGCATAATGCTTTTGACTACTGGGGCCAGGGAACCCTGGTCA

CCGTGTCGAGA (F16 VH domain)

SEQ ID NO: 26

EVQLLESGGGLVQPGGSLRLSCAASGFTFSRYGMSWVRQAPGKGLEWVSAISGSGGSTYYADSVKGRFTI
SRDNSKNTLYLQMNSLRAEDTAVYYCAKAHNAFDYWGQGTLVTVSR (4A1-F16 VH domain)

SEQ ID NO: 27

GAGGTGCAGCTGTTGGAGTCTGGGGGAGGCTTGGTACAGCCTGGGGGGTCCCTGAGACTCTCCTGTG

CAGCCTCTGGATTCACCTTTAGCCGGTATGGTGCGAGCTGGGTCCGCCAGGCTCCAGGGAAGGGGCT

GGAGTGGGTCTCAGCTATTAGTGGTAGTGGTGGTAGCACATACTACGCAGACTCCGTGAAGGGCCGG

TTCACCATCTCCAGAGACAATTCCAAGAACACGCTGTATCTGCAAATGAACAGCCTGAGAGCCGAGGA

CACGGCCGTATATTACTGTGCGAAAGCGCATAATGCTTTTGACTACTGGGGCCAGGGAACCCTGGTCA

CCGTGTCGAGA (4A1-F16 VH domain)

SEQ ID NO: 28

EVQLLESGGGLVQPGGSLRLSCAASGFTFSRYGASWVRQAPGKGLEWVSAISGSGGSTYYADSVKGRFTI
SRDNSKNTLYLQMNSLRAEDTAVYYCAKAHNAFDYWGQGTLVTVSR (H1 VH CDR1)

SEQ ID NO: 29

CCGCGGAGG (H1 VH CDR1)

SEQ ID NO: 30

PRR (B2 VH CDR1)

SEQ ID NO: 31

GCGGCTAAG (B2 VH CDR1)

SEQ ID NO: 32

AAK

```
(C5 VH CDR1)
                                                 SEQ ID NO: 33
CCGATTACT (C5 VH CDR1)
                                                 SEQ ID NO: 34
PIT (D5 VH CDR1)
                                                 SEQ ID NO: 35
GTGATGAAG (D5 VH CDR1)
                                                 SEQ ID NO: 36
VMK (E5 VH CDR1)
                                                 SEQ ID NO: 37
ACTGGTTCT (E5 VH CDR1)
                                                 SEQ ID NO: 38
TGS (C8 VH CDR1)
                                                 SEQ ID NO: 39
CTTCAGACT (C8 VH CDR1)
                                                 SEQ ID NO: 40
LQT (F8 VH and F8 VH V5L CDR1)
                                                 SEQ ID NO: 41
CTGTTTACG (F8 VH and F8 VH V5L CDR1)
                                                 SEQ ID NO: 42
LFT (F1 VH CDR1)
                                                 SEQ ID NO: 43
TAGGCGCGT (F1 VH CDR1)
                                                 SEQ ID NO: 44
QAR (B7 VH CDR1)
                                                 SEQ ID NO: 45
CATTTTGAT (B7 VH CDR1)
                                                 SEQ ID NO: 46
HFD (E8 VH CDR1)
                                                 SEQ ID NO: 47
GATATGCAT (E8 VH CDR1)
                                                 SEQ ID NO: 48
DMH (G9 VH CDR1)
                                                 SEQ ID NO: 49
CATATGCAG (G9 VH CDR1)
                                                 SEQ ID NO: 50
HMQ (F16 VH CDR1)
                                                 SEQ ID NO: 51
CGGTATGGTATGAGC (F16 VH CDR1)
                                                 SEQ ID NO: 52
RYGMS
```

-continued (4A1-F16 VH CDR1)
SEQ ID NO: 53
CGGTATGGTGCGAGC (4A1-F16 VH CDR1)
SEQ ID NO: 54
RYGAS (H1, B2, C5, D5, E5, C8, F8, F8 V5L, F1, B7, E8 and G9 VH CDR2)
SEQ ID NO: 55
AGTGGTAGTGGTGGTAGC (H1, B2, C5, D5, E5, C8, F8, F8 V5L, F1, B7, E8 and G9 VH CDR2)
SEQ ID NO: 56
SGSGGS (F16 and 4A1-F16 VH CDR2)
SEQ ID NO: 57
GCTATTAGTGGTAGTGGTGGTAGCACATACTACGCAGACTCCGTGAAGGGC (F16 and 4A1-F16 VH CDR2)
SEQ ID NO: 58
AISGSGGSTYYADSVKG (H1, B2, C5, D5, E5, C8, F8, F8 V5L, F1, B7, E8 and G9 VH CDR3)
SEQ ID NO: 59
AGTACTCATTTGTATCTT (H1, B2, C5, D5, E5, C8, F8, F8 V5L, F1, 87, E8 and G9 VH CDR3)
SEQ ID NO: 60
STHLYL (F16 and 4A1-F16 VH CDR3)
SEQ ID NO: 61
GCGCATAATGCTTTTGACTAC (F16 and 4A1-F16 VH CDR3)
SEQ ID NO: 62
AHNAFDY (H1 VL domain)
SEQ ID NO: 63
GAAATTGTGTTGACGCAGTCTCCAGGCACCCTGTCTTTGTCTCCAGGGGAAAAAGCCACCCTCTCCTG

CAGGGCCAGTCAGAGTGTTAGCTCTGCGTGGTTAGCCTGGTACCAGCAGAAACCTGGCCAGGCTCCC

AGGCTCCTCATCTATGGTGCATCCAGCAGGGCCACTGGCATCCCAGACAGGTTCAGTGGCAGTGGGT

CTGGGACAGACTTCACTCTCACCATCAGCAGACTGGAGCCTGAAGATTTTGCAGTGTATTACTGTCAGC

AGATGCGTGGTCGGCCGCCGACGTTCGGCCAAGGGACCAAGGTGGAAATCAAA (H1 VL domain)
SEQ ID NO: 64
EIVLTQSPGTLSLSPGEKATLSCRASQSVSSAWLAWYQQKPGQAPRLLIYGASSRATGIPDRFSGSGSGTD
FTLTISRLEPEDFAVYYCQQMRGRPPTFGQGTKVEIK (B2 VL domain)
SEQ ID NO: 65
GAAATTGTGTTGACGCAGTCTCCAGGCACCCTGTCTTTGTCTCCAGGGGAAAAAGGCACCCTCTCCTG

CAGGGCCAGTCAGAGTGTTAGCGTGGCTTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

TGGGACAGACTTCACTCTCACCATCAGCAGACTGGAGCCTGAAGATTTTGCAGTGTATTACTGTCAGCA

GATGCGTGGTCGGCCGCCGACGTTCGGCCAAGGGACCAAGGTGGAAATCAAA (B2 VL domain)
SEQ ID NO: 66
EIVLTQSPGTLSLSPGEKATLSCRASQSVSVARAWYQQKPGQAPRWYGASSRATGIPDRFSGSGSGTDF
TLTISRLEPEDFAVYYCQQMRGRPPTFGQGTKVEIK (C5 VL domain)
SEQ ID NO: 67
GAAATTGTGTTGACGCAGTCTCCAGGCACCCTGTCTTTGTCTCCAGGGGAAAAAGCCACCCTCTCCTG

CAGGGCCAGTCAGAGTGTTAGCTTGCATTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

```
TGGGACAGACTTCACTCTCACCATCAGCAGACTGGAGCCTGAAGATTTTGCAGTGTATTACTGTCAGCA

GATGCGTGGTCGGCCGCCGACGTTCGGCCAAGGGACCAAGGTGGAAATCAAA (C5 VL domain)
                                                        SEQ ID NO: 68
EIVLTQSPGTLSLSPGEKATLSCRASQSVSLHFLAWYQQKPGQAPRWYGASSRATGIPDRFSGSGSGTDF
TLTISRLEPEDFAVYYCQQMRGRPPTFGQGTKVEIK (D5 VL domain)
                                                        SEQ ID NO: 69
GAAATTGTGTTGACGCAGTCTCCAGGCACCCTGTCTTTGTCTCCAGGGGAAAAAGCCACCCTCTCCTG

CAGGGCCAGTCAGAGTGTTAGCAATGCTTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

TGGGACAGACTTCACTCTCACCATCAGCAGACTGGAGCCTGAAGATTTTGCAGTGTATTACTGTCAGCA

GATGCGTGGTCGGCCGCCGACGTTCGGCCAAGGGACCAAGGTGGAAATCAAA (D5 VL domain)
                                                        SEQ ID NO: 70
EIVLIQSPGTLSLSPGEKATLSCRASQSVSNAFLAWYQQKPGQAPRLLIYGASSRATGIPDRFSGSGSGTDF
TLTISRLEPEDFAVYYCQQMRGRPPTFGQGTKVEIK (E5 VL domain)
                                                        SEQ ID NO: 71
GAAATTGTGTTGACGCAGTCTCCAGGCACCCTGTCTTTGTCTCCAGGGGAAAAAGCCACCCTCTCCTG

CAGGGCCAGTCAGAGTGTTAGCCTTGCGCATTTAGCCTGGTACCAGCAGAAACCTGGCCAGGCTCCC

AGGCTCCTCATCTATGGTGCATCCAGCAGGGCCACTGGCATCCCAGACAGGTTCAGTGGCAGTGGGT

CTGGGACAGACTTCACTCTCACCATCAGCAGACTGGAGCCTGAAGATTTTGCAGTGTATTACTGTCAGC

AGATGCGTGGTCGGCCGCCGACGTTCGGCCAAGGGACCAAGGTGGAAATCAAA (E5 VL domain)
                                                        SEQ ID NO: 72
EIVLTQSPGTLSLSPGEKATLSCRASQSVSLAHLAWYQQKPGQAPRLLIYGASSRATGIPDRFSGSGSGTDF
TLTISRLEPEDFAVYYCQQMRGRPPTFGQGTKVEIK (C8 VL domain)
                                                        SEQ ID NO: 73
GAAATTGTGTTGACGCAGTCTCCAGGCACCCTGTCTTTGTCTCCAGGGGAAAAAGCCACCCTCTCCTG

CAGGGCCAGTCAGAGTGTTAGCCTTCCTTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

TGGGACAGACTTCACTCTCACCATCAGCAGACTGGAGCCTGAAGATTTTGCAGTGTATTACTGTCAGCA

GATGCGTGGTCGGCCGCCGACGTTCGGCCAAGGGACCAAGGTGGAAATCAAA (C8 VL domain)
                                                        SEQ ID NO: 74
EIVLTQSPGTLSLSPGEKATLSCRASQSVSLPFLAWYQQKPGQAPRLLIYGASSRATGIPDRFSGSGSGTDF
TLTISRLEPEDFAVYYCQQMRGRPPTFGQGTKVEIK (F8 VL domain)
                                                        SEQ ID NO: 75
GAAATTGTGTTGACGCAGTCTCCAGGCACCCTGTCTTTGTCTCCAGGGGAAAAAGCCACCCTCTCCTG

CAGGGCCAGTCAGAGTGTTAGCATGCCGTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

TGGGACAGACTTCACTCTCACCATCAGCAGACTGGAGCCTGAAGATTTTGCAGTGTATTACTGTCAGCA

GATGCGTGGTCGGCCGCCGACGTTCGGCCAAGGGACCAAGGTGGAAATCAAA (F8 VL domain)
                                                        SEQ ID NO: 76
EIVLTQSPGTLSLSPGEKATLSCRASQSVSMPFLAWYQQKPGQAPRLLIYGASSRATGIPDRFSGSGSGTD
FTLTISRLEPEDFAVYYCQQMRGRPPTFGQGTKVEIK
```

-continued (F8 VL K18R domain)
SEQ ID NO: 77
GAAATTGTGTTGACGCAGTCTCCAGGCACCCTGTCTTTGTCTCCAGGGGAAAGAGCCACCCTCTCCTG

CAGGGCCAGTCAGAGIGTTAGCATGCCGTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

TGGGACAGACTTCACTCTCACCATCAGCAGACTGGAGCCTGAAGATITTGCAGTGTATTACTGTCAGCA

GATGCGTGGTCGGCCGCCGACGTTCGGCCAAGGGACCAAGGTGGAAATCAAA (F8 VL K18R domain)
SEQ ID NO: 78
EIVLTQSPGTLSLSPGERATLSCRASQSVSMPFLAWYQQKPGQAPRLLIYGASSRATGIPDRFSGSGSGTD
FTLTISRLEPEDFAVYYCQQMRGRPPTFGQGTKVEIK (F1 VL domain)
SEQ ID NO: 79
GAAATTGTGTTGACGCAGTCTCCAGGCACCCTGTCTTTGTCTCCAGGGGAAAAAGCCACCCTCTCCTG

CAGGGCCAGTCAGAGTGTTAGCGCGCCTTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

TGGGACAGACTTCACTCTCACCATCAGCAGACTGGAGCCTGAAGATTTTGCAGTGTATTACTGTCAGCA

GATGCGTGGTCGGCCGCCGACGTTCGGCCAAGGGACCAAGGTGGAAATCAAA (F1 VL domain)
SEQ ID NO: 80
EIVLTQSPGILSLSPGEKATLSCRASQSVSAPFLAWYQQKPGQAPRLLIVGASSRATGIPDRFSGSGSGTDF
TLTISRLEPEDFAVYYCQQMRGRPPTFGQGTKVEIK (B7 VL domain)
SEQ ID NO: 81
GAAATTGTGTTGACGCAGTCTCCAGGCACCCTGTCTTTGTCTCCAGGGGAAAAAGCCACCCTCTCCTG

CAGGGCCAGTCAGAGTGTTAGCCTGGCTTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

TGGGACAGACTTCACTCTCACCATCAGCAGACTGGAGCCTGAAGATTTTGCAGTGTATTACTGTCAGCA

GATGCGTGGTCGGCCGCCGACGTTCGGCCAAGGGACCAAGGTGGAAATCAAA (B7 VL domain)
SEQ ID NO: 82
EIVLTQSPGTLSLSPGEKATLSCRASQSVSLAFLAWYQQKPGQAPRWYGASSRATGIPDRFSGSGSGTDF
TLTISRLEPEDFAVYYCQQMRGRPPTFGQGTKVEIK (E8 VL domain)
SEQ ID NO: 83
GAAATTGTGTTGACGCAGTCTCCAGGCACCCTGTCTTTGTCTCCAGGGGAAAAAGCCACCCTCTCCTG

CAGGGCCAGTCAGAGTGTTAGCTCGTCTTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

TGGGACAGACTTCACTCTCACCATCAGCAGACTGGAGCCTGAAGATTTTGCAGTGTATTACTGTCAGCA

GATGCGTGGTCGGCCGCCGACGTTCGGCCAAGGGACCAAGGTGGAAATCAAA (E8 VL domain)
SEQ ID NO: 84
EIVLTQSPGTLSLSPGEKATLSCRASQSVSSSFLAWYQQKPGQAPRLLIYGASSRATGIPDRFSGSGSGTDF
TLTISRLEPEDFAVYYCQQMRGRPPTFGQGTKVEIK (G9 VL domain)
SEQ ID NO: 85
GAAATTGTGTTGACGCAGTCTCCAGGCACCCTGTCTTTGTCTCCAGGGGAAAAAGCCACCCTCTCCTG

CAGGGCCAGTCAGAGTGTTAGCACTGCTTTTTTAGCCTGGTACCAGCAGAAACCTGGCCAGGCTCCCA

GGCTCCTCATCTATGGTGCATCCAGCAGGGCCACTGGCATCCCAGACAGGTTCAGTGGCAGTGGGTC

TGGGACAGACTTCACTCTCACCATCAGCAGACTGGAGCCTGAAGATTTTGCAGTGTATTACTGTCAGCA

GATGCGTGGTCGGCCGCCGACGTTCGGCCAAGGGACCAAGGTGGAAATCAAA (G9 VL domain)

SEQ ID NO: 86

EIVLTQSPGTLSLSPGEKATLSCRASQSVSTAFLAWYQQKPGQAPRLLIYGASSRATGIPDRFSGSGSGTDF
TLTISRLEPEDFAVYYCQQMRGRPPTFGQGTKVEIK (F16 and 4A1-F16 VL domain)

SEQ ID NO: 87

TCGTCTGAGCTGACTCAGGACCCTGCTGTGTCTGTGGCCTTGGGACAGACAGTCAGGATCACATGCCA

AGGAGACAGCCTCAGAAGCTATTATGCAAGCTGGTACCAGCAGAAGCCAGGACAGGCCCCTGTACTTG

TCATCTATGGTAAAAACAACCGGCCCTCAGGGATCCCAGACCGATTCTCTGGCTCCAGCTCAGGAAAC

ACAGCTTCCTTGACCATCACTGGGGCTCAGGCGGAAGATGAGGCTGACTATTACTGTAACTCCTCTGTT

TATACTATGCCGCCCGTGGTATTCGGCGGAGGGACCAAGCTGACCGTCCTA (F16 and 4A1-F16 VL domain)

SEQ ID NO: 88

SSELTQDPAVSVALGQTVRITCQGDSLRSYYASWYQQKPGQAPVLVIYGKNNRPSGIPDRFSGSSSGNTAS
LTITGAQAEDEADYYCNSSVYTMPPWFGGGTKLTVL (H1 VL CDR1)

SEQ ID NO: 89

TCTGCGTGG (H1 VL CDR1)

SEQ ID NO: 90

SAW (B2 VL CDR1)

SEQ ID NO: 91

GTGGCTTTT (B2 VL CDR1)

SEQ ID NO: 92

VAF (C5 VL CDR1)

SEQ ID NO: 93

TTGCATTTT (C5 VL CDR1)

SEQ ID NO: 94

LHF (D5 VL CDR1)

SEQ ID NO: 95

AATGCTTTT (D5 VL CDR1)

SEQ ID NO: 96

NAF (E5 VL CDR1)

SEQ ID NO: 97

CTTGCGCAT (E5 VL CDR1)

SEQ ID NO: 98

LAH (C8 VL CDR1)

SEQ ID NO: 99

CTTCCTTTT (C8 VL CDR1)

SEQ ID NO: 100

LPF (F8 VL and F8 VL K18R CDR1)

SEQ ID NO: 101

ATGCCGTTT (F8 VL and F8 VL K18R CDR1)

SEQ ID NO: 102

MPF (F1 VL CDR1)

SEQ ID NO: 103

GCGCCITTT

```
(F1 VL CDR1)
                                                     SEQ ID NO: 104
APF (B7 VL CDR1)
                                                     SEQ ID NO: 105
CTGGCTTTT (B7 VL CDR1)
                                                     SEQ ID NO: 106
LAF (E8 VL CDR1)
                                                     SEQ ID NO: 107
TCGTCTTTT (E8 VL CDR1)
                                                     SEQ ID NO: 108
SSF (G9 VL CDR1)
                                                     SEQ ID NO: 109
ACTGCTTTT

G9 VL CDR1)
                                                     SEQ ID NO: 110
TAF (F16 and 4A1-F16 VL CDR1)
                                                     SEQ ID NO: 111
CAAGGAGACAGCCTCAGAAGCTATTATGCAAGC (F16 and 4A1-F16 VL CDR1)
                                                     SEQ ID NO: 112
QGDSLRSYYAS (H1, B2, C5, D5, E5, C8, F8, F8 K18R, F1, B7, E8 and G9 VL CDR2)
                                                     SEQ ID NO: 113
GGTGCATCCAGCAGGGCCACT (H1, B2, C5, D5, E5, C8, F8, F8 K18R, F1, B7, E8 and G9 VL CDR2)
                                                     SEQ ID NO: 114
GASSRAT (F16 and 4A1-F16 VL CDR2)
                                                     SEQ ID NO: 115
GGTAAAAACAACCGGCCCTCA (F16 and 4A1-F16 VL CDR2)
                                                     SEQ ID NO: 116
GKNNRPS (H1, B2, C5, D5, E5, C8, F8, F8 K18R, F1, B7, E8 and G9 VL CDR3)
                                                     SEQ ID NO: 117
ATGCGTGGTCGGCCGCCG (H1, B2, C5, D5, E5, C8, F8, F8 K18R, F1, B7, E8 and G9 VL CDR3)
                                                     SEQ ID NO: 118
MRGRPP (F16 and 4A1-F16 VL CDR3)
                                                     SEQ ID NO: 119
AACTCCTCTGTTTATACTATGCCGCCCGTGGTA (F16 and 4A1-F16 VL CDR3)
                                                     SEQ ID NO: 120
NSSVYTMPPVV (F8, F16 and 4A1-F16 linker)
                                                     SEQ ID NO: 121
GGCGGTAGCGGAGGG (F8, F16 and 4A1-F16 linker)
                                                     SEQ ID NO: 122
GGSGG (H1 VH V5L domain)
                                                     SEQ ID NO: 123
EVQLLESGGGLVQPGGSLRLSCAASGFTFSPRRMSWVRQAPGKGLEWVSAISGSGGSTYYADSVKGRFT1
SRDNSKNTLYLQMNSLRAEDTAVYYCAKSTHLYLFDYWGQGTLVTVSS
```

(B2 VH V5L domain)

SEQ ID NO: 124

EVQLLESGGGLVQPGGSLRLSCAASGFTFSAAKMSAWRQAPGKGLEWVSAISGSGGSTYYADSVKGRFTI
SRDNSKNTLYLQMNSLRAEDTAVYYCAKSTHLYLFDYWGQGTLVTVSS (C5 VH V5L domain)

SEQ ID NO: 125

EVQLLESGGGLVQPGGSLRLSCAASGFTFSPITMSWVRQAPGKGLEWVSAISGSGGSTYYADSVKGRFTIS
RDNSKNTLYLQMNSLRAEDTAVYYCAKSTHLYLFDYWGQGTLVTVSS (D5 VH V5L domain)

SEQ ID NO: 126

EVQLLESGGGLVQPGGSLRLSCAASGFTFSVMKMSWVRQAPGKGLEWVSAISGSGGSTYYADSVKGRFTI
SRDNSKNTLYLQMNSLRAEDTAVYYCAKSTHLYLFDYWGQGTLVTVSS (E5 VH V5L domain)

SEQ ID NO: 127

EVQLLESGGGLVQPGGSLRLSCAASGFTFSTGSMSWVRQAPGKGLEWVSAISGSGGSTYYADSVKGRFTI
SRDNSKNTLYLQMNSLRAEDTAVYYCAKSTHLYLFDYWGQGTLVTVSS (C8 VH V5L domain)

SEQ ID NO: 128

EVQLLESGGGLVQPGGSLRLSCAASGFTFSLQTMSWVRQAPGKGLEWVSAISGSGGSTYYADSVKGRFTI
SRDNSKNTLYLQMNSLRAEDTAVYYCAKSTHLYLFDYWGQGTLVTVSS (F1 VH V5L domain)

SEQ ID NO: 129

EVQLLESGGGLVQPGGSLRLSCAASGFTFSQARMSWVRQAPGKGLEWVSAISGSGGSTYYADSVKGRFTI
SRDNSKNTLYLQMNSLRAEDTAVYYCAKSTHLYLFDYWGQGTLVTVSS (B7 VH V5L domain)

SEQ ID NO: 130

EVQLLESGGGLVQPGGSLRLSCAASGFTFSHFDMSWVRQAPGKGLEWVSAISGSGGSTYYADSVKGRFTI
SRDNSKNTLYLQMNSLRAEDTAVYYCAKSTHLYLFDYWGQGTLVTVSS (E8 VH V5L domain)

SEQ ID NO: 131

EVQLLESGGGLVQPGGSLRLSCAASGFTFSDMHMSWVRQAPGKGLEWVSAISGSGGSTYYADSVKGRFTI
SRDNSKNTLYLQMNSLRAEDTAVYYCAKSTHLYLFDYWGQGTLVTVSS (G9 VH V5L domain)

SEQ ID NO: 132

EVQLLESGGGLVQPGGSLRLSCAASGFTFSHMQMSWVRQAPGKGLEWVSAISGSGGSTYYADSVKGRFT
ISRDNSKNTLYLQMNSLRAEDTAVYYCAKSTHLYLFDYWGQGTLVTVSS (H1 VL K18R domain)

SEQ ID NO: 133

EIVLTQSPGTLSLSPGERATLSCRASQSVSSAWLAWYQQKPGQAPRLLIYGASSRATGIPDRFSGSGSGTD
FTLTISRLEPEDFAVYYCQQMRGRPPTFGQGTKVEIK (B2 VL K18R domain)

SEQ ID NO: 134

EIVLTQSPGTLSLSPGERATLSCRASQSVSVAFLAWYQQKPGQAPRLLIYGASSRATGIPDRFSGSGSGTDF
TLTISRLEPEDFAVYYCQQMRGRPPTFGQGTKVEIK (C5 VL K18R domain)

SEQ ID NO: 135

EIVLTQSPGTLSLSPGERATLSCRASQSVSLHFLAWYQQKPGQAPRLLIYGASSRATGIPDRFSGSGSGTDF
TLTISRLEPEDFAVYYCQQMRGRPPTFGQGTKVEIK (D5 VL K18R domain)

SEQ ID NO: 136

EIVLTQSPGTLSLSPGERATLSCRASQSVSNAFLAWYQQKPGQAPRLLIYGASSRATGIPDRFSGSGSGTDF
TLTISRLEPEDFAVYYCQQMRGRPPTFGQGTKVEIK (E5 VL K18R domain)

SEQ ID NO: 137

EIVLTQSPGTLSLSPGERATLSCRASQSVSLAHLAWYQQKPGQAPRLLIVGASSRATGIPDRFSGSGSGTDF
TLTISRLEPEDFAVYYCQQMRGRPPTFGQGTKVEIK (C8 VL K18R domain)

SEQ ID NO: 138

EIVLTQSPGTLSLSPGERATLSCRASQSVSLPFLAWYQQKPGQAPRLLIYGASSRATGIPDRFSGSGSGTDF
TLTISRLEPEDFAVYYCQQMRGRPPTFGQGTKVEIK (F1 VL K18R domain)

SEQ ID NO: 139

EIVLTQSPGTLSLSPGERATLSCRASQSVSAPFLAWYQQKPGQAPRLLIYGASSRATGIPDRFSGSGSGTDF
TLTISRLEPEDFAVYYCQQMRGRPPTFGQGTKVEIK (B7 VL K18R domain)

SEQ ID NO: 140

EIVLTQSPGTLSLSPGERATLSCRASQSVSLAFLAWYQQKPGQAPRLLIVGASSRATGIPDRFSGSGSGTDF
TLTISRLEPEDFAVYYCQQMRGRPPTFGQGTKVEIK (E8 VL K18R domain)

SEQ ID NO: 141

EIVLTQSPGTLSLSPGERATLSCRASQSVSSSFLAWYQQKPGQAPRLLIYGASSRATGIPDRFSGSGSGTDF
TLTISRLEPEDFAVYYCQQMRGRPPTFGQGTKVEIK (G9 VL K18R domain)

SEQ ID NO: 142

EIVLTQSPGTLSLSPGERATLSCRASQSVSTAFLAWYQQKPGQAPRLLIVGASSRATGIPDRFSGSGSGTDF
TLTISRLEPEDFAVYYCQQMRGRPPTFGQGTKVEIK

REFERENCES

All references cited anywhere in this specification, including those cited anywhere above, are hereby incorporated by reference in their entirety and for all purposes.

Amit et al. (1986), Science, 233:747-753.
Andersen et al. (2002) Current Opinion in Biotechnology 13: 117
Ausubel et al. (1999) 4*th* eds., *Short Protocols in Molecular Biology: A Compendium of Methods from Current Protocols in Molecular Biology*, John Wiley & Sons.
Bagshawe K. D. et al. (1991) Antibody, Immunoconjugates and Radiopharmaceuticals 4: 915-922
Balza et al., (1990), FEES Lett., 261, 175-178.
Batista et al. J. Exp. Med., 184: 2197-205, 1996.
Berndt et al. *Histochem Cell Biol* 1998, 109(3):249-255.
Berndt et al., (2006) J Cancer Res Clin Oncol, 132, 537-546.
Bigner et al., J Clin Oncol (1998) 16, 2202-2212.
Binz and Plückthun, (2005), Nature Biotechnology, 23, 1257-1268
Birchler et al. (1999), J. Immunol. Methods, 231, 239-248.
Birchler et al. (1999), Nature Biotechnology, 17, 984-988.
Bird et al. (1988) Science, 242, 423-426
Borsi et al. (1987), J. Cell. Biol., 104, 595-600.
Borsi et al. (1995), J. Biol. Chem., 270: 6243-6245.
Borsi et al., 102, 75-85 (2002) Int. J. Cancer.
Bosslet et al. (1998), Cancer Res., 58, 1195-1201.
Brack et al. (2006), Clin. Cancer Res., 12, 3200-3208.
Brosens I., 15, 229-233 (1997) Semin Reprod Endocrinol
Buyalos and Agarwal, 12, 377-381, (2000) Curr Opin Obstet Gynecol
Carnemolla et al. (1999), Am. J. Pathol. 154, 1345-1352.
Caton et al. (1990), J. Immunol., 144:1965-1968.
Chadd et al. (2001), Current Opinion in Biotechnology 12: 188-194
Chothia et al. (1987), J. Mol. Biol., 196:901-917.
Chothia et al. (1989), Nature, 342:877-883.
Compston A. and Coles A., (2002) Lancet, 359:1221-1231
Demartis et al., 28, 534-539 (2001) Eur. J. Nucl. Med.
Dennis et al. (2007) Cancer Res., 67, 254-261
Glennie M J et al., (1987) J. Immunol. 139, 2367-2375
Haan et al. (2004), BioCentury, 12(5): A1-A6.
Harlow and Lane, Antibodies: A Laboratory Manual, Cold Spring
Harbor Laboratory, Cold Spring Harbor N.Y., pp. 726, 1988
Holliger and Bohlen 1999 Cancer and metastasis rev. 18: 411-419.
Holliger et al. (1993a), Proc. Natl. Acad. Sci. USA 90 6444-6448.
Holliger et al. (1993b), Current Opinion Biotechnol 4, 446-449.
Holt et al. (2003) Trends in Biotechnology 21, 484-490.
Huston et al. (1988) PNAS USA, 85, 5879-5883.
Kabat et al. (1987) Sequences of Proteins of Immunological Interest. 4*th* Edition. US Department of Health and Human Services.
Kabat et al. (1991a), Sequences of Proteins of Immunological Interest, 5th Edition. US Department of Health and Human Services, Public Service, NIH, Washington. (a)
Kabat et al. (1991b), J. Immunol., 147:1709-1719.
Knappik et al., (2000) J. Mol. Biol. 296, 57-86.
Kohler and Milstein, Nature, 256:495-497, 1975
Koide et al. (1998), Journal of Molecular Biology, 284: 1141-1151.
Kontermann et al. (2001), S, Antibody Engineering, Springer-Verlag New York, LLC; ISBN: 3540413545.
Kornblihtt et al. (1984), Nucleic Acids Res. 12, 5853-5868.
Krebs et al. (2001), Journal of Immunological Methods, 254 67-84.
Kriegsmann et al. (2004) *Rheumatol Int*, 24(1):25-33.
Larrick J W and Thomas D W (2001) Current Opinion in Biotechnology 12:411-418.
Ledermann J. A. et al. (1991) Int. J. Cancer 47: 659-664
Li et al. Protein Engineering, 10: 731-736, 1997
Low et al., (2008) Acc. Chem. Res. 41, 120-129
Matter et al., (2004) Circulation Res. 95, 1225-1233
McCafferty et al., (1990) Nature, 348, 552-554.
Mendez, M. et al., (1997) Nature Genet, 15(2): 146-156.
Merchand et al., 1998 Nature Biotech. 16:677-681
Muse K, 31, 813-822 (1988) Clin Obstet Gynecol
Neri, D., and Bicknell, R. (2005), Nat Rev Cancer 5, 436-446.
Nygren et al. (1997), Current Opinion in Structural Biology, 7: 463-469.
Paganelli et al., *Eur J Nucl Med* (1994) 21, 314-321.
Paolella et al. (1988), Nucleic Acids Res. 16, 3545-3557.
Pini et al. (1998), J. Biol. Chem., 273, 21769-21776.
Plückthun (1991), Bio/Technology 9: 545-551.
Reardon et al., J Clin Oncol (2002), 20, 1389-1397.
Reiter et al. (1996), Nature Biotech, 14, 1239-1245.
Repp et al., (1995) J. Hemat. 377-382.
Ridgeway et al. (1996), Protein Eng., 9, 616-621.
Riva et al., *Int J Cancer* (1992) 51:7-13.
Riva et al., *Cancer Res* (1995), 55, 5952s-5956s.
Robinson ed., Sustained and Controlled Release Drug Delivery Systems, Marcel Dekker, Inc., New York, 1978
Rock and Markham, (1992), Lancet, 340, 1264-1267.
Rybak et al., (2007), Chem. Med. Chem, 2, 22-40
Rybak et al., (2007), Cancer Res., 67, 10948-10957
Sambrook and Russell, *Molecular Cloning: a Laboratory Manual:* 3rd edition, 2001, Cold Spring Harbor Laboratory Press
Schliemann and Neri, (2008), Biochim Biophys Acta, 1776, 175-192
Segal et al. (1974), PNAS, 71:4298-4302.

Sergeeva et al. (2006), Adv. Drug. Deliv. Rev., 58, 1622-1654
Sharon et al. (1990a), PNAS, 87:4814-4817.
Sharon et al. (1990b), J. Immunol., 144:4863-4869.
Shrama et al. (2006), Nat. Rev. Drug Discovery, 5, 147-159.
Staerz U. D. and Bevan M. J. 1986 PNAS 83
Summers R W, Elliott D E, Qadir K, Urban J F, Thompson R, Weinstock J V (2003) Am. J. Gastroentol 98:2034-2041
Suresh et al. (1986) Method Enzymol. 121: 210-228
Tarli et al. *Blood* 1999, 94(1):192-198.
Trachsel et al. *Arthritis Res Ther* 2007, 9(1): R9.
Trachsel et al., (2007) J. Inv. Dermatol., 127, 881-886.
Villa et al., (2008) Int. J. Cancer, 122, 2405-2413
Viti et al. (2000), Methods Enzymol., 326, 480-505.
Viti et al., 59, 347-352, (1999) Cancer Res.
Ward et al. (1989), Nature 341, 544-546.
Wess In: BioCentury, The Bernstein Report on BioBusiness, 12(42), A1-A7, 2004.

---

What is claimed is:

1. A method of delivering a molecule to the neovasculature of endometriotic tissue in a human or animal, said molecule being conjugated to a specific binding member which binds the ED-A isoform of fibronectin to form a conjugate and the method comprises administering the conjugate to the human or animal, wherein the specific binding member is an anti-EDA antibody or antigen binding fragment thereof comprising a heavy chain variable (VH) domain and a light chain variable (VL) domain, wherein
   (i) the heavy chain variable (VH) domain comprises heavy chain CDR1, CDR2 and CDR3 amino acid sequences in SEQ ID NO: 16; and
   (ii) the light chain variable (VL) domain comprises the light chain CDR1, CDR2 and CDR3 amino acid sequences in SEQ ID NO: 78.

2. The method of claim 1, wherein the molecule is a detectable label.

3. The method of claim 1, wherein the molecule is a radioisotope.

4. The method of claim 1, wherein the molecule is a bioactive molecule selected from the group consisting of a cytokine, hormone, a therapeutic radioisotope and a cytotoxic drug, and wherein the bioactive molecule is optionally conjugated to the specific binding member by a cleavable linker.

5. The method of claim 4, wherein the specific binding member is conjugated to the bioactive molecule by a cleavable linker.

6. A method of delivering a molecule to the neovasculature of endometriotic tissue in a human or animal, said molecule being conjugated to a specific binding member which binds the ED-A isoform of fibronectin to form a conjugate and the method comprises administering the conjugate to the human or animal wherein the specific binding member is an anti-EDA antibody comprising a VH domain comprising a framework and a set of complementarity determining regions HCDR1, HCDR2 and HCDR3, wherein
   HCDR1 has amino acid sequence SEQ ID NO: 42,
   HCDR2 has amino acid sequence SEQ ID NO: 56,
   HCDR3 has amino acid sequence SEQ ID NO: 60; and
   a VL domain comprising a set of complementarity determining regions LCDR1, LCDR2 and LCDR3 and a framework wherein
   LCDR1 has amino acid sequence SEQ ID NO: 102,
   LCDR2 has amino acid sequence SEQ ID NO: 114, and
   LCDR3 has amino acid sequence SEQ ID NO: 118.

7. The method of claim 1, wherein the specific binding member comprises a single chain Fv.

8. The method of claim 7, wherein the binding member is a small immunoprotein (SIP).

9. The method of claim 6, wherein the specific binding member is a diabody, a single chain Fv or a small immunoprotein (SIP).

10. The method of claim 6, wherein the molecule is a bioactive molecule selected from the group consisting of a cytokine, hormone, a therapeutic radioisotope and a cytotoxic drug, and wherein the bioactive molecule is optionally conjugated to the specific binding member by a cleavable linker.

11. The method of claim 10, wherein the specific binding member is conjugated to the bioactive molecule by a cleavable linker.

* * * * *

SEQUENCE LISTING

<160> NUMBER OF SEQ ID NOS: 142

<210> SEQ ID NO 1
<211> LENGTH: 354
<212> TYPE: DNA
<213> ORGANISM: Artificial sequence
<220> FEATURE:
<223> OTHER INFORMATION: Synthetic sequence: H1 VH domain

<400> SEQUENCE: 1

```
gaggtgcagc tggtggagtc tgggggaggc ttggtacagc ctgggggtc  cctgagactc      60 tcctgtgcag cctctggatt cacctttagc ccgcggagga tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaagtact     300
catttgtatc tttttgacta ctggggccag ggaaccctgg tcaccgtctc gagt          354
```

<210> SEQ ID NO 2
<211> LENGTH: 118
<212> TYPE: PRT
<213> ORGANISM: Artificial sequence
<220> FEATURE:
<223> OTHER INFORMATION: Synthetic sequence: H1 VH domain

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Arg
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 3
<211> LENGTH: 354
<212> TYPE: DNA
<213> ORGANISM: Artificial sequence
<220> FEATURE:
<223> OTHER INFORMATION: Synthetic sequence: B2 VH domain -continued

<400> SEQUENCE: 3

```
gaggtgcagc tggtggagtc tgggggaggc ttggtacagc ctgggggtc cctgagactc      60
tcctgtgcag cctctggatt cacctttagc gcggctaaga tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaagtact    300
catttgtatc ttttttgacta ctggggccag ggaaccctgg tcaccgtctc gagt          354
```

<210> SEQ ID NO 4
<211> LENGTH: 118
<212> TYPE: PRT
<213> ORGANISM: Artificial sequence
<220> FEATURE:
<223> OTHER INFORMATION: Synthetic sequence: B2 VH domain

<400> SEQUENCE: 4

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Ala
             20                  25                  30

Lys Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
            115
```

<210> SEQ ID NO 5
<211> LENGTH: 354
<212> TYPE: DNA
<213> ORGANISM: Artificial sequence
<220> FEATURE:
<223> OTHER INFORMATION: Synthetic sequence: C5 VH domain

<400> SEQUENCE: 5

```
gaggtgcagc tggtggagtc tgggggaggc ttggtacagc ctgggggtc cctgagactc      60
tcctgtgcag cctctggatt cacctttagc ccgattacta tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaagtact    300
catttgtatc ttttttgacta ctggggccag ggaaccctgg tcaccgtctc gagt          354
```

<210> SEQ ID NO 6
<211> LENGTH: 118
<212> TYPE: PRT
<213> ORGANISM: Artificial sequence
<220> FEATURE:
<223> OTHER INFORMATION: Synthetic sequence: C5 VH domain

<400> SEQUENCE: 6

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Ile
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 7
<211> LENGTH: 354
<212> TYPE: DNA
<213> ORGANISM: Artificial sequence
<220> FEATURE:
<223> OTHER INFORMATION: Synthetic sequence: D5 VH domain

<400> SEQUENCE: 7
gaggtgcagc tggtggagtc tgggggaggc ttggtacagc ctggggggtc cctgagactc      60
tcctgtgcag cctctggatt cacctttagc gtgatgaaga tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtat attactgtgc gaaaagtact    300
catttgtatc tttttgacta ctggggccag ggaaccctgg tcaccgtctc gagt           354

<210> SEQ ID NO 8
<211> LENGTH: 118
<212> TYPE: PRT
<213> ORGANISM: Artificial sequence
<220> FEATURE:
<223> OTHER INFORMATION: Synthetic sequence: D5 VH domain

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Met
            20                  25                  30

Lys Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser

-continued

```
            115

<210> SEQ ID NO 9
<211> LENGTH: 354
<212> TYPE: DNA
<213> ORGANISM: Artificial sequence
<220> FEATURE:
<223> OTHER INFORMATION: Synthetic sequence: E5 VH domain

<400> SEQUENCE: 9
gaggtgcagc tggtggagtc tgggggaggc ttggtacagc ctggggggtc cctgagactc      60
tcctgtgcag cctctggatt cacctttagc actggttcta tgagctgggt ccgccaggct     120
ccagggaagg ggctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtat attactgtgc gaaaagtact    300
catttgtatc tttttgacta ctggggccag ggaaccctgg tcaccgtctc gagt           354

<210> SEQ ID NO 10
<211> LENGTH: 118
<212> TYPE: PRT
<213> ORGANISM: Artificial sequence
<220> FEATURE:
<223> OTHER INFORMATION: Synthetic sequence: E5 VH domain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Ser Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 11
<211> LENGTH: 354
<212> TYPE: DNA
<213> ORGANISM: Artificial sequence
<220> FEATURE:
<223> OTHER INFORMATION: Synthetic sequence: C8 VH domain

<400> SEQUENCE: 11
gaggtgcagc tggtggagtc tgggggaggc ttggtacagc ctggggggtc cctgagactc      60
tcctgtgcag cctctggatt cacctttagc cttcagacta tgagctgggt ccgccaggct     120
ccagggaagg ggctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtat attactgtgc gaaaagtact    300
catttgtatc tttttgacta ctggggccag ggaaccctgg tcaccgtctc gagt           354
```

<210> SEQ ID NO 12
<211> LENGTH: 118
<212> TYPE: PRT
<213> ORGANISM: Artificial sequence
<220> FEATURE:
<223> OTHER INFORMATION: Synthetic sequence: C8 VH domain

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Leu Gln
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 13
<211> LENGTH: 354
<212> TYPE: DNA
<213> ORGANISM: Artificial sequence
<220> FEATURE:
<223> OTHER INFORMATION: Synthetic sequence: F8 VH domain

<400> SEQUENCE: 13

```
gaggtgcagc tggtggagtc tgggggaggc ttggtacagc ctggggggtc cctgagactc     60
tcctgtgcag cctctggatt cacctttagc ctgtttacga tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtat attactgtgc gaaaagtact    300
catttgtatc ttttgacta ctggggccag ggaaccctgg tcaccgtctc gagt           354
```

<210> SEQ ID NO 14
<211> LENGTH: 118
<212> TYPE: PRT
<213> ORGANISM: Artificial sequence
<220> FEATURE:
<223> OTHER INFORMATION: Synthetic sequence: F8 VH domain

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 15
<211> LENGTH: 354
<212> TYPE: DNA
<213> ORGANISM: Artificial sequence
<220> FEATURE:
<223> OTHER INFORMATION: Synthetic sequence: F8 VH V5L domain

<400> SEQUENCE: 15

```
gaggtgcagc tgttggagtc tgggggaggc ttggtacagc ctgggggatc cctgagactc    60
tcctgtgcag cctctggatt cacctttagc ctgtttacga tgagctgggt ccgccaggct   120
ccagggaagg gctggagtg gtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaaagtact   300
catttgtatc tttttgacta ctggggccag ggaaccctgg tcaccgtctc gagt         354
```

<210> SEQ ID NO 16
<211> LENGTH: 118
<212> TYPE: PRT
<213> ORGANISM: Artificial sequence
<220> FEATURE:
<223> OTHER INFORMATION: Synthetic sequence: F8 VH V5L domain

<400> SEQUENCE: 16

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Leu Phe
                20                  25                  30

Thr Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 17
<211> LENGTH: 354
<212> TYPE: DNA
<213> ORGANISM: Artificial sequence
<220> FEATURE:
<223> OTHER INFORMATION: Synthetic sequence: F1 VH domain

<400> SEQUENCE: 17

```
gaggtgcagc tggtggagtc tgggggaggc ttggtacagc ctgggggatc cctgagactc    60
```

```
tcctgtgcag cctctggatt cacctttagc taggcgcgta tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaagtact    300
catttgtatc tttttgacta ctggggccag ggaaccctgg tcaccgtctc gagt          354
```

```
<210> SEQ ID NO 18
<211> LENGTH: 118
<212> TYPE: PRT
<213> ORGANISM: Artificial sequence
<220> FEATURE:
<223> OTHER INFORMATION: Synthetic sequence: F1 VH domain

<400> SEQUENCE: 18
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gln Ala
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

```
<210> SEQ ID NO 19
<211> LENGTH: 354
<212> TYPE: DNA
<213> ORGANISM: Artificial sequence
<220> FEATURE:
<223> OTHER INFORMATION: Synthetic sequence: B7 VH domain

<400> SEQUENCE: 19
gaggtgcagc tggtggagtc tgggggaggc ttggtacagc ctggggggtc cctgagactc     60
tcctgtgcag cctctggatt cacctttagc cattttgata tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaagtact    300
catttgtatc tttttgacta ctggggccag ggaaccctgg tcaccgtctc gagt          354
```

```
<210> SEQ ID NO 20
<211> LENGTH: 118
<212> TYPE: PRT
<213> ORGANISM: Artificial sequence
<220> FEATURE:
<223> OTHER INFORMATION: Synthetic sequence: B7 VH domain

<400> SEQUENCE: 20
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Phe
                20                  25                  30

Asp Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
            115

<210> SEQ ID NO 21
<211> LENGTH: 354
<212> TYPE: DNA
<213> ORGANISM: Artificial sequence
<220> FEATURE:
<223> OTHER INFORMATION: Synthetic sequence: E8 VH domain

<400> SEQUENCE: 21
gaggtgcagc tggtggagtc tgggggaggc ttggtacagc ctggggggtc cctgagactc      60
tcctgtgcag cctctggatt cacctttagc gatatgcata tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat     240
ctgcaaatga acagcctgag agccgaggac acggccgtat attactgtgc gaaaagtact    300
catttgtatc tttttgacta ctggggccag ggaaccctgg tcaccgtctc gagt           354

<210> SEQ ID NO 22
<211> LENGTH: 118
<212> TYPE: PRT
<213> ORGANISM: Artificial sequence
<220> FEATURE:
<223> OTHER INFORMATION: Synthetic sequence: E8 VH domain

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Met
                20                  25                  30

His Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
            115

<210> SEQ ID NO 23
<211> LENGTH: 354
<212> TYPE: DNA
<213> ORGANISM: Artificial sequence
<220> FEATURE:
<223> OTHER INFORMATION: Synthetic sequence: G9 VH domain

<400> SEQUENCE: 23

```
gaggtgcagc tggtggagtc tgggggaggc ttggtacagc ctgggggtc cctgagactc      60
tcctgtgcag cctctggatt cacctttagc catatgcaga tgagctgggt ccgccaggct    120
ccagggaagg gctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac acggccgtat attactgtgc gaaaagtact    300
catttgtatc tttttgacta ctggggccag ggaaccctgg tcaccgtctc gagt          354
```

<210> SEQ ID NO 24
<211> LENGTH: 118
<212> TYPE: PRT
<213> ORGANISM: Artificial sequence
<220> FEATURE:
<223> OTHER INFORMATION: Synthetic sequence: G9 VH domain

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Met
            20                  25                  30

Gln Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 25
<211> LENGTH: 348
<212> TYPE: DNA
<213> ORGANISM: Artificial sequence
<220> FEATURE:
<223> OTHER INFORMATION: Synthetic sequence: F16 VH domain

<400> SEQUENCE: 25

```
gaggtgcagc tgttggagtc tgggggaggc ttggtacagc ctgggggtc cctgagactc      60
tcctgtgcag cctctggatt cacctttagc cggtatggta tgagctgggt ccgccaggct    120
ccagggaagg gctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac acggccgtat attactgtgc gaaagcgcat    300
aatgcttttg actactgggg ccagggaacc ctggtcaccg tgtcgaga                 348
```

<210> SEQ ID NO 26

<211> LENGTH: 116
<212> TYPE: PRT
<213> ORGANISM: Artificial sequence
<220> FEATURE:
<223> OTHER INFORMATION: Synthetic sequence: F16 VH domain

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 27
<211> LENGTH: 348
<212> TYPE: DNA
<213> ORGANISM: Artificial sequence
<220> FEATURE:
<223> OTHER INFORMATION: Synthetic sequence: 4A1-F16 VH domain

<400> SEQUENCE: 27
gaggtgcagc tgttggagtc tgggggaggc ttggtacagc ctgggggtc cctgagactc      60 tcctgtgcag cctctggatt cacctttagc cggtatggtg cgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagcgcat    300
aatgcttttg actactgggg ccagggaacc ctggtcaccg tgtcgaga                 348

<210> SEQ ID NO 28
<211> LENGTH: 116
<212> TYPE: PRT
<213> ORGANISM: Artificial sequence
<220> FEATURE:
<223> OTHER INFORMATION: Synthetic sequence: 4A1-F16 VH domain

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Ala Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 29
<211> LENGTH: 9
<212> TYPE: DNA
<213> ORGANISM: Artificial sequence
<220> FEATURE:
<223> OTHER INFORMATION: Synthetic sequence: H1 VH CDR1

<400> SEQUENCE: 29 ccgcggagg                                                              9

<210> SEQ ID NO 30
<211> LENGTH: 3
<212> TYPE: PRT
<213> ORGANISM: Artificial sequence
<220> FEATURE:
<223> OTHER INFORMATION: Synthetic sequence: H1 VH CDR1

<400> SEQUENCE: 30

Pro Arg Arg
1

<210> SEQ ID NO 31
<211> LENGTH: 9
<212> TYPE: DNA
<213> ORGANISM: Artificial sequence
<220> FEATURE:
<223> OTHER INFORMATION: Synthetic sequence: B2 VH CDR1

<400> SEQUENCE: 31 gcggctaag                                                              9

<210> SEQ ID NO 32
<211> LENGTH: 3
<212> TYPE: PRT
<213> ORGANISM: Artificial sequence
<220> FEATURE:
<223> OTHER INFORMATION: Synthetic sequence: B2 VH CDR1

<400> SEQUENCE: 32

Ala Ala Lys
1

<210> SEQ ID NO 33
<211> LENGTH: 9
<212> TYPE: DNA
<213> ORGANISM: Artificial sequence
<220> FEATURE:
<223> OTHER INFORMATION: Synthetic sequence: C5 VH CDR1

<400> SEQUENCE: 33 ccgattact                                                              9

<210> SEQ ID NO 34
<211> LENGTH: 3
<212> TYPE: PRT
<213> ORGANISM: Artificial sequence
<220> FEATURE:
<223> OTHER INFORMATION: Synthetic sequence: C5 VH CDR1
```

```
<400> SEQUENCE: 34

Pro Ile Thr
1

<210> SEQ ID NO 35
<211> LENGTH: 9
<212> TYPE: DNA
<213> ORGANISM: Artificial sequence
<220> FEATURE:
<223> OTHER INFORMATION: Synthetic sequence: D5 VH CDR1

<400> SEQUENCE: 35 gtgatgaag                                                              9

<210> SEQ ID NO 36
<211> LENGTH: 3
<212> TYPE: PRT
<213> ORGANISM: Artificial sequence
<220> FEATURE:
<223> OTHER INFORMATION: Synthetic sequence: D5 VH CDR1

<400> SEQUENCE: 36

Val Met Lys
1

<210> SEQ ID NO 37
<211> LENGTH: 9
<212> TYPE: DNA
<213> ORGANISM: Artificial sequence
<220> FEATURE:
<223> OTHER INFORMATION: Synthetic sequence: E5 VH CDR1

<400> SEQUENCE: 37 actggttct                                                              9

<210> SEQ ID NO 38
<211> LENGTH: 3
<212> TYPE: PRT
<213> ORGANISM: Artificial sequence
<220> FEATURE:
<223> OTHER INFORMATION: Synthetic sequence: E5 VH CDR1

<400> SEQUENCE: 38

Thr Gly Ser
1

<210> SEQ ID NO 39
<211> LENGTH: 9
<212> TYPE: DNA
<213> ORGANISM: Artificial sequence
<220> FEATURE:
<223> OTHER INFORMATION: Synthetic sequence: C8 VH CDR1

<400> SEQUENCE: 39 cttcagact                                                              9

<210> SEQ ID NO 40
<211> LENGTH: 3
<212> TYPE: PRT
<213> ORGANISM: Artificial sequence
<220> FEATURE:
<223> OTHER INFORMATION: Synthetic sequence: C8 VH CDR1

<400> SEQUENCE: 40

Leu Gln Thr
1
```

<210> SEQ ID NO 41
<211> LENGTH: 9
<212> TYPE: DNA
<213> ORGANISM: Artificial sequence
<220> FEATURE:
<223> OTHER INFORMATION: Synthetic sequence: F8 VH and F8 VH V5L CDR1

<400> SEQUENCE: 41 ctgtttacg                                                                  9

<210> SEQ ID NO 42
<211> LENGTH: 3
<212> TYPE: PRT
<213> ORGANISM: Artificial sequence
<220> FEATURE:
<223> OTHER INFORMATION: Synthetic sequence: F8 VH and F8 VH V5L CDR1

<400> SEQUENCE: 42

Leu Phe Thr
1

<210> SEQ ID NO 43
<211> LENGTH: 9
<212> TYPE: DNA
<213> ORGANISM: Artificial sequence
<220> FEATURE:
<223> OTHER INFORMATION: Synthetic sequence: F1 VH CDR1

<400> SEQUENCE: 43 taggcgcgt                                                                  9

<210> SEQ ID NO 44
<211> LENGTH: 3
<212> TYPE: PRT
<213> ORGANISM: Artificial sequence
<220> FEATURE:
<223> OTHER INFORMATION: Synthetic sequence: F1 VH CDR1

<400> SEQUENCE: 44

Gln Ala Arg
1

<210> SEQ ID NO 45
<211> LENGTH: 9
<212> TYPE: DNA
<213> ORGANISM: Artificial sequence
<220> FEATURE:
<223> OTHER INFORMATION: Synthetic sequence: B7 VH CDR1

<400> SEQUENCE: 45 cattttgat                                                                  9

<210> SEQ ID NO 46
<211> LENGTH: 3
<212> TYPE: PRT
<213> ORGANISM: Artificial sequence
<220> FEATURE:
<223> OTHER INFORMATION: Synthetic sequence: B7 VH CDR1

<400> SEQUENCE: 46

His Phe Asp
1

<210> SEQ ID NO 47
<211> LENGTH: 9

-continued

```
<212> TYPE: DNA
<213> ORGANISM: Artificial sequence
<220> FEATURE:
<223> OTHER INFORMATION: Synthetic sequence: E8 VH CDR1

<400> SEQUENCE: 47 gatatgcat                                                          9

<210> SEQ ID NO 48
<211> LENGTH: 3
<212> TYPE: PRT
<213> ORGANISM: Artificial sequence
<220> FEATURE:
<223> OTHER INFORMATION: Synthetic sequence: E8 VH CDR1

<400> SEQUENCE: 48

Asp Met His
1

<210> SEQ ID NO 49
<211> LENGTH: 9
<212> TYPE: DNA
<213> ORGANISM: Artificial sequence
<220> FEATURE:
<223> OTHER INFORMATION: Synthetic sequence: G9 VH CDR1

<400> SEQUENCE: 49 catatgcag                                                          9

<210> SEQ ID NO 50
<211> LENGTH: 3
<212> TYPE: PRT
<213> ORGANISM: Artificial sequence
<220> FEATURE:
<223> OTHER INFORMATION: Synthetic sequence: G9 VH CDR1

<400> SEQUENCE: 50

His Met Gln
1

<210> SEQ ID NO 51
<211> LENGTH: 15
<212> TYPE: DNA
<213> ORGANISM: Artificial sequence
<220> FEATURE:
<223> OTHER INFORMATION: Synthetic sequence: F16 VH CDR1

<400> SEQUENCE: 51
cggtatggta tgagc                                                  15

<210> SEQ ID NO 52
<211> LENGTH: 5
<212> TYPE: PRT
<213> ORGANISM: Artificial sequence
<220> FEATURE:
<223> OTHER INFORMATION: Synthetic sequence: F16 VH CDR1

<400> SEQUENCE: 52

Arg Tyr Gly Met Ser
1               5

<210> SEQ ID NO 53
<211> LENGTH: 15
<212> TYPE: DNA
<213> ORGANISM: Artificial sequence
<220> FEATURE:
<223> OTHER INFORMATION: Synthetic sequence: 4A1-F16 VH CDR1
```

<210> SEQ ID NO 54
<211> LENGTH: 5
<212> TYPE: PRT
<213> ORGANISM: Artificial sequence
<220> FEATURE:
<223> OTHER INFORMATION: Synthetic sequence: 4A1-F16 VH CDR1

<400> SEQUENCE: 54

Arg Tyr Gly Ala Ser
1               5

<210> SEQ ID NO 55
<211> LENGTH: 18
<212> TYPE: DNA
<213> ORGANISM: Artificial sequence
<220> FEATURE:
<223> OTHER INFORMATION: Synthetic sequence: H1, B2, C5, D5, E5, C8, F8,
      F8 V5L, F1, B7, E8 and G9 VH CDR2

<400> SEQUENCE: 55
agtggtagtg gtggtagc                                                   18

<210> SEQ ID NO 56
<211> LENGTH: 6
<212> TYPE: PRT
<213> ORGANISM: Artificial sequence
<220> FEATURE:
<223> OTHER INFORMATION: Synthetic sequence: H1, B2, C5, D5, E5, C8, F8,
      F8 V5L, F1, B7, E8 and G9 VH CDR2

<400> SEQUENCE: 56

Ser Gly Ser Gly Gly Ser
1               5

<210> SEQ ID NO 57
<211> LENGTH: 51
<212> TYPE: DNA
<213> ORGANISM: Artificial sequence
<220> FEATURE:
<223> OTHER INFORMATION: Synthetic sequence: F16 and 4A1-F16 VH CDR2

<400> SEQUENCE: 57
gctattagtg gtagtggtgg tagcacatac tacgcagact ccgtgaaggg c               51

<210> SEQ ID NO 58
<211> LENGTH: 17
<212> TYPE: PRT
<213> ORGANISM: Artificial sequence
<220> FEATURE:
<223> OTHER INFORMATION: Synthetic sequence: F16 and 4A1-F16 VH CDR2

<400> SEQUENCE: 58

Ala Ile Ser Gly Ser Gly Gly Ser Thr Tyr Tyr Ala Asp Ser Val Lys
1               5                   10                  15
Gly

<210> SEQ ID NO 59
<211> LENGTH: 18
<212> TYPE: DNA
<213> ORGANISM: Artificial sequence
<220> FEATURE:
<223> OTHER INFORMATION: Synthetic sequence: H1, B2, C5, D5, E5, C8, F8, F8 V5L, F1, B7, E8 and G9 VH CDR3

<400> SEQUENCE: 59
agtactcatt tgtatctt                                                    18

<210> SEQ ID NO 60
<211> LENGTH: 6
<212> TYPE: PRT
<213> ORGANISM: Artificial sequence
<220> FEATURE:
<223> OTHER INFORMATION: Synthetic sequence: H1, B2, C5, D5, E5, C8, F8,
      F8 V5L, F1, B7, E8 and G9 VH CDR3

<400> SEQUENCE: 60

Ser Thr His Leu Tyr Leu
1               5

<210> SEQ ID NO 61
<211> LENGTH: 21
<212> TYPE: DNA
<213> ORGANISM: Artificial sequence
<220> FEATURE:
<223> OTHER INFORMATION: Synthetic sequence: F16 and 4A1-F16 VH CDR3

<400> SEQUENCE: 61
gcgcataatg cttttgacta c                                                21

<210> SEQ ID NO 62
<211> LENGTH: 7
<212> TYPE: PRT
<213> ORGANISM: Artificial sequence
<220> FEATURE:
<223> OTHER INFORMATION: Synthetic sequence: F16 and 4A1-F16 VH CDR3

<400> SEQUENCE: 62

Ala His Asn Ala Phe Asp Tyr
1               5

<210> SEQ ID NO 63
<211> LENGTH: 324
<212> TYPE: DNA
<213> ORGANISM: Artificial sequence
<220> FEATURE:
<223> OTHER INFORMATION: Synthetic sequence: H1 VL domain

<400> SEQUENCE: 63
gaaattgtgt tgacgcagtc tccaggcacc ctgtctttgt ctccagggga aaaagccacc      60
ctctcctgca gggccagtca gagtgttagc tctgcgtggt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagatgcgtg gtcggccgcc gacgttcggc     300
caagggacca aggtggaaat caaa                                            324

<210> SEQ ID NO 64
<211> LENGTH: 108
<212> TYPE: PRT
<213> ORGANISM: Artificial sequence
<220> FEATURE:
<223> OTHER INFORMATION: Synthetic sequence: H1 VL domain

<400> SEQUENCE: 64

Glu Ile Val Leu Thr Gln Ser Pro Gly Thr Leu Ser Leu Ser Pro Gly
1               5                   10                  15

```
Glu Lys Ala Thr Leu Ser Cys Arg Ala Ser Gln Ser Val Ser Ser Ala
                20                  25                  30

Trp Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                      55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 65
<211> LENGTH: 324
<212> TYPE: DNA
<213> ORGANISM: Artificial sequence
<220> FEATURE:
<223> OTHER INFORMATION: Synthetic sequence: B2 VL domain

<400> SEQUENCE: 65

```
gaaattgtgt tgacgcagtc tccaggcacc ctgtctttgt ctccagggga aaaagccacc      60
ctctcctgca gggccagtca gagtgttagc gtggcttttt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagatgcgtg gtcggccgcc gacgttcggc     300
caagggacca aggtggaaat caaa                                            324
```

<210> SEQ ID NO 66
<211> LENGTH: 108
<212> TYPE: PRT
<213> ORGANISM: Artificial sequence
<220> FEATURE:
<223> OTHER INFORMATION: Synthetic sequence: B2 VL domain

<400> SEQUENCE: 66

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Val Ala
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                      55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 67
<211> LENGTH: 324
<212> TYPE: DNA
<213> ORGANISM: Artificial sequence
<220> FEATURE:
<223> OTHER INFORMATION: Synthetic sequence: C5 VL domain

<400> SEQUENCE: 67

```
gaaattgtgt tgacgcagtc tccaggcacc ctgtctttgt ctccagggga aaaagccacc    60
ctctcctgca gggccagtca gagtgttagc ttgcattttt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagatgcgtg gtcggccgcc gacgttcggc   300
caagggacca aggtggaaat caaa                                          324
```

<210> SEQ ID NO 68
<211> LENGTH: 108
<212> TYPE: PRT
<213> ORGANISM: Artificial sequence
<220> FEATURE:
<223> OTHER INFORMATION: Synthetic sequence: C5 VL domain

<400> SEQUENCE: 68

```
Glu Ile Val Leu Thr Gln Ser Pro Gly Thr Leu Ser Leu Ser Pro Gly
1               5                  10                  15

Glu Lys Ala Thr Leu Ser Cys Arg Ala Ser Gln Ser Val Ser Leu His
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 69
<211> LENGTH: 324
<212> TYPE: DNA
<213> ORGANISM: Artificial sequence
<220> FEATURE:
<223> OTHER INFORMATION: Synthetic sequence: D5 VL domain

<400> SEQUENCE: 69

```
gaaattgtgt tgacgcagtc tccaggcacc ctgtctttgt ctccagggga aaaagccacc    60
ctctcctgca gggccagtca gagtgttagc aatgctttt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagatgcgtg gtcggccgcc gacgttcggc   300
caagggacca aggtggaaat caaa                                          324
```

<210> SEQ ID NO 70
<211> LENGTH: 108
<212> TYPE: PRT
<213> ORGANISM: Artificial sequence
<220> FEATURE:
<223> OTHER INFORMATION: Synthetic sequence: D5 VL domain

<400> SEQUENCE: 70

```
Glu Ile Val Leu Thr Gln Ser Pro Gly Thr Leu Ser Leu Ser Pro Gly
```

```
                1               5                   10                  15
            Glu Lys Ala Thr Leu Ser Cys Arg Ala Ser Gln Ser Val Ser Asn Ala
                            20                  25                  30

Phe Leu Ala Trp Tyr Gln Gln Lys Pro Gly Gln Ala Pro Arg Leu Leu
                        35                  40                  45

Ile Tyr Gly Ala Ser Ser Arg Ala Thr Gly Ile Pro Asp Arg Phe Ser
                50                  55                  60

Gly Ser Gly Ser Gly Thr Asp Phe Thr Leu Thr Ile Ser Arg Leu Glu
            65                  70                  75                  80

Pro Glu Asp Phe Ala Val Tyr Tyr Cys Gln Gln Met Arg Gly Arg Pro
                            85                  90                  95

Pro Thr Phe Gly Gln Gly Thr Lys Val Glu Ile Lys
                            100                 105
```

<210> SEQ ID NO 71
<211> LENGTH: 324
<212> TYPE: DNA
<213> ORGANISM: Artificial sequence
<220> FEATURE:
<223> OTHER INFORMATION: Synthetic sequence: E5 VL domain

<400> SEQUENCE: 71

```
gaaattgtgt tgacgcagtc tccaggcacc ctgtctttgt ctccagggga aaaagccacc    60
ctctcctgca gggccagtca gagtgttagc cttgcgcatt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagatgcgtg gtcggccgcc gacgttcggc   300
caagggacca aggtggaaat caaa                                          324
```

<210> SEQ ID NO 72
<211> LENGTH: 108
<212> TYPE: PRT
<213> ORGANISM: Artificial sequence
<220> FEATURE:
<223> OTHER INFORMATION: Synthetic sequence: E5 VL domain

<400> SEQUENCE: 72

```
            Glu Ile Val Leu Thr Gln Ser Pro Gly Thr Leu Ser Leu Ser Pro Gly
            1               5                   10                  15

Glu Lys Ala Thr Leu Ser Cys Arg Ala Ser Gln Ser Val Ser Leu Ala
                            20                  25                  30

His Leu Ala Trp Tyr Gln Gln Lys Pro Gly Gln Ala Pro Arg Leu Leu
                        35                  40                  45

Ile Tyr Gly Ala Ser Ser Arg Ala Thr Gly Ile Pro Asp Arg Phe Ser
                50                  55                  60

Gly Ser Gly Ser Gly Thr Asp Phe Thr Leu Thr Ile Ser Arg Leu Glu
            65                  70                  75                  80

Pro Glu Asp Phe Ala Val Tyr Tyr Cys Gln Gln Met Arg Gly Arg Pro
                            85                  90                  95

Pro Thr Phe Gly Gln Gly Thr Lys Val Glu Ile Lys
                            100                 105
```

<210> SEQ ID NO 73
<211> LENGTH: 324
<212> TYPE: DNA
<213> ORGANISM: Artificial sequence
<220> FEATURE:

<223> OTHER INFORMATION: Synthetic sequence: C8 VL domain

<400> SEQUENCE: 73

```
gaaattgtgt tgacgcagtc tccaggcacc ctgtctttgt ctccagggga aaaagccacc      60
ctctcctgca gggccagtca gagtgttagc cttcctttt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagatgcgtg gtcggccgcc gacgttcggc     300
caagggacca aggtggaaat caaa                                           324
```

<210> SEQ ID NO 74
<211> LENGTH: 108
<212> TYPE: PRT
<213> ORGANISM: Artificial sequence
<220> FEATURE:
<223> OTHER INFORMATION: Synthetic sequence: C8 VL domain

<400> SEQUENCE: 74

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Leu Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 75
<211> LENGTH: 324
<212> TYPE: DNA
<213> ORGANISM: Artificial sequence
<220> FEATURE:
<223> OTHER INFORMATION: Synthetic sequence: F8 VL domain

<400> SEQUENCE: 75

```
gaaattgtgt tgacgcagtc tccaggcacc ctgtctttgt ctccagggga aaaagccacc      60
ctctcctgca gggccagtca gagtgttagc atgccgtttt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagatgcgtg gtcggccgcc gacgttcggc     300
caagggacca aggtggaaat caaa                                           324
```

<210> SEQ ID NO 76
<211> LENGTH: 108
<212> TYPE: PRT
<213> ORGANISM: Artificial sequence
<220> FEATURE:
<223> OTHER INFORMATION: Synthetic sequence: F8 VL domain

<400> SEQUENCE: 76

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 77
<211> LENGTH: 324
<212> TYPE: DNA
<213> ORGANISM: Artificial sequence
<220> FEATURE:
<223> OTHER INFORMATION: Synthetic sequence: F8 VL K18R domain

<400> SEQUENCE: 77

```
gaaattgtgt tgacgcagtc tccaggcacc ctgtctttgt ctccagggga aagagccacc    60
ctctcctgca gggccagtca gagtgttagc atgccgtttt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagatgcgtg gtcggccgcc gacgttcggc   300
caagggacca aggtggaaat caaa                                          324
```

<210> SEQ ID NO 78
<211> LENGTH: 108
<212> TYPE: PRT
<213> ORGANISM: Artificial sequence
<220> FEATURE:
<223> OTHER INFORMATION: Synthetic sequence: F8 VL K18R domain

<400> SEQUENCE: 78

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 79
<211> LENGTH: 324
<212> TYPE: DNA
<213> ORGANISM: Artificial sequence
<220> FEATURE:
<223> OTHER INFORMATION: Synthetic sequence: F1 VL domain

<400> SEQUENCE: 79

```
gaaattgtgt tgacgcagtc tccaggcacc ctgtctttgt ctccagggga aaaagccacc    60
ctctcctgca gggccagtca gagtgttagc gcgccttttt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagatgcgtg gtcggccgcc gacgttcggc   300
caagggacca aggtggaaat caaa                                          324
```

<210> SEQ ID NO 80
<211> LENGTH: 108
<212> TYPE: PRT
<213> ORGANISM: Artificial sequence
<220> FEATURE:
<223> OTHER INFORMATION: Synthetic sequence: F1 VL domain

<400> SEQUENCE: 80

```
Glu Ile Val Leu Thr Gln Ser Pro Gly Thr Leu Ser Leu Ser Pro Gly
1               5                   10                  15
Glu Lys Ala Thr Leu Ser Cys Arg Ala Ser Gln Ser Val Ser Ala Pro
            20                  25                  30
Phe Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Met Arg Gly Arg Pro
                85                  90                  95
Pro Thr Phe Gly Gln Gly Thr Lys Val Glu Ile Lys
            100                 105
```

<210> SEQ ID NO 81
<211> LENGTH: 324
<212> TYPE: DNA
<213> ORGANISM: Artificial sequence
<220> FEATURE:
<223> OTHER INFORMATION: Synthetic sequence: B7 VL domain

<400> SEQUENCE: 81

```
gaaattgtgt tgacgcagtc tccaggcacc ctgtctttgt ctccagggga aaaagccacc    60
ctctcctgca gggccagtca gagtgttagc ctggcttttt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagatgcgtg gtcggccgcc gacgttcggc   300
caagggacca aggtggaaat caaa                                          324
```

<210> SEQ ID NO 82
<211> LENGTH: 108
<212> TYPE: PRT
<213> ORGANISM: Artificial sequence
<220> FEATURE:
<223> OTHER INFORMATION: Synthetic sequence: B7 VL domain

<400> SEQUENCE: 82

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Leu Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 83
<211> LENGTH: 324
<212> TYPE: DNA
<213> ORGANISM: Artificial sequence
<220> FEATURE:
<223> OTHER INFORMATION: Synthetic sequence: E8 VL domain

<400> SEQUENCE: 83

```
gaaattgtgt tgacgcagtc tccaggcacc ctgtctttgt ctccagggga aaaagccacc      60
ctctcctgca gggccagtca gagtgttagc tcgtcttttt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagatgcgtg gtcggccgcc gacgttcggc     300
caagggacca aggtggaaat caaa                                            324
```

<210> SEQ ID NO 84
<211> LENGTH: 108
<212> TYPE: PRT
<213> ORGANISM: Artificial sequence
<220> FEATURE:
<223> OTHER INFORMATION: Synthetic sequence: E8 VL domain

<400> SEQUENCE: 84

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 85
<211> LENGTH: 324
<212> TYPE: DNA

<213> ORGANISM: Artificial sequence
<220> FEATURE:
<223> OTHER INFORMATION: Synthetic sequence: G9 VL domain

<400> SEQUENCE: 85

```
gaaattgtgt tgacgcagtc tccaggcacc ctgtctttgt ctccagggga aaaagccacc    60
ctctcctgca gggccagtca gagtgttagc actgcttttt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagatgcgtg gtcggccgcc gacgttcggc   300
caagggacca aggtggaaat caaa                                          324
```

<210> SEQ ID NO 86
<211> LENGTH: 108
<212> TYPE: PRT
<213> ORGANISM: Artificial sequence
<220> FEATURE:
<223> OTHER INFORMATION: Synthetic sequence: G9 VL domain

<400> SEQUENCE: 86

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Thr Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 87
<211> LENGTH: 324
<212> TYPE: DNA
<213> ORGANISM: Artificial sequence
<220> FEATURE:
<223> OTHER INFORMATION: Synthetic sequence: F16 and 4A1-F16 VL domain

<400> SEQUENCE: 87

```
tcgtctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa acaaccggc cctcagggat cccagaccga   180
ttctctggct ccagctcagg aaacacagct tccttgacca tcactgggc tcaggcggaa   240 gatgaggctg actattactg taactcctct gtttatacta tgccgccgt ggtattcggc   300 ggagggacca agctgaccgt ccta                                          324
```

<210> SEQ ID NO 88
<211> LENGTH: 108
<212> TYPE: PRT
<213> ORGANISM: Artificial sequence
<220> FEATURE:
<223> OTHER INFORMATION: Synthetic sequence: F16 and 4A1-F16 VL domain

<400> SEQUENCE: 88

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu
            100                 105

<210> SEQ ID NO 89
<211> LENGTH: 9
<212> TYPE: DNA
<213> ORGANISM: Artificial sequence
<220> FEATURE:
<223> OTHER INFORMATION: Synthetic sequence: H1 VL CDR1

<400> SEQUENCE: 89 tctgcgtgg                                                                9

<210> SEQ ID NO 90
<211> LENGTH: 3
<212> TYPE: PRT
<213> ORGANISM: Artificial sequence
<220> FEATURE:
<223> OTHER INFORMATION: Synthetic sequence: H1 VL CDR1

<400> SEQUENCE: 90

Ser Ala Trp
1

<210> SEQ ID NO 91
<211> LENGTH: 9
<212> TYPE: DNA
<213> ORGANISM: Artificial sequence
<220> FEATURE:
<223> OTHER INFORMATION: Synthetic sequence: B2 VL CDR1

<400> SEQUENCE: 91 gtggctttt                                                                9

<210> SEQ ID NO 92
<211> LENGTH: 3
<212> TYPE: PRT
<213> ORGANISM: Artificial sequence
<220> FEATURE:
<223> OTHER INFORMATION: Synthetic sequence: B2 VL CDR1

<400> SEQUENCE: 92

Val Ala Phe
1

<210> SEQ ID NO 93
<211> LENGTH: 9
<212> TYPE: DNA
<213> ORGANISM: Artificial sequence
<220> FEATURE:

<223> OTHER INFORMATION: Synthetic sequence: C5 VL CDR1

<400> SEQUENCE: 93 ttgcatttt                                                                  9

<210> SEQ ID NO 94
<211> LENGTH: 3
<212> TYPE: PRT
<213> ORGANISM: Artificial sequence
<220> FEATURE:
<223> OTHER INFORMATION: Synthetic sequence: C5 VL CDR1

<400> SEQUENCE: 94

Leu His Phe
1

<210> SEQ ID NO 95
<211> LENGTH: 9
<212> TYPE: DNA
<213> ORGANISM: Artificial sequence
<220> FEATURE:
<223> OTHER INFORMATION: Synthetic sequence: D5 VL CDR1

<400> SEQUENCE: 95 aatgctttt                                                                  9

<210> SEQ ID NO 96
<211> LENGTH: 3
<212> TYPE: PRT
<213> ORGANISM: Artificial sequence
<220> FEATURE:
<223> OTHER INFORMATION: Synthetic sequence: D5 VL CDR1

<400> SEQUENCE: 96

Asn Ala Phe
1

<210> SEQ ID NO 97
<211> LENGTH: 9
<212> TYPE: DNA
<213> ORGANISM: Artificial sequence
<220> FEATURE:
<223> OTHER INFORMATION: Synthetic sequence: E5 VL CDR1

<400> SEQUENCE: 97 cttgcgcat                                                                  9

<210> SEQ ID NO 98
<211> LENGTH: 3
<212> TYPE: PRT
<213> ORGANISM: Artificial sequence
<220> FEATURE:
<223> OTHER INFORMATION: Synthetic sequence: E5 VL CDR1

<400> SEQUENCE: 98

Leu Ala His
1

<210> SEQ ID NO 99
<211> LENGTH: 9
<212> TYPE: DNA
<213> ORGANISM: Artificial sequence
<220> FEATURE:
<223> OTHER INFORMATION: Synthetic sequence: C8 VL CDR1

<400> SEQUENCE: 99 cttcctttt                                                      9

<210> SEQ ID NO 100
<211> LENGTH: 3
<212> TYPE: PRT
<213> ORGANISM: Artificial sequence
<220> FEATURE:
<223> OTHER INFORMATION: Synthetic sequence: C8 VL CDR1

<400> SEQUENCE: 100

Leu Pro Phe
1

<210> SEQ ID NO 101
<211> LENGTH: 9
<212> TYPE: DNA
<213> ORGANISM: Artificial sequence
<220> FEATURE:
<223> OTHER INFORMATION: Synthetic sequence: F8 VL and F8 VL K18R CDR1

<400> SEQUENCE: 101 atgccgttt                                                      9

<210> SEQ ID NO 102
<211> LENGTH: 3
<212> TYPE: PRT
<213> ORGANISM: Artificial sequence
<220> FEATURE:
<223> OTHER INFORMATION: Synthetic sequence: F8 VL and F8 VL K18R CDR1

<400> SEQUENCE: 102

Met Pro Phe
1

<210> SEQ ID NO 103
<211> LENGTH: 9
<212> TYPE: DNA
<213> ORGANISM: Artificial sequence
<220> FEATURE:
<223> OTHER INFORMATION: Synthetic sequence: F1 VL CDR1

<400> SEQUENCE: 103 gcgccttt                                                       9

<210> SEQ ID NO 104
<211> LENGTH: 3
<212> TYPE: PRT
<213> ORGANISM: Artificial sequence
<220> FEATURE:
<223> OTHER INFORMATION: Synthetic sequence: F1 VL CDR1

<400> SEQUENCE: 104

Ala Pro Phe
1

<210> SEQ ID NO 105
<211> LENGTH: 9
<212> TYPE: DNA
<213> ORGANISM: Artificial sequence
<220> FEATURE:
<223> OTHER INFORMATION: Synthetic sequence: B7 VL CDR1

<400> SEQUENCE: 105 ctggctttt                                                      9

<210> SEQ ID NO 106

-continued

```
<211> LENGTH: 3
<212> TYPE: PRT
<213> ORGANISM: Artificial sequence
<220> FEATURE:
<223> OTHER INFORMATION: Synthetic sequence: B7 VL CDR1

<400> SEQUENCE: 106

Leu Ala Phe
1

<210> SEQ ID NO 107
<211> LENGTH: 9
<212> TYPE: DNA
<213> ORGANISM: Artificial sequence
<220> FEATURE:
<223> OTHER INFORMATION: Synthetic sequence: E8 VL CDR1

<400> SEQUENCE: 107 tcgtctttt                                                              9

<210> SEQ ID NO 108
<211> LENGTH: 3
<212> TYPE: PRT
<213> ORGANISM: Artificial sequence
<220> FEATURE:
<223> OTHER INFORMATION: Synthetic sequence: E8 VL CDR1

<400> SEQUENCE: 108

Ser Ser Phe
1

<210> SEQ ID NO 109
<211> LENGTH: 9
<212> TYPE: DNA
<213> ORGANISM: Artificial sequence
<220> FEATURE:
<223> OTHER INFORMATION: Synthetic sequence: G9 VL CDR1

<400> SEQUENCE: 109 actgctttt                                                              9

<210> SEQ ID NO 110
<211> LENGTH: 3
<212> TYPE: PRT
<213> ORGANISM: Artificial sequence
<220> FEATURE:
<223> OTHER INFORMATION: Synthetic sequence: G9 VL CDR1

<400> SEQUENCE: 110

Thr Ala Phe
1

<210> SEQ ID NO 111
<211> LENGTH: 33
<212> TYPE: DNA
<213> ORGANISM: Artificial sequence
<220> FEATURE:
<223> OTHER INFORMATION: Synthetic sequence: F16 and 4A1-F16 VL CDR1

<400> SEQUENCE: 111
caaggagaca gcctcagaag ctattatgca agc                                  33

<210> SEQ ID NO 112
<211> LENGTH: 11
<212> TYPE: PRT
<213> ORGANISM: Artificial sequence
<220> FEATURE:
```

<223> OTHER INFORMATION: Synthetic sequence: F16 and 4A1-F16 VL CDR1

<400> SEQUENCE: 112

Gln Gly Asp Ser Leu Arg Ser Tyr Tyr Ala Ser
1               5                   10

<210> SEQ ID NO 113
<211> LENGTH: 21
<212> TYPE: DNA
<213> ORGANISM: Artificial sequence
<220> FEATURE:
<223> OTHER INFORMATION: Synthetic sequence: H1, B2, C5, D5, E5, C8, F8,
      F8 K18R, F1, B7, E and G9 VL CDR2

<400> SEQUENCE: 113
ggtgcatcca gcagggccac t                                              21

<210> SEQ ID NO 114
<211> LENGTH: 7
<212> TYPE: PRT
<213> ORGANISM: Artificial sequence
<220> FEATURE:
<223> OTHER INFORMATION: Synthetic sequence: H1, B2, C5, D5, E5, C8, F8,
      F8 K18R, F1, B7, E and G9 VL CDR2

<400> SEQUENCE: 114

Gly Ala Ser Ser Arg Ala Thr
1               5

<210> SEQ ID NO 115
<211> LENGTH: 21
<212> TYPE: DNA
<213> ORGANISM: Artificial sequence
<220> FEATURE:
<223> OTHER INFORMATION: Synthetic sequence: F16 and 4A1-F16 VL CDR2

<400> SEQUENCE: 115
ggtaaaaaca accggccctc a                                              21

<210> SEQ ID NO 116
<211> LENGTH: 7
<212> TYPE: PRT
<213> ORGANISM: Artificial sequence
<220> FEATURE:
<223> OTHER INFORMATION: Synthetic sequence: F16 and 4A1-F16 VL CDR2

<400> SEQUENCE: 116

Gly Lys Asn Asn Arg Pro Ser
1               5

<210> SEQ ID NO 117
<211> LENGTH: 18
<212> TYPE: DNA
<213> ORGANISM: Artificial sequence
<220> FEATURE:
<223> OTHER INFORMATION: Synthetic sequence: H1, B2, C5, D5, E5, C8, F8,
      F8 K18R, F1, B7, E and G9 VL CDR3

<400> SEQUENCE: 117
atgcgtggtc ggccgccg                                                  18

<210> SEQ ID NO 118
<211> LENGTH: 6
<212> TYPE: PRT
<213> ORGANISM: Artificial sequence
<220> FEATURE:
<223> OTHER INFORMATION: Synthetic sequence: H1, B2, C5, D5, E5, C8, F8, F8 K18R, F1, B7, E and G9 VL CDR3

<400> SEQUENCE: 118

Met Arg Gly Arg Pro Pro
1               5

<210> SEQ ID NO 119
<211> LENGTH: 33
<212> TYPE: DNA
<213> ORGANISM: Artificial sequence
<220> FEATURE:
<223> OTHER INFORMATION: Synthetic sequence: F16 and 4A1-F16 VL CDR3

<400> SEQUENCE: 119
aactcctctg tttatactat gccgcccgtg gta                                   33

<210> SEQ ID NO 120
<211> LENGTH: 11
<212> TYPE: PRT
<213> ORGANISM: Artificial sequence
<220> FEATURE:
<223> OTHER INFORMATION: Synthetic sequence: F16 and 4A1-F16 VL CDR3

<400> SEQUENCE: 120

Asn Ser Ser Val Tyr Thr Met Pro Pro Val Val
1               5                   10

<210> SEQ ID NO 121
<211> LENGTH: 15
<212> TYPE: DNA
<213> ORGANISM: Artificial sequence
<220> FEATURE:
<223> OTHER INFORMATION: Synthetic sequence: F8, F16 and 4A1-F16 linker

<400> SEQUENCE: 121
ggcggtagcg gaggg                                                       15

<210> SEQ ID NO 122
<211> LENGTH: 5
<212> TYPE: PRT
<213> ORGANISM: Artificial sequence
<220> FEATURE:
<223> OTHER INFORMATION: Synthetic sequence: F8, F16 and 4A1-F16 linker

<400> SEQUENCE: 122

Gly Gly Ser Gly Gly
1               5

<210> SEQ ID NO 123
<211> LENGTH: 118
<212> TYPE: PRT
<213> ORGANISM: Artificial sequence
<220> FEATURE:
<223> OTHER INFORMATION: Synthetic sequence:  H1 VH V5L domain

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Arg
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 124
<211> LENGTH: 118
<212> TYPE: PRT
<213> ORGANISM: Artificial sequence
<220> FEATURE:
<223> OTHER INFORMATION: Synthetic sequence: B2 VH V5L domain

<400> SEQUENCE: 124

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Ala
            20                  25                  30

Lys Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 125
<211> LENGTH: 118
<212> TYPE: PRT
<213> ORGANISM: Artificial sequence
<220> FEATURE:
<223> OTHER INFORMATION: Synthetic sequence: C5 VH V5L domain

<400> SEQUENCE: 125

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Ile
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 126
<211> LENGTH: 118
<212> TYPE: PRT
<213> ORGANISM: Artificial sequence
<220> FEATURE:
<223> OTHER INFORMATION: Synthetic sequence: D5 VH V5L domain

<400> SEQUENCE: 126

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Met
            20                  25                  30

Lys Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 127
<211> LENGTH: 118
<212> TYPE: PRT
<213> ORGANISM: Artificial sequence
<220> FEATURE:
<223> OTHER INFORMATION: Synthetic sequence: E5 VH V5L domain

<400> SEQUENCE: 127

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Ser Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 128
<211> LENGTH: 118
<212> TYPE: PRT
<213> ORGANISM: Artificial sequence
<220> FEATURE:
<223> OTHER INFORMATION: Synthetic sequence: C8 VH V5L domain

<400> SEQUENCE: 128

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Gln
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Thr His Leu Tyr Leu Phe Asp Tyr Trp Gly Gln Gly Thr
            100                 105                 110

Leu Val Thr Val Ser Ser
            115
```

<210> SEQ ID NO 129
<211> LENGTH: 118
<212> TYPE: PRT
<213> ORGANISM: Artificial sequence
<220> FEATURE:
<223> OTHER INFORMATION: Synthetic sequence: F1 VH V5L domain

<400> SEQUENCE: 129

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Ala
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Thr His Leu Tyr Leu Phe Asp Tyr Trp Gly Gln Gly Thr
            100                 105                 110

Leu Val Thr Val Ser Ser
            115
```

<210> SEQ ID NO 130
<211> LENGTH: 118
<212> TYPE: PRT
<213> ORGANISM: Artificial sequence
<220> FEATURE:
<223> OTHER INFORMATION: Synthetic sequence: B7 VH V5L domain

<400> SEQUENCE: 130

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Phe
            20                  25                  30

Asp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 131
<211> LENGTH: 118
<212> TYPE: PRT
<213> ORGANISM: Artificial sequence
<220> FEATURE:
<223> OTHER INFORMATION: Synthetic sequence: E8 VH V5L domain

<400> SEQUENCE: 131

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Met
             20                  25                  30

His Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 132
<211> LENGTH: 118
<212> TYPE: PRT
<213> ORGANISM: Artificial sequence
<220> FEATURE:
<223> OTHER INFORMATION: Synthetic sequence: G9 VH V5L domain

<400> SEQUENCE: 132

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Met
             20                  25                  30

Gln Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
```

```
<210> SEQ ID NO 133
<211> LENGTH: 108
<212> TYPE: PRT
<213> ORGANISM: Artificial sequence
<220> FEATURE:
<223> OTHER INFORMATION: Synthetic sequence: H1 VL K18R domain

<400> SEQUENCE: 133

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ala
            20                  25                  30

Trp Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105

<210> SEQ ID NO 134
<211> LENGTH: 108
<212> TYPE: PRT
<213> ORGANISM: Artificial sequence
<220> FEATURE:
<223> OTHER INFORMATION: Synthetic sequence: B2 VL K18R domain

<400> SEQUENCE: 134

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105

<210> SEQ ID NO 135
<211> LENGTH: 108
<212> TYPE: PRT
<213> ORGANISM: Artificial sequence
<220> FEATURE:
<223> OTHER INFORMATION: Synthetic sequence: C5 VL K18R domain

<400> SEQUENCE: 135

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu His
            20                  25                  30
```

```
Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys
            100                 105

<210> SEQ ID NO 136
<211> LENGTH: 108
<212> TYPE: PRT
<213> ORGANISM: Artificial sequence
<220> FEATURE:
<223> OTHER INFORMATION: Synthetic sequence: D5 VL K18R domain

<400> SEQUENCE: 136

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Asn Ala
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys
            100                 105

<210> SEQ ID NO 137
<211> LENGTH: 108
<212> TYPE: PRT
<213> ORGANISM: Artificial sequence
<220> FEATURE:
<223> OTHER INFORMATION: Synthetic sequence: E5 VL K18R domain

<400> SEQUENCE: 137

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Leu Ala
                20                  25                  30

His Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys
            100                 105
```

<210> SEQ ID NO 138
<211> LENGTH: 108
<212> TYPE: PRT
<213> ORGANISM: Artificial sequence
<220> FEATURE:
<223> OTHER INFORMATION: Synthetic sequence: C8 VL K18R domain

<400> SEQUENCE: 138

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 139
<211> LENGTH: 108
<212> TYPE: PRT
<213> ORGANISM: Artificial sequence
<220> FEATURE:
<223> OTHER INFORMATION: Synthetic sequence: F1 VL K18R domain

<400> SEQUENCE: 139

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 140
<211> LENGTH: 108
<212> TYPE: PRT
<213> ORGANISM: Artificial sequence
<220> FEATURE:
<223> OTHER INFORMATION: Synthetic sequence: B7 VL K18R domain

<400> SEQUENCE: 140

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu Ala
            20                  25                  30

Phe Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys
                100                 105
```

<210> SEQ ID NO 141
<211> LENGTH: 108
<212> TYPE: PRT
<213> ORGANISM: Artificial sequence
<220> FEATURE:
<223> OTHER INFORMATION: Synthetic sequence: E8 VL K18R domain

<400> SEQUENCE: 141

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Phe Leu Ala Trp Tyr Gln Gln Lys Pro Gly Gln Ala Pro Arg Leu Leu
                 35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys
                100                 105
```

<210> SEQ ID NO 142
<211> LENGTH: 108
<212> TYPE: PRT
<213> ORGANISM: Artificial sequence
<220> FEATURE:
<223> OTHER INFORMATION: Synthetic sequence: G9 VL K18R domain

<400> SEQUENCE: 142

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Thr Ala
                 20                  25                  30

Phe Leu Ala Trp Tyr Gln Gln Lys Pro Gly Gln Ala Pro Arg Leu Leu
                 35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys
                100                 105
```